US010052346B2

(12) United States Patent
Marcus

(10) Patent No.: US 10,052,346 B2
(45) Date of Patent: Aug. 21, 2018

(54) TREATMENT OF MYELODYSPLASTIC SYNDROMES WITH 2-O AND,OR 3-O DESULFATED HEPARINOIDS

(71) Applicant: Cantex Pharmaceuticals, Inc., Weston, FL (US)

(72) Inventor: Stephen Marcus, Weston, FL (US)

(73) Assignee: Cantex Pharmaceuticals, Inc., Weston, FL (US)

( * ) Notice: Subject to any disclaimer, the term of this patent is extended or adjusted under 35 U.S.C. 154(b) by 127 days.

(21) Appl. No.: 15/044,740

(22) Filed: Feb. 16, 2016

(65) Prior Publication Data

US 2016/0235779 A1 Aug. 18, 2016

Related U.S. Application Data

(60) Provisional application No. 62/277,360, filed on Jan. 11, 2016, provisional application No. 62/181,513, filed on Jun. 18, 2015, provisional application No. 62/117,409, filed on Feb. 17, 2015.

(51) Int. Cl.
| | |
|---|---|
| *A61K 31/727* | (2006.01) |
| *A61K 31/44* | (2006.01) |
| *A61K 31/437* | (2006.01) |
| *A61K 31/706* | (2006.01) |
| *A61K 31/704* | (2006.01) |
| *A61K 31/7068* | (2006.01) |
| *A61K 31/4545* | (2006.01) |
| *A61K 31/517* | (2006.01) |
| *A61K 31/496* | (2006.01) |
| *A61K 31/506* | (2006.01) |
| *A61K 31/5025* | (2006.01) |
| *A61K 31/519* | (2006.01) |
| *A61K 31/4375* | (2006.01) |
| *A61K 45/06* | (2006.01) |
| *A61K 31/4439* | (2006.01) |
| *A61K 9/00* | (2006.01) |
| *A61K 47/02* | (2006.01) |

(52) U.S. Cl.
CPC .......... *A61K 31/727* (2013.01); *A61K 31/437* (2013.01); *A61K 31/4375* (2013.01); *A61K 31/44* (2013.01); *A61K 31/4439* (2013.01); *A61K 31/4545* (2013.01); *A61K 31/496* (2013.01); *A61K 31/506* (2013.01); *A61K 31/5025* (2013.01); *A61K 31/517* (2013.01); *A61K 31/519* (2013.01); *A61K 31/704* (2013.01); *A61K 31/706* (2013.01); *A61K 31/7068* (2013.01); *A61K 45/06* (2013.01); *A61K 9/0019* (2013.01); *A61K 47/02* (2013.01)

(58) Field of Classification Search
CPC ........... A61K 31/272; A61K 31/704–31/7125; A61K 31/727

See application file for complete search history.

(56) References Cited

U.S. PATENT DOCUMENTS

| | | |
|---|---|---|
| 4,239,754 A | 12/1980 | Sache et al. |
| 4,816,446 A | 3/1989 | Feller et al. |
| 5,250,519 A | 10/1993 | Conrad et al. |
| 5,296,471 A | 3/1994 | Holme et al. |
| 5,380,716 A | 1/1995 | Conrad et al. |
| 5,399,493 A | 3/1995 | Emerson et al. |
| 5,668,118 A | 9/1997 | Kennedy |
| 5,696,100 A | 12/1997 | Holme et al. |
| 5,707,974 A | 1/1998 | Kennedy |
| 5,714,477 A | 2/1998 | Einarsson |
| 5,795,875 A | 8/1998 | Holme et al. |
| 5,804,374 A | 9/1998 | Baltimore et al. |
| 5,808,021 A | 9/1998 | Holme et al. |
| 5,840,707 A | 11/1998 | Mannino et al. |
| 5,912,237 A | 6/1999 | Kennedy |
| 5,990,097 A | 11/1999 | Kennedy |
| 5,994,318 A | 11/1999 | Gould-Fogerite et al. |
| 6,077,683 A | 6/2000 | Kennedy |
| 6,153,217 A | 11/2000 | Jin et al. |
| 6,154,502 A | 11/2000 | Brun et al. |
| 6,406,862 B1 | 6/2002 | Krakauer |
| 6,489,311 B1 | 12/2002 | Kennedy |
| 6,514,502 B1 | 2/2003 | Francis |

(Continued)

FOREIGN PATENT DOCUMENTS

| | | |
|---|---|---|
| EP | 0140781 A2 | 5/1985 |
| EP | 0208623 A2 | 1/1987 |

(Continued)

OTHER PUBLICATIONS

Cazzola, M. et al "Myelodysplastic syndromes . . . " New Engl. J. Med., vol. 352, No. 6, pp. 536-538. (Year: 2005).*
Chambers, S. et al "Aging hematopoietic stem cells decline . . . " PLoS One, vol. 5, No. 8, pp. 1750-1762 (Year: 2007).*
Fernandez, C. et al "Semi-synthetic heparin derivatives . . . " Carbohyd. Res., vo 341, No. 10, pp. 1253-1265. (Year: 2006).*
Hachet-Haas, M. et al "Small neutralizing molecules to inhibit . . . " J. Biol. Chem., vol. 283, No. 34, pp. 23189-23199. (Year: 2008).*
Amara, A., et al., "Stromal Cell-derived Factor-1a Associates with Heparan Sulfates through the First b-Strand of the Chemokine," The Journal of Biological Chemistry, 1999, pp. 23916-23925, vol. 274, No. 34.

(Continued)

*Primary Examiner* — Leigh C Maier
(74) *Attorney, Agent, or Firm* — Fenwick & West LLP

(57) ABSTRACT

Methods are presented for treating cancers and hematopoietic stem cell disorders, comprising administering to a subject with a cancer or hematopoietic stem cell disorder who is receiving a treatment regimen, a heparin derivative capable of inhibiting, reducing, abrogating or otherwise interfering with the binding of CXCL12 to CXCR4, wherein the cancer or hematopoietic stem cell disorder is one in which interaction of CXCL12 with CXCR4 privileges the cancer or disordered HSCs against therapeutic intervention. In preferred embodiments, the heparin derivative is a substantially 2-O, 3-O-desulfated heparin derivative.

19 Claims, 3 Drawing Sheets

(56) References Cited

U.S. PATENT DOCUMENTS

Figure 1:
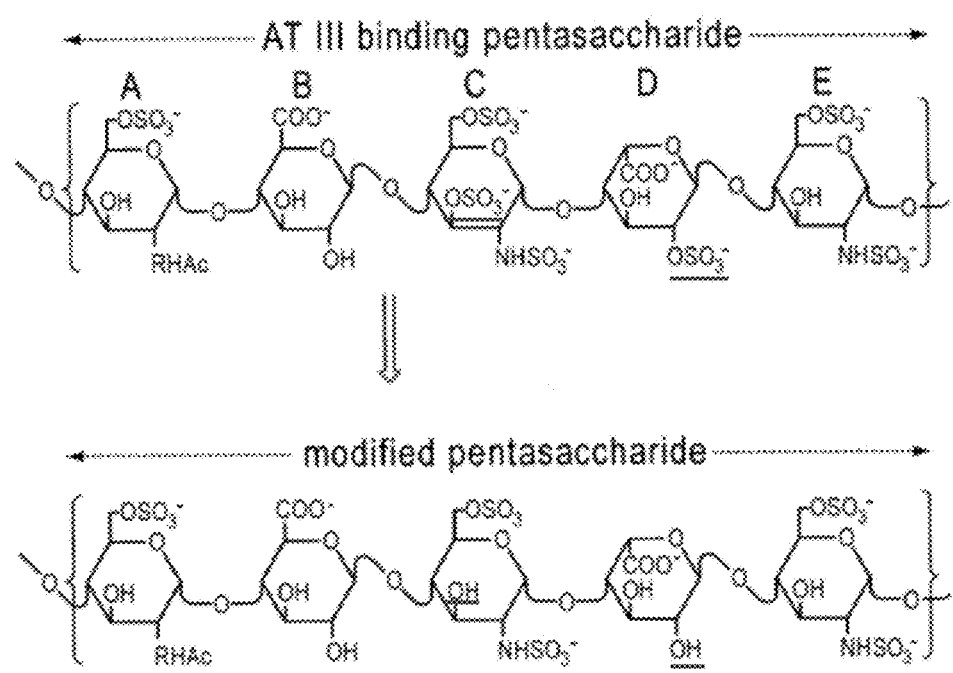

| | | | |
|---|---|---|---|
| 6,743,426 B2 | 6/2004 | Fisher et al. | |
| 7,468,358 B2 | 12/2008 | Kennedy et al. | |
| 7,538,096 B2 | 5/2009 | Hales et al. | |
| 8,404,716 B2* | 3/2013 | Zeldis .................. | A61K 31/454 514/319 |
| 8,734,804 B2 | 5/2014 | Marcus | |
| 9,271,999 B2 | 3/2016 | Marcus | |
| 2002/0122799 A1 | 9/2002 | Stern et al. | |
| 2003/0083231 A1 | 5/2003 | Ahlem et al. | |
| 2004/0180812 A1 | 9/2004 | Dicker et al. | |
| 2005/0215533 A1 | 9/2005 | Gottlieb et al. | |
| 2005/0261241 A1 | 11/2005 | Cardin | |
| 2005/0282775 A1 | 12/2005 | Kennedy | |
| 2006/0040896 A1 | 2/2006 | Kennedy | |
| 2006/0172968 A1 | 8/2006 | Casu et al. | |
| 2007/0021378 A1 | 1/2007 | Varki et al. | |
| 2007/0037776 A1 | 2/2007 | Richardson et al. | |
| 2007/0123489 A1 | 5/2007 | Kennedy et al. | |
| 2009/0036405 A1 | 2/2009 | Kennedy | |
| 2009/0054373 A1 | 2/2009 | Kennedy et al. | |
| 2009/0054374 A1 | 2/2009 | Kennedy | |
| 2009/0238852 A1 | 9/2009 | Kennedy | |
| 2009/0304711 A1 | 12/2009 | Pardoll et al. | |
| 2010/0003226 A1 | 1/2010 | Reed et al. | |
| 2010/0068192 A1 | 3/2010 | Enoki et al. | |
| 2010/0215751 A1 | 8/2010 | Desai et al. | |
| 2010/0316640 A1 | 12/2010 | Sundaram et al. | |
| 2010/0317616 A1 | 12/2010 | Prestwich et al. | |
| 2012/0052055 A1 | 3/2012 | Erickson-Miller | |
| 2012/0196828 A1 | 8/2012 | Marcus | |
| 2013/0034534 A1 | 2/2013 | Kronebero et al. | |
| 2013/0108587 A1 | 5/2013 | Drapeau | |
| 2013/0143840 A1 | 6/2013 | Parish et al. | |
| 2013/0303481 A1 | 11/2013 | Marcus | |
| 2016/0120947 A1 | 5/2016 | Scadden et al. | |
| 2016/0213706 A1 | 7/2016 | Marcus | |
| 2016/0243168 A1 | 8/2016 | Marcus | |
| 2016/0287626 A1 | 10/2016 | Marcus | |
| 2016/0296552 A1 | 10/2016 | Kennedy et al. | |
| 2017/0096549 A1 | 4/2017 | Johnson et al. | |
| 2017/0106011 A1 | 4/2017 | Marcus | |

FOREIGN PATENT DOCUMENTS

| | | |
|---|---|---|
| EP | 0380943 A1 | 8/1990 |
| EP | 0557887 A2 | 9/1993 |
| EP | 0583865 A1 | 2/1994 |
| EP | 1807095 B1 | 5/2011 |
| GB | 2270841 A | 3/1994 |
| JP | 2001-527583 A | 12/2001 |
| JP | 2006-076968 A | 3/2006 |
| JP | 2007-533670 A | 11/2007 |
| JP | 2008-518090 A | 5/2008 |
| JP | 2010-053135 A | 3/2010 |
| JP | 2010-529025 A | 8/2010 |
| WO | WO-1991/15216 A1 | 10/1991 |
| WO | WO-1993/019734 A1 | 10/1993 |
| WO | WO-1994/018989 A1 | 9/1994 |
| WO | WO-1995/030424 A1 | 11/1995 |
| WO | WO-1998/004133 A1 | 2/1998 |
| WO | WO-1998/035691 A1 | 8/1998 |
| WO | WO-1998/053852 A1 | 12/1998 |
| WO | WO-2001/019376 A1 | 3/2001 |
| WO | WO-2001/082918 A2 | 11/2001 |
| WO | WO-2003/088980 A1 | 10/2003 |
| WO | WO-2004/050673 A2 | 6/2004 |
| WO | WO-2005/000295 A1 | 1/2005 |
| WO | WO-2006/007392 A1 | 1/2006 |
| WO | WO-2006/023397 A2 | 3/2006 |
| WO | WO-2006/047755 A2 | 5/2006 |
| WO | WO-2007/115372 A1 | 10/2007 |
| WO | WO-2008/106584 A1 | 9/2008 |
| WO | WO-2009/015183 A1 | 1/2009 |
| WO | WO-2009/117677 A2 | 9/2009 |
| WO | WO-2011/116954 A2 | 9/2011 |
| WO | WO-2012/106379 A1 | 8/2012 |
| WO | WO-2013/016181 A1 | 1/2013 |
| WO | WO-2013/166163 A1 | 11/2013 |
| WO | WO-2013/169355 A1 | 11/2013 |
| WO | WO-2014/134539 A1 | 9/2014 |
| WO | WO-2015/061358 A1 | 4/2015 |
| WO | WO-2015/061604 A1 | 4/2015 |
| WO | WO-2015/142924 A1 | 9/2015 |
| WO | WO-2016/133907 A1 | 5/2016 |
| WO | WO-2016/133910 A1 | 8/2016 |
| WO | WO-2017/123549 A1 | 7/2017 |

OTHER PUBLICATIONS

Gschweng, E., et al., "Hematopoietic Stem Cells for Cancer Immunotherapy," Immunol Rev., 2014, pp. 237-249, vol. 257, No. 1.

Murphy, T., "The Many Faces of Pseudomonas aeruginosa in Chronic Obstructive Pulmonary Disease," Clinical Infectious Disease, Editorial Commentary, Dec. 2008, vol. 47, pp. 1534-1536.

Office Action for Japanese Patent Application No. JP 2017-054390, dated Dec. 19, 2017, 9 Pages.

Communication pursuant to Article 94(3) EPC for European Patent Application No. EP 13787651.2, dated Nov. 17, 2017, 6 Pages.

Chilean Patent Office, First Substantive Report for Chilean Patent Application No. 3017-2014, dated Jun. 21, 2017, 14 Pages (with concise explanation).

Eurasian Patent Organization, First Office Action for Eurasian Application No. 201492052/28, dated Aug. 2, 2016, 4 Pages. (with English translation).

Eurasian Patent Organization, Second Office Action for Eurasian Application No. 201492052/28, dated Jan. 30, 2017, 4 Pages. (with English translation).

Eurasian Patent Organization, Third Office Action for Eurasian Application No. 201492052/28, dated May 17, 2017, 6 Pages. (with English translation).

European Patent Office, Extended European Search Report for European Patent Application No. 13787651.2, dated Nov. 27, 2015, 12 Pages.

European Patent Office, Extended European Search Report for European Patent Application No. 14855522.0, dated Feb. 23, 2017, 7 Pages.

IP Australia, Examination Report, Australian Patent Application No. 2013260101, dated Sep. 5, 2016, 3 Pages.

IP Australia, Examination Report, Australian Patent Application No. 2016234916, dated Mar. 9, 2017, 4 Pages.

Intellectual Property Office of Singapore, Search Report and Written Opinion for Singapore Patent. Application No. 11201407340Y, dated Nov. 18, 2015, 13 Pages.

Intellectual Property Office of Singapore, Search Report and Second Written Opinion for Singapore Patent. Application No. 11201407340Y, dated Sep. 5, 2016, 8 Pages.

Intellectual Property Office of Singapore, Notice of Eligibility for Grant and Examination Report for Singapore Patent. Application No. 11201407340Y, dated Jan. 23, 2017, 7 Pages.

Intellectual Property Office of Singapore, Search Report and Written Opinion for Singapore Patent. Application No. 11201603081W, dated Jul. 6, 2017, 9 Pages.

Israeli Patent Office, Office Action for Israeli Patent Application No. 235593, dated Jun. 21, 2017, 5 Pages (with concise explanation).

Japanese Patent Office, Office Action for Japanese Patent Application No. 2015-511452, dated Dec. 15, 2016, 17 Pages. (with English translation).

Japanese Patent Office, Office Action for Patent Application No. 2015-511452, dated Mar. 30, 2017, 13 Pages. (with English translation).

State Intellectual Property Office, Office Action and Search Report for Chinese Patent Application No. 201380036055.1, dated Feb. 4, 2016, 8 Pages. (English translation).

State Intellectual Property Office, Second Office Action for Chinese Patent Application No. 201380036055.1, dated Oct. 20, 2016, 4 Pages. (English translation).

(56) References Cited

OTHER PUBLICATIONS

State Intellectual Property Office, Third Office Action for Chinese Patent Application No. 201380036055.1, dated May 18, 2017, 3 Pages. (English translation).
PCT International Preliminary Report on Patentability, International Application No. PCT/US2005/028771, dated Feb. 20, 2007, 9 Pages.
PCT International Search Report and Written Opinion, International Application No. PCT/US2005/028771, dated Oct. 4, 2006, 11 Pages.
PCT International Preliminary Report on Patentability, International Application No. PCT/US2000/024910, dated Jan. 22, 2002, 10 Pages.
PCT International Search Report, International Application No. PCT/US2000/024910, dated Jul. 2, 2001, 5 Pages.
PCT International Search Report, International Application No. PCT/US1997/012419, dated Oct. 10, 1997, 2 Pages.
PCT International Search Report and Written Opinion, International Application No. PCT/US2005/039011, dated Dec. 5, 2006, 4 Pages.
PCT International Preliminary Report on Patentability, International Application No. PCT/US2005/039011, dated Dec. 5, 2006, 4 Pages.
PCT International Search Report and Written Opinion, International Application No. PCT/US2008/055249, dated Aug. 11, 2008, 11 Pages.
PCT International Preliminary Report on Patentability, International Application No. PCT/US2008/055249, dated Sep. 1, 2009, 7 Pages.
PCT International Search Report and Written Opinion, International Application No. PCT/US2009/037836, dated Feb. 5, 2010, 12 Pages.
PCT International Preliminary Report on Patentability, International Application No. PCT/US2009/037836, dated Sep. 21, 2010, 8 Pages.
PCT International Search Report and Written Opinion, International Application No. PCT/US2012/023402, dated May 29, 2012, 8 Pages.
PCT International Preliminary Report on Patentability, International Application No. PCT/US2012/023402, dated Aug. 6, 2013, 6 Pages.
PCT International Preliminary Report on Patentability, International Application No. PCT/US2014062027, dated Apr. 26, 2016, 11 Pages.
PCT International Search Report and Written Opinion, International Application No. PCT/US2014062027, dated Jan. 16, 2015, 13 Pages.
PCT Invitation to Pay Additional Fees and, Where Applicable, Protest Fee from PCT/US2013/031053 dated May 10, 2013.
PCT International Search Report and Written Opinion, International Application No. PCT/US2013/031053 dated Jul. 1, 2013, 14 Pages.
PCT International Preliminary Report on Patentability, International Application No. PCT/US2013/031053 dated Nov. 11, 2014, 11 Pages.
PCT International Search Report and Written Opinion, International Application No. PCT/US2012/047577, dated Oct. 1, 2012, 9 Pages.
PCT International Preliminary Report on Patentability, International Application No. PCT/US2012/047577, dated Jan. 28, 2014, 7 Pages.
PCT International Search Report and Written Opinion, International Application No. PCT/US2014/061634, dated Feb. 9, 2015, 7 Pages.
PCT International Preliminary Report on Patentability, International Application No. PCT/US2014/061634, dated Aug. 15, 2015, 15 Pages.
PCT International Search Report and Written Opinion, International Application No. PCT/US2015/021068, dated Jun. 16, 2015, 10 Pages.
PCT International Search Report and Written Opinion, International Application No. PCT/US2016/018082, dated Apr. 29, 2016, 19 Pages.
PCT International Search Report and Written Opinion, International Application No. PCT/US2016/018086, dated May 5, 2016, 17 Pages.
PCT International Search Report and Written Opinion, International Application No. PCT/US2017/012861, dated May 16, 2017, 11 Pages.
Adams, J.M., et al., "The Bcl-2 Protein Family: Arbiters of Cell Survival," Science, 1998, pp. 1322-1326, vol. 281.
Ahmad, S., et al., "Functional Heterogeneity of Antiheparin-Platelet Factor 4 Antibodies: Implications in the Pathogenesis of the HIT Syndrome," Clinical and Applied Thrombosis/Hemostatis: Official Journal of the International Academy of Clinical and Applied Thrombosis/Hemostatis, 1999, pp. S32-S37, vol. 5, No. 1.
Ahmad, S., et al., "Synthetic Pentasaccharides Do Not Cause Platelet Activation by Antiheparin-Platelet Factor 4 Antibodies," Clin Appl Thrombosis/Hemostasis, 1999, pp. 259-266, vol. 5, No. 4.
Ahmed, T., et al., "Effects of Inhaled Heparin on Immunologic and Nonimmunologic Bronchoconstrictor Responses in Sheep," American Review of Respiratory Disease, 1992, pp. 566-570, vol. 145.
Ahmed, T., et al., "Preventing Bronchoconstriction in Exercise-Induced Asthma with Inhaled Heparin," The New England Journal of Medicine, 1993, pp. 90-95, vol. 329, No. 2.
Ahmed, T., et al., "Inhibition of Antigen-Induced Airway and Cutaneous Pharmacodynamic Study," Journal of Applied Physiology, 1993, pp. 1492-1498, vol. 74, No. 4.
Akimoto, H., et al., "Heparin and Heparan Sulfate Block Angiotensin-II-Induced Hypertrophy in Cultured Neonatal Rat Cardiomyocytes," Circulation, 1996, pp. 810-816, vol. 93.
Akpek, G., "A High-Dose Pulse Steriod Regimen for Controlling Active Chronic Graft-Versus-Host Disease," 2001, pp. 495-502, vol. 7.
Antalik, M., et al., "Spectrophotometric Detection of the Interaction Between Cytochrome C and Heparin," Biochem. Biophys, Acta, 1992, pp. 155-159, vol. 1100.
Antzelevitch, C., et al., "Electrophysiologic Properties and Antiarrhythmic Actions of a Novel Antianginal Agent," Journal of Cardiovascular Pharmacology and Therapeutics, 2004, 9(Suppl 1): S65-83.
Ashikari-Hada, S., et al., "Characterization of Growth Factor-Binding Structures in Heparin/Heparan Sulfate Using an Octasaccharide Library," The Journal of Biological Chemistry, 2004, pp. 12346-12354, vol. 279, No. 13.
Ashkenazi, A., et al., "Death Receptors: Signaling and Modulation," Science, 1998, pp. 1305-1308, vol. 281.
Bach, P.B., et al., "Management of Acute Exacerbations of Chronic Obstructive Pulmonary Disease: A Summary and Appraisal of Published Evidence," Ann Intern Med, 2001, pp. 600-620, vol. 134, No. 7.
Bachhuber, T., et al., "Regulation of the Epithelial Na+ Channel by the Protein Kinase CK2," The Journal of Biological Chemistry, 2008, pp. 13225-13232, vol. 283, No. 19.
Bagelova, J., et al., "Studies on Cytochrome c-Heparin Interactions by Differential Scanning Calorimetry," Biochem. J., 1994, pp. 99-101, vol. 297.
Baines, C. P., et al., "Loss of Cyclophilin D Reveals A Critical Role for Mitochondrial Permeability Transition in Cell Death," Nature, 2005, pp. 658-662, vol. 434.
Barinaga, M., "Stroke-Damaged Neurons May Commit Cellular Suicide," Science, 1998, pp. 1302-1303, vol. 281.
Barzu, T., et al., "O-Acylated heparin derivatives with low anticoagulant activity decrease proliferation and increase alpha-smooth muscle actin expression in cultured arterial smooth muscle cells," European Journal of Pharmacology, 1992, pp. 225-233, vol. 219.
Barzu, T., et al., "Preparation and Anti-HN Activity ofO-Acylated Heparin and Dermatan Sulfate Derivatives With Low Anticoagulant Effect," J Med. Chem., 1993, pp. 3546-3555, vol. 36.
Bates, S. M., et al., "Coagulation Assays," Circulation, 2005, pp. e53-e60.
Becker, L, B., "New Concepts in Reactive Oxygen Species and Cardiovascular Reperfusion Physiology," Cardiovascular Research, 2004, pp. 461-470, vol. 61.
Beg, A.A., et al., "An Essential Role for NF-KB in Preventing TNF-α-Induced Cell Death," Science, 1996, pp. 782-784, vol. 274.

(56) References Cited

OTHER PUBLICATIONS

Bezprozvanny, I. B., et al., "Activation of the Calcium Release Channel (Ryanodine Receptor) by Heparin and Other Polyanions is Calcium Dependent," Molecular Biology Cell, 1993, pp. 347-352, vol. 4.
Bierhaus, A., et al., "Understanding RAGE, the Receptor for Advanced Glycation End Products," Journal of Molecular Medicine, 2005, pp. 876-886, vol. 83.
Blaustein, M. P., et al., "Sodium/Calcium Exchange: Its Physiological Implications," Physiological Reviews, 1999, pp. 763-854, vol. 79.
Bolton, W. K., et al., "Randomized Trial of an Inhibitor of Formation of Advanced Glycation End Products in Diabetic Nephropathy," American Journal ofNephrology, 2004, pp. 32-40, vol. 24.
Boston, D. R., et al., "Effects of Angiotensin II on Intracellular Calcium and Contracture in Metabolically Inhibited Cardiomyocytes," The Journal of Pharmacology Experimental Therapeutics, 1998, pp. 716-723, vol. 285.
Bouwman, R. A., et al., "Cardioprotection Via Activation of Protein Kinase C-δ Depends on Modulation of the Reverse Mode of the Na+/Ca2+ Exchanger," Circulation, 2006, 114.1 suppl: I-226.
Bowler, S.D., et al., "Heparin Inhibits the Immediate Response to Antigen in the Skin and Lungs of Allergic Subjects," American Review of Respiratory Disease, 1993, pp. 160-163, vol. 147, No. 1.
Bozinovki, S., et al., "Serum Amyloid A is a Biomarker of Acute Exacerbations of Chronic Obstructive Pulmonary Disease," Am J Respir Crit Care Med, 2008, pp. 269-278, vol. 177.
Brookes, P. S., et al., "Calcium, ATP, and ROS: A Mitochondria! Love-Hate Triangle," Am J Physiol Cell Physiol, 2004, 287, No. 4, C817-C833.
Brown, R., et al., "Effects of heparin and related molecules upon neutrophil aggregation and elastase release in vitro," British Journal of Pharmacology, 2003, pp. 845-853, vol. 139, No. 4.
Burger, J.A., et al., "CXCR4: a key receptor in the crosstalk between tumor cells and their microenvironment," Blood, 2006, pp. 1761-1767, vol. 107.
Burger, J.A., et al., "The CXCR4 chemokine receptor in acute and chronic leukaemia: a marrow homing receptor and potential therapeutic target," British Journal of Haematology, 2007, pp. 288-296, vol. 137, No. 4.
Burris, H. A., et al., "Improvements in survival and clinical benefit with gemcitabine as first-line therapy for patients with advanced pancreas cancer: a randomized trial," Journal of Clinical Oncology, 1997, pp. 2403-2413, vol. 15, No. 6.
Cain, B.S., et al., "Therapeutic Strategies to Reduce TNF-a Mediated Cardiac Contractile Depression Following Ischemia and Reperfusion," Cell Cardiol., 1999, pp. 931-947, vol. 31.
Cardenes, H. R., et al., "Locally Advanced Pancreatic Cancer Current Therapeutic Approach," The Oncologist, 2006, pp. 612-623, vol. 11.
Carlson, M.K., et al., "Elevation of Hepatic Transaminases After Enoxaparin Use: Case Report and Review of Unfractionated and Low-Molecular-Weight Heparin-Induced Hepatotoxicity," Pharmacotherapy, 2001, pp. 108-113, vol. 21, No. 1.
Casu, B. et al., "Non-Anticoagulant Heparins and Inhibition of Cancer," Pathophysiology of Haemostasis and Thrombosis, 2007, pp. 195-203, vol. 36.
Ceol, M., et al., "Glycosaminoglycan therapy prevents TGF-β1 overexpression and pathologic changes in renal tissue of long-term diabetic rats," Journal of the American Society of Nephrology, 2000, pp. 2324-2336, vol. 11.
Cerami, C., et al., "Tobacco Smoke is a Source of Toxic Reactive Glycation Products, Proc. Natl. Acad. Sci., 1997, pp. 13915-13920, vol. 94.
Chaney, M. O., et al., "RAGE and Amyloid Beta Interations: Atomic Force Microscopy and Molecular Modeling," Biochimica et Biophysica Acta, 2005, pp. 199-205, vol. 1741.
Chang, M., et al., "C-Reactive Protein Binds to Both Oxidized LDL and Apoptotic Cells Through Recognition of a Common Ligand: Phosphorylcholine of Oxidized Phospholipids," Proc Natl Acad Sci USA, 2002, pp. 13043-13048, vol. 99, No. 20.
Chavakis, T., et al., "The Pattern Recognition Receptor (RAGE) is a Counterreceptor for Leukocyte Integrins: A Novel Pathway for Inflammatory Cell Recruitment," J Exp. Med., 2003, pp. 1507-1515, vol. 198, No. 10.
Chen, C., et al., "Myocardial Cell Death and Apoptosis in Hibernating Myocardium," JA.C.C., 1997, pp. 1407-1412, vol. 30, No. 5.
Chen, N., et al., "Autophagy as a therapeutic target in cancer," Cancer Biology & Therapy, 2011, pp. 157-168, vol. 11, No. 2.
Choay, J., et al., "Structure-Activity Relationship in Heparin: A Synthetic Pentasaccharide With High Affinity for Antithrombin III and Eliciting High Anti-Factor Xa Activity," Biochemical and Biophysical Research Communications, 1983, pp. 492-499, vol. 116, No. 2.
Chong, B. H., et al., "Heparin-Induced Thrombocytopenia," Expert Review of Cardiovascular Therapy, 2004, pp. 547-559, vol. 2, No. 4.
Clancy, C. E., et al., "Insights Into the Molecular Mechanisms of Bradycardia-Triggered Arrhythmias in Long QT-3 Syndrome," The Journal of Clinical Investigation, 2002, pp. 1251-1262, vol. 110, No. 9.
Cooper, B. W., et al., "A Phase I and Pharmacodynamic Study of Fludarabine, Carboplatin, and Topotecan in Patients With Relapsed, Refractory, or High-Risk Acute Leukemia," Clin Cancer Res, 2004, pp. 6830-6839, vol. 10.
Cosio, M.G., "Autoimmunity, T-Cells and STAT-4 in the Pathogenesis of Chronic Obstructive Pulmonary Disease," Eur. Respir J, 2004, pp. 3-5, vol. 24.
Crawford, J., et al., "Chemotherapy-Induced Neutropenia," Cancer, 2003, pp. 228-237, vol. 100, No. 2.
Croghan, G. A., et al., "A Study of Paclitaxel, Carboplatin, and Bortezomib in the Treatment of Metastatic Malignant Melanoma," Cancer, 2010, pp. 3463-3468, vol. 116.
Dahl, M., et al., "C-Reactive Protein as a Predictor of Prognosis in Chronic Obstructive Pulmonary Disease," Am J Respir Crit Care Med, 2007, pp. 250-255, vol. 175.
Dasgupta, J.D., et al., "Phospholipase C-yl Association with CD3 Structure in T Cells," J. Exp. Med., 1992, pp. 285-288, vol. 175, No. 1.
Davies, L., et al., "Oral Corticosteroids in Patients Admitted to Hospital With Exacerbations of Chronic Obstructive Pulmonary Disease: A Prospective Randomised Controlled Trial," Lancet, 1999, pp. 456-460, vol. 354.
De Jong, Y.P., et al., "Oral or IV Prednisolone in the Treatment of COPD Exacerbations," Chest, 2007, pp. 1741-1747, vol. 132, No. 6.
De Torres, J.P., et al., "C-Reactive Protein Levels and Clinically Important Predictive Outcomes in Stable COPD Patients," Eur Respir J, 2006, pp. 902-907, vol. 27, No. 5.
Deutsch, M. A., et al., "Carboplatin, etoposide, and radiotherapy, followed by surgery, for the treatment of marginally resectable non-small cell lung cancer," Cancer Treat Rev., 1993, vol. 19, Suppl C (Abstract).
Devaney, J.M., et al., "Neutrophil Elastase Up-Regulates Interleukin-8 Via Toll-Like Receptor 4," FEBS Letters, pp. 129-132, vol. 544.
Diamant, Z., et al., "Effect of Inhaled Heparin on Allergen-induced Early and Late Asthmatic Responses in Patients with Atopic Asthma," American Journal of Respiratory and Critical Care Medicine., 1996, pp. 1790-1795, vol., 153, No. 6.
Diamond, M. S., et al., "Heparin is an Adhesive Ligand for the Leukocyte Integrin Mac-1 (CD11b/CD18)," The Journal of Cell Biology, 1995, pp. 1473-1482, vol. 130.
Diaz, R. J., et al., "Studying Ischemic Preconditioning in Isolated Cardiomyocyte Models," Cardiovascular Research, 2006, pp. 286-296, vol. 70.
Dolowitz, D. A., et al., "The Use of Heparin in the Control of Allergies," Annals of Allergy, 1965, pp. 309-313, vol. 23.
Donaldson, G.C., et al., "Relationship Between Exacerbation Frequency and Lung Function Decline in Chronic Obstructive Pulmonary Disease," Thorax, 2002, pp. 847-852, vol. 57.

(56) References Cited

OTHER PUBLICATIONS

Drost, E.M., et al., "Oxidative Stress and Airway Inflammation in Severe Exacerbations of COPD," Thorax, 2005, pp. 293-300, vol. 60.
Dukes, G.E., et al., "Transaminase Elevations in Patients Receiving Bovine or Porcine Heparin," Ann Int Med, 1984, pp. 646-650, vol. 100.
Edens, R.E., et al., "Heparin is Not Just an Anticoagulant Anymore: Six and One-Half Decades of Studies on the Ability of Heparin to Regulate Complement Activity," Complement Today—Complement Profiles, 1993, pp. 96-120, vol. 1.
Ellerman, J. E., et al., "Masquerader: High Mobility Group Box-1 and Cancer," Clin Cancer Res., 2007, pp. 2836-2848, vol. 13, No. 10.
Fabris, F., et al., "Heparin-induced thrombocytopenia," Clin. Appl. Thrombosis/Hemostasis, 1997, pp. 203-209, vol. 3, No. 3.
Fabris, F., et al., "Pathophysiology of Heparin-Induced Thrombocytopenia," Arch Pathol Lab Med, 2000, pp. 1657-1666, vol. 124.
Fogarty, A.W., et al., "Systemic inflammation and Decline in Lung Function in a General Population," Thorax, 2007, pp. 515-520, vol. 62.
Fossa, A., "Total Body Irradiation," Oncolex, May 2012 [online][Retrieved on Jue 28, 2017] Retrieved from the Internet <URL: http://oncolex.org/prosedyrer/treatment/radiationtherapy/lymphoma_TBI?Ig>.
Foster, T.S., et al., "Assessment of the Economic Burden of COPD in the U.S.: A Review and Synthesis of the Literature," COPD: Journal of Chronic Obstructive Pulmonary Disease, 2006, pp. 211-218, vol. 3.
Frank, R. D., et al., "A Non-Anticoagulant Synthetic Pentasaccharide Reduces Inflammation in a Murine Model of Kidney Ischemia-Reperfusion Injury," Wound Healing and Inflammation/Infection, 2006, pp. 802-806, vol. 96.
Fraser, H., et al., "Ranolazine Decreases Diastolic Calcium Accumulation Caused by ATX-II or Ischemia in Rat Hearts," J Mal Cell Cardiol, 2006, pp. 1031-1038, vol. 41, No. 6.
Friedrichs, G. S., et al., "Effects of Heparin and N-Acetyl Heparin on Ischemia/Reperfusion-Induced Alterations in Myocardial Function in the Rabbit Isolated Heart," Circ Res, 1994, pp. 701-710, vol. 75, No. 4.
Friese, C. R., "Chemotherapy-Induced Neutropenia: Important New Data to Guide Nursing Assessment and Management," Advanced Studies in Nursing, 2006, pp. 21-25, vol. 4, No. 2.
Fryer, A., et al., "Selective O-Desulfation Produces Nonanticoagulant Heparin that Retains Pharmacological Activity in the Lung," J Pharmacol. Exp. Ther., 1997, pp. 208-219, vol. 282, No. 1.
Fryer, A., et al., "Function of Pulmonary M2 Muscarinic Receptors in Antigen-Challenged Guinea Pigs is Restored by Heparin and Poly-L-Glutamate," Journal of Clinical Investigation, 1992, pp. 2292-2298, vol. 90.
Gan, W.Q., et al., "Association Between chronic Obstructive Pulmonary Disease and Systemic Inflammation: A Systematic Review and a Meta-Analysis," Thorax, 2004, pp. 574-580, vol. 59.
Gao, C., et al., "Chemically modified heparin inhibits the in vitro adhesion of nonsmall cell lung cancer cells to P-selectin," Journal of Cancer Research and Clinical Oncology, 2005, pp. 257-264, vol. 132, No. 4.
Garcia-Dorado, D., et al., "Selective Inhibition of the Contractile Apparatus, A New Approach to Modification of Infarct Size, Infarct Composition, and Infarct Geometry During Coronary Artery Occlusion and Reperfusion," Circulation, 1992, pp. 1160-1174, vol. 85.
Garcia-Dorado, D., et al., "Gap Junction Uncoupler Heptanol Prevents Cell-to-Cell Progression of Hypercontracture and Limites Necrosis During Myocardial Reperfusion," Circulation, 1997, pp. 3579-3586, vol. 96.
Ghosh, T. K., et al., "Competitive, Reversible, and Potent Antagonism of Inositol 1,4,5-Trisphosphate-Activated Calcium Release by Heparin," J Biol Chem, 1988, pp. 11075-11079, vol. 263, No. 23.

Ghosn, M., et al., "FOLFOX-6 combination as the first-line treatment of locally advanced and/or metastatic pancreatic cancer," Am J Clin Oncol., 2007, pp. 15-20, vol. 30, No. 1 (Abstract).
Goldin, A., et al., "Advanced Glycation End Products: Sparking the Development of Diabetic Vascular Injury," Journal of the American Heart Association, 2006, pp. 597-605, vol. 114.
Goodman, R. B., et al, "Cytokine-mediated inflammation in acute lung injury", Cytokine & Growth Factor Reviews, 2003, pp. 523-535, vol. 14.
Gosens, R., et al., "Acetylcholine: a Novel Regulator of Airway Smooth Muscle Remodelling?," European Journal of Pharmacology 500, 2004, pp. 193-201.
Govan, J. R. W., et al., "Microbial Pathogenesis in Cystic Fibrosis: Mucoid Pseudomonas aeruginosa and Burkho/deria cepacia," 1996, Microbiological Reviews, pp. 539-574, vol. 60, No. 3.
Green, D.R., et al., "Mitochrondria and Apoptosis," Science, 1998, pp. 1309-1312, vol. 281.
Greinacher, A., et al., "Characterization of the structural requirements for a carbohydrate based anticoagulant with a reduced risk of inducing the immunological type of heparin-associated thrombocytopenia," Thrombosis and Haemostasis, 1995, pp. 886-892, vol. 74, No. 3.
Griffin, K.L.. et al., "2-O-Desulfated Heparin Inhibits Neutrophil Elastase-Induced HMGB-1 Secretion and Airway Inflammation," American Journal of Respiratory Cell and Molecular Biology, 2014, pp. 684-689, vol. 50, No. 4.
Groenewnegen, K.H., et al., "Mortality and Mortality-Related Factors After Hospitalization for Acute Exacerbation of COPD," Chest, 2003, pp. 459-467, vol. 124.
Guang-Xi, Z., et al., "Preparation of Low Molecular Weight Heparin Liposomal Spray Gel," Chinese Journal of Pharmaceuticals, 1998, pp. 261-265, vol. 29, No. 6 (with English Abstract).
Gulec, S. A., et al., "Treatment of Advanced Pancreatic Carcinoma with 90 Y-Clivatuzumab Tetraxetan: A Phase I Single-Dose Escalation Trial," Clin Cancer Res, 2011, pp. 4091-4100, vol. 17.
Guo, Y., et al., "Analysis of Oligosaccharides from Heparin by Reversed-Phase Ion-Pairing High-Performance Liquid Chromatography," Analytical Biochemicstry, 1988, pp. 54-62, vol. 168.
Haas, S., et al., "Heparin-induced Thrombocytopenia: Clinical Considerations of Alternative Anticoagulation with Various Glycosaminoglycans and Thrombin Inhibitors", Clin Appl Thrombosis/Hemostasis. 1999, pp. 52-59, vol. 5.
Hagihara, H., et al., "Na+/Ca2+ exchange inhibition protects the rat heart from ischemia-reperfusion injury by blocking energy-wasting processes," Am J Physiol Heart Circ Physiol, 2005, vol. 288, No. 4, H1699-H1707.
Hale, S. L., et al., "The Antianginal Agent, Ranolazine, Reduces Myocardial Infarct Size but Does Not Alter Anatomic No-Reflow or Regional Myocardial Blood Flow in Ischemia/Reperfusion in the Rabbit," Joumal of Cardiovascular Pharmacology and Therapeutics, 2008, pp. 226-232, vol. 13, No. 3.
Hale, S. L., et al., "Improved Left Ventricular Function and Reduced Necrosis After Myocardial Ischemia/Reperfusion in Rabbits Treated with Ranolazine, and Inhibitor of the Late Sodium Channel," Journal of Pharmacology Experimental Therapeutics, 2006, pp. 418-423, vol. 318, No. 1.
Hartman, M.M., "Thrombo-Embolic Phenomena in Severe Asthma," California Medicine, 1963, pp. 27-32, vol. 98, No. 1.
Harvey, J.R., et al., "Inhibition of CXCR4-Mediated Breast Cancer Metastasis: A Potential Role for Heparinoids?," Clin. Cancer Res., 2007, pp. 1562-1570, vol. 13, No. 5.
Haunstetter, A., et al., "Basic Mechanisms and Implications for Cardiovascular Diseases," Circ. Res., 1998, p. 1111-1129, vol. 82.
Hausenloy, D. J., et al., "Time to Take Myocardial Reperfusion Injury Seriously," New Engl J Med, 2008, pp. 518-520, vol. 359, No. 5.
Hecht, I., et al., "Heparin-disaccharide affects T cells: inhibition of NF-kB activation, cell migration, and modulation of intracellular signaling," Journal of Leukocyte Biology, 2004, pp. 1139-1146, vol. 75.

(56) References Cited

OTHER PUBLICATIONS

Herbert, J., et al., "Protein kinase C α expression is required for heparin inhibition of rat smooth muscle cell proliferation in vitro and in vivo," Journal of Biological Chemistry, 1996, pp. 25928-25935, vol. 271, No. 2.
Herold, B. C., et al., "Differences in the Susceptibility of Herpes Simples Virus Types 1 and 2 to Modified Heparin Compounds Suggest Serotype Differences in Viral Entiy," Journal of Virology, 1996, pp. 3461-3469.
Hinata, M., et al., "Stoichiometry of Na +—Ca2+ Exchange is 3:1 in Guinea-Pig Ventricular Myocytes," J Physiol, 2002, pp. 453-461, vol. 545, No. 2.
Holmer, E., "Low Molecular Weight Heparin," Heparin, Chemical and Biological Properties, Clinical Applications, 1989, pp. 575-595.
Hori, O., et al., "The Receptor for Advanced Glycation End Products (RAGE) is a Cellular Binding Site for Amphoterin," 1995, The Journal of Biological Chemistry, pp. 25752-25761, vol. 270, No. 43.
Hu, J., et al., "Complex Allosteric Modulation of Cardiac Muscarinic Receptors by Protamine: Potential Model for Putative Endogenous Ligands," Mol.Pharmacol., 1992, pp. 311-324, vol. 42.
Hudson, B.I., et al., "Blockade of Receptor for Advanced Glycation Endproducts: A New Target for Therapeutic Intervention in Diabetic Complications and Inflammatory Disorders," Archives of Biochemistry and Biophysics, 2003, pp. 80-88, vol. 419, No. 1.
Huebschmann, A.G., et al., "Diabetes and Advanced Glycoxidation End Products," Diabetes Care, 2006, pp. 1420-1432, vol. 29, No. 6.
Hurst, J.R., et al., "Systemic and Upper and Lower Airway Inflammation at Exacerbation of chronic Obstructive Pulmonary Disease," Am J Respir Crit Care Med, 2006, pp. 71-78, vol. 173.
Hurst, J.R., et al., "Use of Plasma Biiomarkers at Exacerbation of Chronic Obstructive Pulmonary Disease," Am J Respir Crit Care Med, 2006, pp. 867-874, vol. 174.
Huttijnen, H.J., et al., "Receptor for Advanced Glycation End Products-Binding COOR-Terminal Motif of Amphoterin Inhibits Invasive Migration and Metastasis," Cancer Research, 2002, pp. 4805-4811, vol. 62.
Im, K-I., et al., "The Free Radical Scavenger NecroX-7 Attenuates Acute Graft-versus-Host Disease via Reciprocal Regulation of Th1/Regulatory T Cells and Inhibition of HMGB1 Release," The Journal of Immunology, 2015, pp. 5223-5232, vol. 194.
Imahashi, K., et al., "Cardiac-Specific Ablation of the Na+—Ca2 Exchanger Confers Protection Against Ischemia/Reperfusion Injury," Circ Res, 2005, pp. 916-921, vol. 97.
Inserte, J., et al., "Effect of Inhibition of Na+/Ca 2+ Exchanger at the Time of Myocardial Referfusion on Hypercontracture and Cell Death," Cardiovasc Res, 2002, pp. 739-748, vol. 55.
Kang, R., et al., "HMGBI A novel Beclin 1-binding protein active in autophagy," Autophagy, 2010, pp. 1209-1211, vol. 6, No. 8.
Kanner, R.E., et al., "Lower Respiratory Illnesses Promote FEV1 Decline in Current Smokers But Not Ex-Smokers With Mild Chronic Obstructive Pulmonary Disease," Am J Respir Crit Care Med, 2001, pp. 358-364, vol. 164.
Kantarjian, H. M., et al., "High doses of cyclophosphamide, etoposide and total body irradiation followed by autologous stem cell transplantation in the management of patients with chronic myelogenous leukemia," Bone Marrow Transolant, 1994, pp. 57-61, vol. 14, No. 1. (Abstract).
Khorana, A. A., et al., "Thromboembolism in hospitalized neutropenic cancer patients" Journal Clinical Oncology, 2006, pp. 484-490, vol. 24.
Kim, J., et al., "Reactive Oxygen Species, But Not Ca2+ Overloading, Trigger pH- and Mitochondrial Permeability Transition-Dependent Death of Adult Rat Myocytes After Ischemia-Reperfusion," Am J Physiol Heart Circ Physiiol, 2006, pp. H2024-H2034, vol. 290.
Kleiman, N., et al., "Diabetes mellitus, glycoprotein IIb/IIIa blockade, and heparin: Evidence for a complex interaction in a multicenter trial," Circulation, 1998, pp. 1912-1920, vol. 97, No. 19.
Knaus, H., et al., "In vivo labeling of L-type Ca2+ Channels by Fluorescent Dihydropyridines: Evidence for a Functional, Extracellular Heparin-Binding Site," Proc Natl Acad Sci, 1992, pp. 3586-3590, vol. 89.
Koenig, A., et al., "Differential Interactions of Heparin and Heparan Sulfate Glycosaminoglycans with the Selectins," J Clin. Invest., 1993, pp. 877-889, vol. 101, No. 4.
Kohri, K., et al., "Neutrophil Elastase Induces Mucin Production by Ligand Dependent Epidermal Growth Factor Receptor Activation," Am J Physiol Lung Cell Mal Physiol, 2002, pp. L531-L540, vol. 283.
Korge, P., et al, "Phenylarsine oxide induces mitochondrial permeability transition, hypercontracture, and cardiac cell death," Am J Physiol Heart Circ Physiol, 2001, pp. H2203-H2213, vol. 280.
Koukourakis, M. , "Radiation damage and radioprotectants: new concepts in the era of molecular medicine," The British Journal of Radiology, 2012, pp. 313-330, vol. 85.
Kovacsovics, T.J., et al., "Preliminary Evidence That ODSH (2-O, 3-O Desulfated Heparin) is Safe and Enhances Count Recovery in Patients Treated with Intensive Therapy for Acute Myeloid Leukemia—Results of a Pilot Study," Blood, 2014, pp. 1-3, vol. 124, No. 5297 (abstract).
Krajewski, S., et al., "Release OfCaspase-9 From Mitochondrial During Neuronal Apoptosis and Cerebral Ischemia," Proc. Natl. Acad. Sci. USA, 1999, pp. 5752-5757, vol. 96.
Krauel, K., et al., "Heparin-induced thrombocytopenia-therapeutic concentrations of danaparoid, unlike fondaparinux and direct thrombin inhibitors, inhibit formation of platelet factor 4-heparin complexes," Journal of Thrombosis and Haemostasis, 2008, pp. 2160-2167, vol. 6.
Kubota, T., et al., "Dilated Cardiomyopathy in Transgenic Mice With Cardiac-Specific Overexpression of Tumor Necrosis Factor-α," Circulation Research, 1997, pp. 627-635, vol. 81, No. 4.
Irimura, T., et al., "Chemically Modified Heparins as Inhibitors of Heparan Sulfate Specific Endo- beta-glucuronidase (Heparanase) of Metastiatic Melanoma Cells," Biochemistry, 1986, pp. 5322-5328.
Ishii, H., et al., "Phase II Study of Gemcitabine Chemotherapy Alone for Locally Advanced Pancreatic Carcinoma: JCOG0506," Jon J Clin Oneal, 2010, pp. 573-579, vol. 40, No. 6.
Iwamoto, T., et al., "A Novel Isothiourea Derivative Selectively Inhibits the Reverse Mode of Na+—Ca2+ Exchange in Cells Expressing NCXI," J Biol Chem, 1996, pp. 13609-13615, vol. 271, No. 37.
Iwamoto, T., et al., "Phosphorylation-Dependent Regulation of Cardiac Na+—Ca2+ Exchange via Protein Kinase C," J Biol Chem, 1996, pp. 22391-22397, vol. 271, No. 23.
Jacoby, D.B., et al., "Human Eosinophil Major Basic Protein is an Endogenous Allosteric Antagonist at the Inhibitory Muscarinic M2 Receptor," Journal of Clinical Investigation, 1993, pp. 1314-1318, vol. 91.
Jaques, L.B., et al., "Intrapulmonary Heparin, A New Procedure for Anticoagulant Therapy," Lancet, 1976, pp. 1157-1161.
Jaseja, M., et al., "Novel regio- and Stereoselective Modifications of Heparin in Alkaline Solution. Nuclear Magnetic Resonance Spectroscopic Evidence," Can. J. Chem., 1989, pp. 1449-1456, vol. 67.
Jeske, W. P., et al., "Hepatin-Induced Thrombocytopenic Potential of GAG and Non-GAG-Based Anti thrombotic Agents," Clin Appl Thrombosis/Hemostasis, 1999, pp. S56-S62, vol. 5.
Johns Hopkins Medicine Health Library, "Bone Marrow Transplantation," Jul. 2017, [online][Retrieved on Jul. 24, 2017] Retrieved from the Internet < URL: http://www.hopkinsmedicine.org/healthlibrary/conditions/hematology_and_blood_disorders/bone_marrow_transplantation_85,P00086/>.
Jorneskog, G., et al., "Low Molecular Weight Heparin Seems to Improve Local Capillary Circulation and Healing of chronic Foot Ulcers in Diabetic Patients," VASA, 1993, pp. 137-142, vol. 22, No. 2.
Ju, Y.K., et al., "Hypoxia Increases Persistent Sodium Current in Rat Ventricular Myocytes," J. Physiol., 1996, pp. 337-347, vol. 497.
Juarez, J., et al., "CXCR4 antagonists mobilize childhood acute lymphoblastic leukemia cells into the peripheral blood and inhibit engraftment," Leukemia, 2007, pp. 1249-1257, vol. 21.

(56) References Cited

OTHER PUBLICATIONS

Kanabar, V., et al., "Some Structural Determinates of the Antiproleferative Effect of Heparin-Like Molecules on Human Airway Smooth Muscle," British Journal of Pharmacology, 2005, pp. 370-377, vol. 146.

Kang, R., et al., "The Receptor for Advanced Glycation End-Products (RAGE) Protects Pancreatic Tumor Cells Against Oxidative Injury," Antioxidants & Redox Signaling, 2011, pp. 2175-2184, vol. 15, No. 8.

Kang, R., et al., "Apoptosis to autophagy switch triggered by the MHC class III-encoded receptor for advanced glycation endproducts (RAGE)," Autophagy, 2011, pp. 91-93, vol. 7, No. 1.

Kang, R., et al., "The receptor for advanced glycation end products (RAGE) sustains autophagy and limits apoptosis, promoting pancreatic tumor cell survival," Cell Death and Differentiation, 2010, pp. 666-676, vol. 17.

Li, Z., et al., "Cloning of the NCX2 Isoform of the Plasma Membrane Na+—Ca2+ Exchanger," J Biol Chem, 1994, 269:17434-17439.

Libby, P., et al., "Inflammation and Atherosclerosis: Role ofC-Reactive Protein in Risk Assessment," Am J Med, 2004, pp. 9S-16S, vol. 116.

Light, P.E., et al., "Constitutively Active Adenosine Monophosphate-Activated Protein Kinase Regulates Voltage-Gated Sodium Channels in Ventricular Myocytes," Circulation, 2003, 107:1962-1965.

Lindahl, U., et al., "Generation of"Neohepatin" From *E. coli* KS Capsular Polysaccharide," J Med. Chem., 2005, pp. 349-352, vol. 48.

Liu, D., et al., "Autophagy: A Potential Mechanism for Resistance of Esophageal Squamous Cell Carcinoma to Therapy," J Formos Med Assoc., 2010, pp. 775-776, vol. 109, No. 11.

Liu, D., et al., "Inhibition of autophagy by 3-MA potentiates cisplatin-induced apoptosis in esophageal squamous cell carcinoma cells," Med Oncol., 2011, pp. 105-111, vol. 28.

Liu, L., et al., "DAMP-mediated autophagy contributes to drug resistance," Autophagy, 2011, pp. 112-114, vol. 7, No. 1.

Loo, B., et al., "Heparin/Heparan Sulfate Domains in Binding and Signaling of Fibroblast Growth Factor 8b," The Journal of Biological Chemistry, 2002, pp. 32616-32623, vol. 277, No. 36.

Lopez, M., et al., "Medical management of the acute radiation syndrome," Reports of Practical Oncology and Radiotherapy, 2011, pp. 138-146, vol. 16.

Lorenz, R., et al., "Platelet Factor 4 (PF 4) in Septicaemia," Infection, 1988, pp. 273-176, vol. 16.

Ludwig, R., "Therapeutic Use of Heparin beyond Anticoagulation," Current Drug Discovery Technologies, 2009, pp. 281-289, vol. 6.

Man, S.F.P., et al., "Effects of Corticosteroids on Systemic Inflammation in Chronic Obstructive Pulmonary Disease," Proc Am Thorac Soc, 2005, pp. 78-82, vol. 2.

Marcus, S., et al., "ODSH, a heparin derivative, enhances the efficacy of gemcitabine in a refractory human pancreatic tumor xenograph model," Presentation Abstract, Apr. 3, 2012, AACR Annual Meeting, Abstract No. 3698.

Matsuda, T., et al., "SEA0400, a Novel and Selective Inhibitor of the Na+—Ca2+ Exchanger, Attenuates Reperfusion Injury in the In Vitro and In Vivo Cerebral Ischemic Models," J Pharmacol Exp Ther, 2001, 298:249-256.

Maulik, N., et al., "Oxidative Stress Developed During the Reperfusion of Ischemic Myocardium Induces Apoptosis," Free Rad. Biol. Med., 1998, pp. 869-875, vol. 24.

Mccrory, D.C., et al., "Management of Acute Exacerbations of COPD," Chest, 2001, pp. 1190-1209, vol. 119.

McKeehan, W.L., et al., "Requirement for Anticoagulant Heparan Sulfate in the Fibroblast Growth Factor Receptor Complex," The Journal of Biological Chemistry, 1999, pp. 21511-21514, vol. 274, No. 31.

Lacinova, L., et al., "Ca2+ Channel Modulating Effects of Heparin in Mammalian Cardiac Myocytes," J Physiol, 1993, pp. 181-201, vol. 465.

Ladilov, Y.V., et al., "Protection of Reoxyenated Cardiomyocytes Against Hypercontracture by Inhibition of Na+/H+ Exchange," Am J Physiol, 1995, pp. HI531-HI539.

Lambert, M. P., et al., "Platelet factor 4 is a negative autocrine in vivo regulator ofmegakaryopoiesis: clinical and therapeutic implications," Blood, 2007, pp. 1153-1160, vol. 110, No. 4.

Lambert, M. P., et al., "The Role of Platelet Factor 4 in Radiation-Induced Thrombocytopenia," Int. J Radiation Oncology Biol. Phys., 2011, pp. 1533-1540, vol. 80, No. 5.

Lambert, M., et al., "2-0, 3-0-Desulfated Heparin (ODSH) Mitigates Chemotherapy-Induced Thrombocytopenia (CIT) by Blocking the Abstract Negative Paracrine Effect of Platelet Factor 4 (PF4) on Megakaryopoiesis," Blood, 2012, vol. 120, Abstract 386.

Lambert, M. P., et al., "Platelet factor 4 platelet levels are inversely correlated with steady-state platelet counts and with platelet transfusion needs in pediatric leukemia patents," International Society on Thrombosis and Haemostasis, 2012, pp. 1442-1446, vol. 10, No. 7.

Lapierre, F., et al., "Chemical modifications of heparin that diminish its anticoagulant but preserve its heparanase-inhibitory, angiostatic, anti-tumor and antimetastatic properties," Glycobiology, 1996, pp. 355-366, vol. 6, No. 3.

Le Grand, B., et al., "Sodium Late Channel Blockers in Ischemia Reperfusion: Is The Bullet Magic?" J Med Chem, 2008, pp. 3856-3866, vol. 51.

Lee, J., et al., "The Changing Landscape of Ischaemic Brain Injury Mechanisms," Nature, 1999, pp. A7-A14, vol. 399 (Supplement).

Levine, B., et al., "Elevated Circulating Levels of Tumor Necrosis Factor in Severe Chronic Heart Failure," The New England Journal of Medicine, 1990, pp. 236-241.

Levy, L., et al., "Chemical and Pharmacological Studies on N-Sulfated Heparin", Proc. Soc. Exp. Biol. and Med., 1962, 109:901-905.

Levy, L., et al., "Heparin-Induced Thrombocytopenia, a Prothrombotic Disease," Hematology/Oncology Clinics of North America, 2007, pp. 65-88, vol. 21.

Li, F., et al., "Activation of Connexin-43 Hemichannels Can Elevate [Ca2+] and [Na+] in Rabbit Ventricular Myocytes During Metabolic Inhibition," J Mal Cell Cardiol, 2001, 33:2145-2155.

Li, S., et al., "Does enoxaparin interfere with HMGB1 signaling after TBI? A potential mechanism for reduced cerebral edema and neurologic recovery," J Trauma Acute Care Surg., 2016, pp. 381-389, vol. 80, No. 3.

Li, S., et al., "Enoxaparin ameliorates postYtraumatic brain injury edema and neurologic recovery, reducing cerebral leukocyte endothelial interactions and vessel permeability in vivo," Journal of Trauma and Acute Care Surgery, 2015, pp. 78-84, vol. 79, No. 1.

Mulloy, B., et al., "Conformation and dynamics of heparin and heparan sulfate," Glycobiology, 2000, pp. 1147-1156, vol. 10, No. 11.

Myint, K., et al., "RAGE Control of Diabetic Nephropathy in a Mouse Model-Effects of RAGE Gene Disruption and Administration of Low-Molecular Weight Heparin," Diabetes, 2006, pp. 2510-2522, vol. 55.

Nadel, J.A., "Role of Neutrophil Elastase in Hypersecretion During COPD Exacerbations, and Proposed Therapies," Chest, 2000, pp. 386S-389S, vol. 117 (Suppl.).

Nagasawa, K., et al., "Hydrophobic-Interaction Chromatography of Glycosaminoglycuronans: The Contribution on N-Acetyl Groups in Heparin and Heparan Sulfate to the Affinity for Hydrophobic Gels, and Variety of Molecular Species in Beef-Kidney Heparan Sulfate," Carb. Res., 1983, 111:273-281.

Nakagawa, T., et al. "Cyclophilin D-Dependent Mitochondrial Permeability Transition Regulates Some Necrotic But Not Apoptotic Cell Death," Nature, 2005, pp. 652-658.

Narula, J., et al., "Apoptosis in Myocytes in End-Stage Heart Failure," New England J Med., 1996, pp. 1182-1189, vol. 335.

Nemeth, K., et al., "Suppression of Ca2+ Influx by Unfractionated Heparin in Non-Excitable Intact Cells Via Multiple Mechanisms," Biochem Pharmacol 69, 2005, pp. 929-940.

Netelenbos, T., et al., "Proteoglycans guide SDF-1-induced migration of hematopoietic progenitor cells," Journal of Leukocyte Biology, 2002, pp. 353-362, vol. 72.

Nicoll, D.A., et al., "Cloning of a Third Mammalian Na+—Ca2+ Exchanger, NCX3," J Biol Chem, 1996, pp. 24914-24921, vol. 271.

(56) References Cited

OTHER PUBLICATIONS

Nicoll, D.A., et al., "Molecular Cloning and Functional Expression of the Cardiac Sarcolemmal Na+—Ca2+ Exchanger," Science, 1990, pp. 562-565.
Niers, T., et al., "Mechanisms of heparin induced anti-cancer activity in experimental cancer models," Critical Review in Oncology Hematology, 2007, pp. 195-207, vol. 61.
Niewoehner, D.E., et al., "Effect of Systemic Glucocorticoids on Exacerbations of Chronic Obstructive Pulmonary Disease," N Engl J Med, 1999, pp. 1941-1947, vol. 340.
Niewoehner, D.E., "The Impact of Severe Exacerbations on Quality of Life and the Clinical Course of Chronic Obstructive Pulmonary Disease," Am J Med, 2006, pp. S38-S45, vol. 119.
Noble, D., et al., "Late Sodium Current in the Pathophysiology of Cardiovascular Disease: Consequences of SodiumCalcium Overload," Heart, 2006, vol. 92 (Suppl 4).
Nunez, G., et al., "The Bcl-2 Family of Proteins: Regulators of Cell Death and Survival," Trends in Cell Biology, 1994, pp. 399-403, vol. 4.
O'Farrell, F., et al. "Kinetic Study of the Inhibition of CK2 by Heparin Fragments of Different Length," Biochem Biophys Acta, 1999, pp. 68-75.
McLaurin, J., et al., "Effect of Amino-Acid Substitutions on Alzheimer's Amloid-beta Peptide-Glycosaminoglycan Interactions," Eur. J Biochem., 2000, pp. 6353-6361, vol. 267.
McLeod, R.S., et al., "Subcutaneous Heparin Versus Low-Molecular-Weight Heparin as Thromboprophylaxis in Patients Undergoing Colorectal Surgery" Annals of Surgery, 2001, vol. 233, No. 3, pp. 438-444.
Meirow, D., et al., "Prevention of Severe Menorrhagia in Oncology Patients With Treatment-Induced Thrombocytopenia by Luteinizing Hormone-Releasing Hormone Agonist and Depo-Medroxyprogesterone Acetate," Cancer, 2006, pp. 1634-1641, vol. 107, No. 7.
Meldrum, D.R., et al., "Hemorrhage Activates Myocardial NFKB and Increases TNF-a in the Heart, " J Mal. Cell. Cardiol., 1997, pp. 2849-2854, vol. 29.
Memorial Sloan Kettering Cancer Center, "Total Body Irradiation," Oct. 2010, [online][Retrieved on Jun. 27, 2017] Retrieved from the Internet <URL: https://www.mskcc.org/cancer-care/patient-education/total-body-irradiation>.
Merchant, Z. M., et al., "Structure of heparin-derived tetrasaccharides," Biochem. J., 1985, pp. 369-377, vol. 229.
Messmore, H. L., et al., "Benefit-Risk Assessment of Treatments for Heparin-Induced Thrombocytopenia", Drug Safety, 2003 pp. 625-641, vol. 26, No. 9.
Miah, M.A., et al., "CISH is induced during DC development and regulates DC-mediated CTL activation," Eur. J. Immunol., 2012, pp. 58-68, vol. 42. No. 1.
Milev, P., et al., "High Affinity Binding and Overlapping Localization of Neurocan and Phosphacan/Protein-Tyrosine Phosphatase-ζ/βWth Tenascin-R, Amphoterin, and the Heparin-Binding Growth-Associated Molecule," The Journal of Biological Chemistry, 1998, pp. 6998-7005, vol. 273, No. 12.
Minette, P.A.H., et al., "A Muscarinic Agonist Inhibits Reflex Brochoconstriction in Normal But Not in Asthmatic Subjects," J.Appl.Physiol., 1989, vol. 67, No. 6, pp. 2461-2465.
Mocco, J., et al., "O-desulfated heparin improves outcome after rat cerebral ischemia/reperfusion injury," Neurosurgery, 2007, pp. 1297-1304, vol. 61. 1297-1303.
Mold, C., et al., "Protection from *Streptococcus pneumoniae* Infection by C-Reactive Protein and Natural Antibody Requires Complement But Not Fcy Receptors," J Immunol, 2002, pp. 6375-6381, vol. 168.
Moreira, R., et al., "Design, Synthesis, and Enzymatic Evaluation of N1-Acyloxyalkyl- and N1-Oxazolidin-2,4-dion-5-yl-Substituted beta-lactams as Novel Inhibitors of Human Leukocyte Elastase," J. Med. Chem., 2005, pp. 4861-4870, vol. 48.
Morigi, M., et al., "Leukocyte-endothelial Interaction is Augmented by High Glucose Concentrations and Hyperglycemia in a NF-kB-dependent Fashion," J Clin. Invest., 1998, pp. 1905-1915, vol. 101, No. 9.
Mousa, S., et al., "Anti-metastatic effect of a non-anticoagulant low-molecular-weight heparan versus the standard low-molecular-weight heparin, enoxaparin," Thromb. Haemost., 2006, pp. 816-821, vol. 96.
Piper, H.M., et al., "The First Minutes of Reperfusion: A Window of Opportunity for Cardioprotection," Cardiovascular Research, 2004, pp. 365-371.
Poole, P., et al., "Case management may reduce length of hospital stay in patients with recurrent admissions for chronic obstructive pulmonary disease," Respirology, 2001, pp. 37-42, vol. 6.
Poruk, K. E., et al., "Serum Platelet Factor 4 is an Independent Predictor of Survival of Venous Thromboembolism in Patients with Pancreatic Adenocarcinoma," Cancer Epidemiology Biomarkers Prevention, 2010, pp. 2605-2610, vol. 19 No. 10.
Qiu, Y., et al., "Biopsy Neutrophilia, Neutrophil chemokine and Receptor Gene Expression in Severe Exacerbations of Chronic Obtructive Pulmonary Disease," Am J Respir Crit Care Med, 2003, pp. 968-975, vol. 168.
Quinn, F.R., et al.,"Myocardial Infarction Causes Increased Expression But Decreased Activity of the Myocardial Na+—Ca2+ Exchanger in the Rabbit," J Physiol, 2003, pp. 229-242.
Rabe, K.F., et al., "Global Strategy for the Diagnosis, Management, and Prevention of Chronic Obstructive Pulmonary Disease," Am J Respir Grit Care Med, 2007, pp. 532-555, vol. 176.
Ramamurthy, N., et al., "Determination of Low-Molecular-Weight Heparins and Their Binding to Protamine and a Protamine Analog Using Polyion-Sensitive Membrane Electrodes," Analytical Biochemistry, 1999, pp. 116-124, vol. 266.
Ramamurthy, N., et al., "Improved Protamine-Sensitive Membrane Electrode for Monitoring Heparin Concentrations in Whole Blood Via Protamine Titration," Clinical Chemistry, 1998, pp. 606-613, vol. 44, No. 3.
Ramasamy, R., et al., "Advanced Glycation End Products and RAGE: A Common Thread in Aging, Diabetes, Neurodeneration, and Inflammation," Glycobiology, 2005, pp. 16R-28R, vol. 15, No. 7.
Ramsey, S.D., et al., "The Burden of Illness and Economic Evaluation for COPD," Eur Respir J, 2003, pp. 29S-35S, vol. 21.
Rao, N.V., et al, "Sulfated Polysaccharides Prevent Human Leukocyte Elastase-Induced Lung Injury and Emphysema in Hamsters," Am. Rev. Respir. Dis, 1990, pp. 407-412, vol. 142.
Rao, N. V., et al., "Low anticoagulant heparin targets multiple sites of inflammation, suppresses heparin-induced thrombocytopenia, and inhibits interaction of RAGE with its ligands," Am J Physiol Cell Physiol, 2010, pp. C97-C110, vol. 299.
Rauvala, H., et al., "The Adhesive and Neurite-Promoting Molecule p30: Analysis of the Amino-Terminal Sequence and Production of Antipeptide Antibodies that Detect p30 at the Surface ofNeuroblastoma Cells and of Brain Neurons," The Journal of Cell Biology, 1988, pp. 2293-2305, vol. 107, No. 6.
Redini, F., et al., "Influence of Heparin Fragments on the Biological Activities of Elastase(s) and α1 Proteinase Inhibitor," Biochem. Pharmacol., 1988, pp. 4257-5261.
Redinin, F., et al., "Inhibition of Leukocyte Elastase by Heparin and its Derivatives", Biochem. J., 1988, pp. 515-519.
Olivetti, G., et al., "Acute Myocardial Infarction in Humans is Associated With Activation of Programmed Myocyte Cell Death in the Surviving Portion of the Heart," J Mal. Cell Cardiol., 1994, pp. 2005-2016, vol. 28.
Orlova, V.V., et al., "A Novel Pathway ofHMGBI-Mediated Inflammatory Cell Recruitment that Requires Mac-1 Integrin," The EMBO Journal, 2007, pp. 1129-1139, vol. 26, No. 4.
Papi, A., et al., "Infections and Airway Inflammation in Chronic Obstructive Pulmonary Disease Severe Exacerbations," Am J Respir Crit Care Med, 2006, pp. 1114-1121, vol. 173.
Paringenix, "Efficacy & Safety of ODSH (2-0, 3-0 Desulfated Heparin) in Patients With Metastatic Pancreatic Cancer Treated With Gemcitabine & Abraxane (PGPCI)," Oct. 13, 2011,

(56) References Cited

OTHER PUBLICATIONS

[online][retrieved on Jul. 16, 2013] Retrieved at <URL:https://clinicaltrials.gov/ct2/show/NCT01461915>.

Pasotti, C., et al., "Protective Effect of a Duodenal Heparinoid on the Mouse Subjected to Panirradiation with Letal Doses," Gazz. Intern. Med. Chir., 1965, pp. 241-249, vol. 70, No. 3. (with machine translation).

Peled, A., et al., "Role of CXCR4 in the Pathogenesis of Acute Myeloid Leukemia," Theranostics, 2013, pp. 34-39, vol. 3, No. 1.

Perera, W.R., et al., "Inflammatory Changes, Recovery and Recurrence at COPD Exacerbation," Eur Respir J, 2007, pp. 527-534, vol. 29.

Peter, K., et al., "Heparin Inhibits Ligand Binding to the Leukocyte Integrin Mac-1 (CD11/CD18)," Journal of the American Heart Association, 1999, pp. 1533-1539, vol. 100.

Petersen, L.C., et al., "The Effect of Complex Formation With Polyanions on the Redox Properties of Cytochrome C," Biochem. J, 1980, pp. 687-693, vol. 2.

Peterson, J. E., et al., "VEGF, PF4 and PDGF are elevated in platelets of colorectal cancer patients," Angiogenesis, 2012, pp. 265-273, vol. 15.

Petitou, M., et al., "Synthesis of Heparin Fragments. A Chemical Synthesis of the Pentasaccharide O-(2-Deoxy-2-Sulfamido 6-O-Sulfo-α-D-Glucopyranosyl)-(1→4)-O-(β-D-Glucopyranosyluronic Acid)-(1→4)-O-(2-Deoxy-2-Sulfamido-3,6 DI-O-Sulfo-α-D-Gluco-Pyranosyl)-(1→4)-O-(2-O-Sulfo-α-L-Idopyranosyluronic Acid)-(1→4)-2-Deoxy-2-Sulfamido-6-O-Sulfo-D-Glucopyranose Decasodium Salt, A Heparin Fragment Having High Affinity for Antithrombin III," Carbohydrate Research, 1986, pp. 221-236, vol. 147. Antithrombin III. Carbohydrate Research, 1986, pp. 221-236 vol. 147.

Petri, B., et al., "Molecular Events During Leukocyte Diapedesis," FEBS Journal, 2006, pp. 4399-4406, vol. 273.

Pinto-Plata, V.M., et al., "C-Reactive Protein in Patients with COPD, Control Smokers and Non-Smokers," Thorax, 2006, pp. 23-28, vol. 61.

Piot, C. A., et al., "Ischemic Preconditioning Decreases Apoptosis in Rat Hearts In Vivo," Circulation, 1997, pp. 1598-1604, vol. 96, No. 5.

Piot, C., et al., "Effect of Cyclosporine on Reperfusion Injury in Acute Myocardial Infarction," New Engl J Med, 2008, pp. 473-481, vol. 359, No. 5.

Sharma, L., et al., "Partially-desulfated heparin improves survival in Pseudomonas pneumonia by enhancing bacterial clearance and ameliorating lung injury," Journal of Immunotoxicology, 2014, pp. 260-267, vol. 11. No. 3.

Sheridan, D., et al., "A Diagnostic Test for Heparin-Induced Thrombocytopenia," Blood, 1986, pp. 27-30, vol. 67, No. 1.

Shinjo, S.K., et al., "Heparin and Heparan Sulfate Disaccharides Bind to the Exchanger Inhibitor Peptide Region of Na+—Ca2+ Exchanger and Reduce the Cytosolic Calcium of Smooth Muscle Cell Lines," J Biol Chem, 2002, pp. 48227-48233.

Siegmund, B., et al., "Temporary Contractile Blockade Prevents Hypercontracture in Anoxic-Reoxygenated Cardiomyocytes," Am J Physiol, 1991, pp. H426-H635.

Sigal, D., et al., "2-0, 3-0 Desulfated Heparin (ODSH) May Mitigate Chemotherapy-Induced Thrombocytopenia and Neutropenia in Patients Treated with Combination Gemcitabine (G)/Nab-Paclitaxel (A), a Myelosuppressive Chemotherapy Regimen," BLOOD, 2012, p. 4 723 (Abstract), vol. 120, No. 21.

Sims, G. P., et al., "HMGBI and RAGE in Inflammation and Cancer," Annu. Rev. Immunol., 2010, pp. 367-388, vol. 28.

Sin, D., et al., Effects of Fluticasone on Systemic Markers of Inflammation in Chronic Obstructive Pulmonary Disease, Am. J. Respir. Crit. Care Med., 2004, pp. 760-765, vol. 170.

Sommerhoff, C.P., et al., "Neutrophil Elastase and Cathepsin G Stimulate Secretion From cultured Bovine Airway Gland Serous Cells," J Clin Invest, 1990, pp. 682-689, vol. 85.

Song, Y., et al., "Blocking Late Sodium Current Reduces Hydrogen Peroxide-Induced Arrhythmogenic Activity and Contractile Dysfunction," J Pharmacol Exp Ther, 2006, pp. 214-222.

Sparvero, L. J., et al., "RAGE (Receptor for Advanced Glycation Endproducts), RAGE Ligands, and their role in Cancer and Inflammation," Journal of Translational Medicine, 2009, vol. 7, No. 1, 21 Pages.

Spencer, S., et al., "Time Course of Recovery of Health Status Following an Infective Exacerbation of Chronic Bronchitis," Thorax, 2003, pp. 589-593, vol. 58.

Spencer, S., et al., "Impact of Preventing Exacerbations on Deterioration of Health Status in COPD," Eur Respir J., 2004, pp. 698-702, vol. 23.

Sperandio, M., "Selectins and Glycosyltransferases in Leukocyte Rolling in vivo," FEBS Journal, 2006, pp. 4377-4389, vol. 273.

Srikrishna, G., et al., "Two Proteins Modulating Transendothelial Migration of Leukocytes Recognize Novel Carboxylated Glycans on Endothelial Cells," The Journal of Immunology, 2001, pp. 4678-4688, vol. 166.

Srikrishna, G., et al., "N-Glycans on the Receptor for Advanced Glycation End Products Influence Amphoterin Binding and Neurite Outgrowth," Journal of Neurochemistry, 2002, pp. 998-1008, vol. 80.

Staat, P., et al., "Postconditioning the Human Heart," Circulation, 2005, pp. 2143-2148.

Reed, J.C., "Cytochrome c: Can't Live Wth It—Can't Live Without It," Cell, 1997, pp. 559, 562, vol. 91.

Rej, R., et al., "Importance for Blood Anticoagulant Activity of a 2-Sulfate Group on L-Iduronic Acid Residues in Heparin," Thrombosis and Hemotosis, 1989, 61(3) p. 540.

Rej, R., et al., "Base-Catalyzed Conversion of the α-L-Iduronic Acid 2-Sulfate Unit of Heparin Into a Unit of α-L-galacturonic Acid, and Related Reactions," Carbohydrate Research, 1990. vol. 200, pp. 437-447.

Rivera, G. K., et al., "Effectiveness of Intensified Rotational Combination Chemotherapy for Late Hematologic Relapse of Childhood Acute Lymphoblastic Leukemia," Blood, 1996, pp. 831-837, vol. 88, No. 3.

Robinson, M.J., et al., "The S100 Family Heterodimer, MRP-8/14, Binds with High Affinity to Heparin and Heparan Sulfate Glycosaminoglycans on Endothelial Cells," The Journal of Biological Chemistry, 2002, pp. 3658-3665, vol. 277, No. 5.

Rodrigo, G.C., et al., "Role of Mitochondrial Re-Energization and Ca2+Influx in Reperfusion Injury of Metabolically Inhibited Cardiac Myocytes," Cardiovascular Research, 2005, 67: 291-300.

Rusnati, M., et al., "Biotechnological Engineering ofHeparin/Heparan Sulphate: A Novel Area of Multi-Target Drug Discovery," Current Pharmaceutical Design, 2005, pp. 2489-2499.

Sache, E., et al., "Partially N-Desulfated Heparin as a Non-Anticoagulant Heparin: Some Physico-Chemical and Biological Properties," Thrombosis Research, 1989, pp. 247-258, vol. 55, No. 2.

Saetta, M., et al., "Cellular and Structural Bases of Chronic Obstructive Pulmonary Disease," Am J Respir Crit Care Med, 2001, pp. 1304-1309, vol. 163.

Salmivirta, M., et al., "Neurite Growth-Promoting Protein (Amphoterin, p30) Bins Syndecan," Experimental Cell Research, 1992, pp. 444-451, vol. 200.

Saraste, A., et al., "Apoptosis in Human Myocardial Infarction," Circulation, 1997, pp. 320-323, vol. 95.

Schafer, C., et al., "Importance of Bicarbonate Transport for Protection of Cardiomyocytes Against Reoxygenation Injury," Am J Physiol Heart Circ Physiol, 2000, pp. HI457-HI463.

Schreibmayer, W., et al., "A Mechanistic Interpretation of the Action of Toxin II From Anemonia Sulcata on the Cardiac Sodium Channel," Biochim Biophys Acta, 1987, pp. 273-282.

Seemungal, T.A.R., et al., "Effect of Exacerbation on Quality of Life in Patients With Chronic Obstructive Pulmonary Disease," Am J Respir Crit Care Med, 1998, pp. 1418-1422, vol. 157.

Serjeant, E.P., "Potentiometry and Potentiometric Titrations," Chemical Analysis, 1984, pp. 363-364, vol. 69. [Book].

Shah, M., et al., 2010 "Random assignment multicenter phase II study of modified docetaxel, cisplatin, fluorouracil (mDCF) versus DCF with growth factor support (GCSF) in metastatic

(56) References Cited

OTHER PUBLICATIONS gastroesophageal adenocarcinoma (GE)," Journal Clinical Oncology, 2010, vol. 28, No. 15, Supp:4014.
Sharma, L., et al., "ODSH Improves Bacterial Clearance and Survival in Pseudomonas Aeruginosa Pneumonia," Free Radical Biological and Medicine, 2012, p. S59.
Van Doormaal, F. F., et al., "Randomized Trial of the Effect of the Low Molecular Weight Heparin Nadroparin on Survival in Patients With Cancer," Journal of Clinical Oncology, 2011, pp. 2071-2076, vol. 29, No. 15.
Vinten-Johansen, J., "Involvement of Neutrophils in the Pathogenesis of Lethal Myocardial Reperfusion Injury," Cardiovasc Res, 2004, pp. 481-497.
Von Hoff, D.D., et al., "SPARC correlation with response to gemcitabine (G) plus nab-placitaxel (nab-P) in patients with advanced metastatic pancreatic cancer: A phase I/II study," Journal of Clinical Oncology, 2009, vol. 27, No. 15S, p. 4525, abstract.
Von Hoff, D. D., et al., "Gemcitabine Plus nab-Paclitaxel is an Active Regimen in Patients Wrth Advanced Pancreatic Cancer A Phase I/II Trial," Journal of Clinical Oncology, 2011, pp. 4548-4554, vol. 29. No. 34.
Von Harsdorf, R., et al., "Signaling Pathways in Reactive Oxygen Species-Induced Cardiomyocyte Apoptosis," Circulation, 1999, pp. 2934-2941, vol. 99, No. 22.
Wagner, S., et al., "Na+—Ca2+ Exchanger Overexpression Predisposes to Reactive Oxygen Species-Induced Injury," Cardiovasc Res, 2003, pp. 404-412.
Walenga, J. M., et al., "Biochemical and Pharmacologic Rationale for the Development of a Synthetic Heparin Pentasaccharide," Thrombosis Research, 1997, pp. 1-36, vol. 86, No. 1.
Walenga, J. M., et al., "Decreased Prevalence of Heparin-Induced Thrombocytopenia with Low-Molecular-Weight Heparin and Related Drugs" Seminars in Thrombosis and Hemostasis, 2004, pp. 69-80, vol. 30, Supplement 1.
Walenga, J. M., et al., "Fondaparinux: A Synthetic Heparin Pentasaccharide as a New Antithrombotic Agent," Expert Opin. Investig. Drugs, 2002, pp. 397-407, vol. 11.
Walenga, J. M., et al., "Heparin-induced Thrombocytopenia, Paradoxical Thromboembolism, and Other Adverse Effects of Heparin-Type Therapy," Hematology/Oncology Clinics of North America, 2003, pp. 259-282, vol. 17.
Walenga, J. M., et al., "Mechanisms of Venous and Arterial Thrombosis in Heparin-Induced Thrombocytopenia," Journal of Thrombosis and Thrombolysis, 2000, pp. S13-S20, vol. 10.
Walenga, J. M., et al., "Newer Insights on the Mechanism of Heparin-Induced Thrombocytopenia," Seminars in Thrombosis and Hemostasis, 2004, pp. 57-67, vol. 30, Supplement 1.
Walenga, J. M., et al., "Relative Heparin-Induced Thrombocytopenic Potential of Low Molecular Weight Hepatins and New Antithrombotic Agents," Clin Appl Thrombosis/Hemostasis, 1996, pp. S21-S27, vol. 2.
Walenga, J. M., et al., "Vascular Damage Correlates Between Heparin-Induced Thrombocytopenia and the Antiphospholipid Syndrome," Clin Appl Thrombosis/Hemostasis, 1999, pp. 576-S84, vol. 5.
Wang, Y.J., et al., "Review of Excipients and pH's for Parenteral Products Used in the United States," J Parent. Drug Assn., 1980, pp. 452-462, vol. 34, No. 6.
Stevenson, N.J., et al., "Lung Mechanics and Dyspnea During Exacerbations of Chronic Obstructive Pulmonary Disease," Am J Respir Crit Care Med. 2005, pp. 1510-1516, vol. 172.
Stringer, S. E., et al., "Specific Binding of the Chemokine Platelet Factor 4 to Heparan Sulfate," The Journal of Biological Chemistry, 1997, pp. 20508-20514, vol. 272, No. 33.
Suci, P.A., et al., "Investigation of Ciprofloxacin Penetration into Pseudomonas aeruginosa Biofilms," Antimicrobial Agents and Chemotherapy, 1994, pp. 2125-2133, vol. 38, No. 9.
Sullivan, S.D., et al., "The Economic Burden of COPD," Chest, 2000, pp. 5-9, vol. 117.

Sun, H., et al., "Hypoxic Postconditioning Reduces Cardiomyocyte Loss by Inhibiting ROS Generation and Intracellular Ca2+ Overload," Am J Physiol Heart Circ Physiol, 2005, pp. H1900-H1908.
Takazakura, E., et al., "1425. A New Therapeutic Method of Diabetic Gangrene: Results in 10 Cases With continuous IntraArterial Infusion of Prostaglandin E1, Insulin and Heparin," Diabetes Research and Clinical Practice, 1985, pp. S545-S546, No Suppl.
Tang, D., et al., "High-Mobility Group Box 1, Oxidative Stress, and Disease," Antioxidants & Redox Signaling, 2011, pp. 1315-1335, vol. 14, No. 7.
Tang, D., et al., "Endogenous HMGBI regulates autophagy," J. Cell Biol., 2010, pp. 881-892, vol. 190, No. 5.
Tang, D., et al., "High-mobility Group Box 1 [HMGBI] and Cancer," Biochimica et Biophysica Acta, 2010, pp. 131-140, vol. 1799, No. 1.
Tang, D., et al., "The redox protein HMGBI regulates cell death and survival in cancer treatment," Autophagy, 2010, pp. 1181-1183, vol. 6, No. 8.
Tani, N., et al., "Abstract 4175: Anticancer effects of heparin in the experimental metastasis of the pancreatic cancer model with enhanced potency of gemcitabine," Cancer Research, 2010, vol. 70, No. 8, Supp. 1.
Thourani, V. H., et al., "Nonanticoagulant heparin inhibits NF-κB-activation and attenuates myocardial reperfusion injury," American Journal of Physiology, 2000, pp. H2084-H2093, vol. 278, No. 6.
Trybala, E., et al., "Interaction Between Pseudorabies Virus and Heparin/Heparan Sulfate," The Journal of Biological Chemistry, 1998, pp. 5047-5052, vol. 273, No. 9.
Tyrrell, D.J., et al., "Therapeutic Uses of Heparin Beyond Its Traditional Role as an Anticoagulant," Trends Pharmacol Sci., 1995, pp. 198-204, vol. 16, No. 6.
U.S. Department of Health and Human Services, Food and Drug Administration, Guidance for Industry, "Animal Models—Essential Elements to Address Efficacy Under the Animal Rule," Jan. 2009.
Van Der Pijl, J.W., et al., "Effect of Danaparoid Sodium on Hard Exudates in Diabetic Retinopathy," The Lancet, 1997, pp. 1743-1745, vol. 350, No. 9093.
Van Deventer, H. W., et al., "Clinical Course of Thrombocytopenia in Patients Treated With Imatinib Mesylate for Accelerated Phase Chronic Myelogenous Leukemia," Am. J. Hem., 2002, pp. 184-190, vol. 71.
Yan, S.F., et al., "Glycation, Inflammation, and RAGE: A Scaffold for the Macrovascular Complications of Diabetes and Beyond," Circulation Research, 2003, pp. 1159-1169, vol. 93.
Yang, S., et al., "Pancreatic cancers require autophagy for tumor growth," Genes & Development, 2011, pp. 717-729, vol. 25.
Yao, A., et al., "Effects of Overexpression of the Na+—Ca2+ Exchanger on [Ca2+]i Transients in Murine Ventricular Myocytes," Circ Res, 1998, pp. 657-665.
Ye, J. Y., et al., "Platelet-derived growth factor enhances platelet recovery in a murine model of radiation-induced thrombocytopenia and reduces apoptosis in megakaryocytes via its receptors and the P13-k/Akt pathway," Haematologica, 2010, pp. 745-1753, vol. 95, No. 1.
Yellon, D.M., et al., "Myocardial Reperfusion Injury," N Engl J Med, 2007, pp. 1121-1135, vol. 357.
Zatta, A.J., et al., "Infarct-Sparing Effect of Myocardial Postconditioning is Dependent on Protein Kinase C Signalling," Cardiovasc Res, 2006, pp. 315-324, vol. 70.
Zautner, A.E., et al., "N- and 6-O-Sulfated Heparan Sulfates Mediate Internalization ofCoxsackievirus B3 Variant PD into CHO-KI Cells," Journal of Virology, 2006, pp. 6629-6636, vol. 80, No. 13.
Zhang, X.Q., et al., "Ranolazine Inhibits an Oxidative Stress-Induced Increase in Myocyte Sodium and Calcium Loading During Simulated-Demand Ischemia," J Cardiovasc. Pharmacol., 2008, pp. 443-449, vol. 51, No. 5.
Zhang, S., et al., "Heparin-induced leukocytosis requires 6-O-sulfatiion and is caused by blockade of selectin- and CXCL12 protein-mediated leukocyte trafficking in mice," J. Biol. Chem. 22, 2011, pp. 5542-5543, vol. 287, No. 8.
Zhang, Y., et al., "CXCR4 inhibitors selectively eliminate CXCR4-expressing human acute myeloid leukemia cells in NOG mouse model," Cell Death and Diseases, 2012, vol. 3, No. 10, e396.

(56) References Cited

OTHER PUBLICATIONS

Zhao, Z., et al., "Inhibition of Myocardial Injury by Ischemic Postconditionig During Reperfusion: Comparison with Ischemic Preconditioning," Am J Physiol Heart Circ Physiol, 2003, pp. H579-H588.

Zou, H., et al., "Apaf-1, a Human Protein Homologous to C. elegans CED-4, Participates in Cytochrome Cdependent Activation of Caspase-3," Cell, 1997, pp. 405-413, vol. 90.

Zweier, J.L., et al., "Direct Measurement of Pree Radical Generation Following Reperfusion O flschemic Myocardium," Proc Natl Acad Sci USA, 1987, pp. 1404-1407.

Wang, C., et al., "TNF- and Cancer THerapy Induced Apoptosis:Potential by Inhibition of NF-κB," Science, 1996, pp. 784-789.

Wang, L., et al., "Heparin's Anti-Inflammatory Effects Require Glucosamine 6-0-sulfation and are Mediated by Blockade of L- and P-selectins," The Journal of Clinics Investigation, 2002, pp. 127-136, vol. 110. ofL-and P-Selections, The Journal ofClinicalInvestigation, 2002, pp. 127-136, vol. 110.

Wang, J.-G., et al., "N-Desulfated Non-Anticoagulant Heparin Inhibits Leukocyte Adhesion and Transmigration in vitro and Attenuates Acute Peritonitis and Ischemia and Reperfusion Injury In Vivo," Inflamm. Res., 2002, pp. 435-443, vol. 51.

Wang, Y., et al., "Heparin-Paclitaxel Conjugates as Drug Delivery System: Synthesis, Self-Assembly Property, Drug Release, and Antitumor Activity," Bioconjug. Chem., 2009, pp. 2214-2221, vol. 20, No. 12.

Ward, C.A., et al., "Ionic Mechanism of the Effects of Hydrogen Peroxide in Rat Ventricular Myocytes," J Physiol, 1997, pp. 631-642, vol. 500.

Watson, D.J., et al., "Heparin-Binding Properties of the Amyloidogenic Peptides Aβ and Amylin," The Journal of Biological Chemistry, 1997, pp. 31617-31624, vol. 272, No. 50.

Wautier, J., et al., "Protein Glycation: A Firm Link to Endothelial Cell Dysfunction," Circulation Research, Journal of the American Heart Association, 2004, pp. 233-238, vol. 95.

Weiler, J.M., et al., "Heparin and Modified Heparin Inhibit Complement Activation in Vivo," J Immunol., 1992, pp. 3210-3215, vol. 148.

Weiser, J.N., et al., "Phosphorylcholine on the Lipopolysaccharide of Haemophilus Influenzae Contributes to Persistance in the Respiratory Tract and Sensitivity to Serum Killing Mediated by C-Reactive Protein," J Exp Med., 1998, pp. 631-640, vol. 187.

Weiss, J.N., et al., "Role of the Mitochondrial Permeability Transition in Myocardial Disease," Circulation Research, 2003, pp. 292-301.

Weitz, J.I., et al., "Vasoflux, a New Anticoagulant With a Novel Mechanism of Action," Circulation, Journal of the American Heart Association, 1999, pp. 682-689, vol. 99.

Wickley, P.J., et al., "Propofol Modulates Na+—Ca2+ Exchanger Activity Via Activation of Protein Kinase C in Diabetic Cardiomyocytes," Anesthesiology, 2007, pp. 302-311, vol. 106.

Wright, T.C., et al., "Regulation of Cellular Proliferation by Heparin and Heparan Sulfate," Heparin, 1989, pp. 295-316.

Wulczyn, F.G., et al., "The NF-κB/Rel and IkB Gene Families: Mediators of Immune Response and Inflammation," J Mal. Med., 1996, pp. 749-769, vol. 74.

Xuan, Y-T., et al., "Nuclear Factor-Kb Plays an Essential Role in the Late Phase of Ischemic Preconditioning in Conscious Rabbits," Circ. Res., 1999, pp. 1095-1109, vol. 84.

Yan, S.D., et al., "Receptor-Dependent Cell Stress and Amyloid Accumulation in Systemic Amyloidosis," Nature Medicine, 2000, pp. 643-651, vol. 6, No. 6.

\* cited by examiner

TREATMENT OF MYELODYSPLASTIC SYNDROMES WITH 2-O AND,OR 3-O DESULFATED HEPARINOIDS

1. CROSS-REFERENCE TO RELATED APPLICATIONS

This application claims priority to U.S. Provisional Patent Application No. 62/277,360, filed Jan. 11, 2016; 62/181,513, filed Jun. 18, 2015; and 62/117,409, filed Feb. 17, 2015, the disclosures of which are incorporated herein by reference in their entireties for all purposes.

2. BACKGROUND

Animal models have long predicted that heparin and various heparin derivatives would enhance the efficacy of chemotherapy in the treatment of human cancers. Tani and colleagues, for example, reported that heparin enhances potency of gemcitabine in a pancreatic cancer model (Tani et al., Abstract 4175, *Cancer Res.* 70(8) (Suppl. 1) (2010)). WO 2012/106379 analogously reports that a substantially non-anticoagulating 2-O, 3-O-desulfated heparin derivative, "ODSH", improves the efficacy of a chemotherapy regimen that includes gemcitabine in a standard tumor xenograft animal model of human pancreatic cancer.

However, the animal models have proven to be poor at predicting efficacy in human patients, and convincing evidence is sparse that adding heparin or various heparin derivatives enhances efficacy of standard antineoplastic treatment regimens.

For example, despite a wealth of data from both preclinical animal models and early human phase II trials that had suggested that low molecular weight heparin ("LMWH") significantly prolongs survival in a wide variety of cancers in patients without venous thromboembolism, Maraveyas and colleagues reported in 2012 that adding the LMWH dalteparin to gemcitabine provided no statistically significant improvement in survival in advanced pancreatic cancer in a properly powered trial (Maraveyas et al., *Eur. J. Cancer* 48:1283-1292 (2012)). In a contemporaneous phase II randomized study, dalteparin could not be shown to improve outcome in ovarian cancer patients being treated with a standard chemotherapy regimen (Elit et al., *Thromb Res.* 130(6):894-900 (2012)). A few months earlier, van Doormaal et al. had analogously reported that adding the LMWH nadroparin to existing standard of care protocols in patients with advanced prostate, lung, or pancreatic cancer provided no statistically significant survival benefit (van Doormaal et al., *J. Clin. Oncol.* 29:2071-2076 (2011)).

Similarly, despite the evidence from animal models that ODSH could enhance the efficacy of chemotherapeutic regimens in treatment of pancreatic cancer, no statistically significant benefit in progression-free survival or overall survival was observed in a later human clinical trial testing addition of ODSH to the standard-of-care chemotherapy regimen of gemcitabine plus nab-paclitaxel in patients with metastatic adenocarcinoma of the pancreas (ClinicalTrial.gov NCT01461915).

Despite continuing advances in treating cancer, there is still a need in the art for more effective treatments, and for treatments that have fewer side effects.

Myelodysplastic syndromes ("MDS") represent a spectrum of clonal hematopoietic stem cell disorders characterized by progressive bone marrow failure and increased risk of progression to acute myeloid leukemia ("AML", also known as "acute myelogenous leukemia"). The International Prognostic Scoring System ("IPSS") is widely used to identify patients with high risk features based on the severity of their cytopenias, bone marrow myeloblast percentage, and cytogenetic abnormalities. For patients with MDS, allogeneic hematopoietic stem cell transplantation remains the only curative treatment option. However, MDS is a disease of older individuals, with fewer than 5 percent of cases occurring in patients younger than 50 years and the majority being diagnosed at an age over 70 years. Because of age, comorbidities, and other factors, less than 10 percent of all MDS patients are able to proceed to potentially curative allogeneic hematopoietic stem cell transplantation.

Hypomethylating agents are considered standard first line therapy for patients with higher risk disease. Unfortunately, these agents are not curative and only achieve remission in approximately 20-30 percent of patients, with a median duration of response of 8-10 months. Outcomes after hypomethylating agents are poor. There remains an unmet need for better treatment of myelodysplasias.

3. SUMMARY

It has now been discovered that heparin derivatives (collectively, "heparinoids") that are capable of inhibiting, reducing, abrogating or otherwise interfering with the binding of CXCL12 to CXCR4 ("CXCL12-interacting heparinoids") can increase the efficacy of antineoplastic regimens against a selected subset of cancers, those in which interaction of CXCL12 with CXCR4 privileges the cancer against therapeutic intervention. In certain embodiments, the cancers are those in which neoplastic cells, including but not limited to cancer stem cells, migrate to and/or reside in one or more anatomic sites, such as the bone marrow, that provide protection from the antineoplastic regimen. In certain embodiments, the cancers are those in which stromal cell expression of CXCL12 protein exerts a prosurvival influence on tumor cells.

Moreover, because the bone marrow niche upregulates production of CXCR4 and CXCR12 in disorders of hematopoietic stem cells ("HSC"s), and this upregulation is believed to promote survival of the disordered HSCs, heparinoids that are capable of inhibiting, reducing, abrogating or otherwise interfering with the binding of CXCL12 to CXCR4 can increase the efficacy of agents, such as hypomethylating agents, such as azacitidine, that are used to treat such HSC disorders, such as MDS.

Thus, in a first aspect, methods of treating cancer are provided.

The methods comprise administering to a subject receiving an antineoplastic treatment regimen a heparin derivative capable of inhibiting, reducing, abrogating or otherwise interfering with the binding of CXCL12 to CXCR4, wherein the cancer is one in which interaction of CXCL12 with CXCR4 privileges the cancer against therapeutic intervention. The heparin derivative is administered in an amount and at a time effective to enhance effectiveness of the antineoplastic treatment regimen.

In certain embodiments, the cancer is one in which neoplastic cells, such as cancer stem cells, migrate to and/or reside in anatomic sites that are capable of protecting the neoplastic cells from the antineoplastic treatment regimen. The heparin derivative is administered in an amount and at a time effective to enhance effectiveness of the antineoplastic treatment regimen. In typical embodiments, the heparin derivative is administered in an amount effective to mobilize neoplastic cells from the anatomic site that is capable of protecting the neoplastic cells from the antineoplastic treatment regimen. Typically, the amount is effective to mobilize neoplastic cells from the bone marrow.

In certain embodiments, the cancer is one in which stromal cell expression of CXCL12 protein exerts a prosurvival influence on tumor cells. The heparin derivative is administered in an amount and at a time effective to enhance effectiveness of the antineoplastic treatment regimen. In typical embodiments, the heparin derivative is administered in an amount effective to reduce CXCL12-CXCR4 interaction. In certain embodiments, the heparin derivative is administered in an amount effective to reduce tumor-specific immunosuppression.

In a related aspect, improved methods are provided for treating cancers with an antineoplastic treatment regimen, wherein the cancer is one in which interaction of CXCL12 with CXCR4 privileges the cancer against therapeutic intervention, the improvement comprising further administering a heparin derivative that is capable of inhibiting, reducing, abrogating, or otherwise interfering with the binding of CXCL12 to CXCR4, in an amount and at a time effective to enhance effectiveness of the antineoplastic treatment regimen.

In certain embodiments, the cancer is one in which neoplastic cells migrate to and/or reside in anatomic sites capable of protecting the neoplastic cells from an antineoplastic treatment regimen, the improvement comprising further administering a heparin derivative that is capable of inhibiting, reducing, abrogating, or otherwise interfering with the binding of CXCL12 to CXCR4, in an amount and at a time effective to enhance effectiveness of the antineoplastic treatment regimen. In typical embodiments, the heparin derivative is administered in an amount effective to mobilize neoplastic cells from the anatomic site that is capable of protecting the neoplastic cells from the antineoplastic treatment regimen. Typically, the amount is effective to mobilize neoplastic cells from the bone marrow.

In certain embodiments, the cancer is one in which stromal cell expression of CXCL12 protein exerts a prosurvival influence on tumor cells, the improvement comprising further administering a heparin derivative that is capable of inhibiting, reducing, abrogating or otherwise interfering with the binding of CXCL12 to CXCR4, in an amount and at a time effective to enhance effectiveness of the antineoplastic treatment regimen. In typical embodiments, the heparin derivative is administered in an amount effective to reduce CXCL12-CXCR4 interaction. In certain embodiments, the heparin derivative is administered in an amount effective to reduce tumor-specific immunosuppression.

In certain embodiments, the cancer is a carcinoma. In certain embodiments, the cancer is lung cancer. In certain other embodiments, the lung cancer is non-small-cell lung cancer. In certain other embodiments, the cancer is a hematologic cancer. In certain embodiments, the hematologic cancer is leukemia. In certain other embodiments, leukemia is acute myeloid leukemia (AML). In certain embodiments the AML is primary AML. In certain other embodiments, the AML is secondary AML.

In another aspect, methods of treating disorders of hematopoietic stem cells are provided. The methods comprise administering to a subject receiving a treatment regimen for a hematopoietic stem cell disorder a heparin derivative capable of inhibiting, reducing, abrogating or otherwise interfering with the binding of CXCL12 to CXCR4. The heparin derivative is administered in an amount and at a time effective to enhance effectiveness of the treatment regimen.

In certain embodiments, the hematopoietic stem cell disorder is one in which the disordered HSC cells migrate to and/or reside in one or more anatomic sites that provide protection from the treatment regimen, such as the bone marrow. In certain embodiments, the hematopoietic stem cell disorder is one in which stromal cell expression of CXCL12 protein exerts a prosurvival influence on the disordered HSCs.

In some embodiments, the disordered HSC cells have abnormal karyotype. In some of these embodiments, the disordered HSC cells are pre-cancerous stem cells.

In certain embodiments, the hematopoietic stem cell disorder is MDS. In certain embodiments, the disorder is newly diagnosed MDS. In certain embodiments, the disorder is recurrent or refractory MDS.

In certain embodiments, the subject has been diagnosed with MDS and symptomatic anemia. In some of these embodiments, the subject has hemoglobin levels less than 10.0 g/dL or requires red blood cell transfusion. In certain embodiments, the subject has been diagnosed with MDS and thrombocytopenia. In some of these embodiments, the subject has a history of two or more platelet counts less than 50,000/µL or a significant hemorrhage requiring platelet transfusions. In certain embodiments, the subject has been diagnosed with MDS and neutropenia. In some of these embodiments, the subject has two or more absolute neutrophil counts less than 1,000/µL. In certain embodiments, the subject has been diagnosed with MDS and has an IPSS score of INT-1 or higher prior to treatment.

In certain embodiments, the treatment regimen is hypomethylation therapy.

In certain embodiments, the subject has undergone greater than or equal to 4 cycles of treatment of a hypomethylating agent without response, or have documented disease progression after prior response to a hypomethylating therapy.

In certain embodiments, the hypomethylation agent is decitabine.

In certain embodiments, the hypomethylation agent is azacitidine.

In certain embodiments, the azacitidine is administered to the subject intravenously.

In certain embodiments, the azacitidine is administered at a dosage range of 5-500 mg/m$^2$.

In certain embodiments, the azacitidine is administered at 75 mg/m$^2$ as a 15 minute intravenous infusion daily on days 1 through 5 of each 28-day cycle.

In certain embodiments, the azacitidine is administered for up to 6 cycles.

In certain embodiments, the heparin derivative is administered to the subject intravenously.

In certain embodiments, the heparin derivative is administered continuously.

In certain embodiments, the heparin derivative is administered as a bolus injection.

In certain embodiments, the heparin derivative is administered as a bolus injection followed by continuous administration.

In certain embodiments, the heparin derivative is administered subcutaneously.

In certain embodiments, the heparin derivative is administered at a dosage range of 0.01 mg/kg to 100 mg/kg.

In certain embodiments, the heparin derivative is administered as a 4 mg/kg bolus on Day 1 followed by a continuous intravenous infusion of 0.25 mg/kg/hr for days 1 through 5 of each 28-day cycle.

In certain embodiments, the heparin derivative is administered for up to 6 cycles.

In certain embodiments, the heparin derivative is administered prior to the antineoplastic treatment.

In certain embodiments, the heparin derivative is administered concurrently with the antineoplastic treatment.

In certain embodiments, the heparin is administered prior to and concurrently with the antineoplastic treatment.

In certain embodiments, the disorder is one in which neoplastic cells or pre-neoplastic cells, such as cancer stem cells, migrate to and/or reside in anatomic sites that are capable of protecting the neoplastic or pre-neoplastic cells from the antineoplastic treatment regimen. The heparin derivative is administered in an amount and at a time effective to enhance effectiveness of the antineoplastic treatment regimen. In typical embodiments, the heparin derivative is administered in an amount effective to mobilize neoplastic cells from the anatomic site that is capable of protecting the neoplastic cells or pre-neoplastic cells from the antineoplastic treatment regimen. Typically, the amount is effective to mobilize neoplastic cells from the bone marrow.

In certain embodiments, the amount of the heparin derivative is effective to cause a complete response or a near complete response rate in the subject.

In certain embodiments, the amount is effective to cause a partial response rate in the subject.

In certain embodiments, performing the methods will determine the tolerability and toxicities of combination treatment of azacitidine and azacitidine and heparin derivatives.

In certain embodiments, performing the methods will determine the event free, progression free, disease free, 10 year survival and overall survival of subjects treated with azacitine and azacitidine and heparin derivatives.

In certain embodiments, performing the methods will determine hematologic improvement evaluated by absolute neutrophil count, platelet and red blood cell response.

In certain embodiments, performing the methods will determine cytogenetic response as evaluated by reversion to normal karyotype.

In certain embodiments, the disorders are hematologic disorders.

In certain embodiments, the disorders are those in which cells are pre-neoplastic cells.

In certain embodiments, the disorder is myelodysplastic syndrome (MDS).

In certain embodiments, the disorder is newly diagnosed MDS.

In certain embodiments, the disorder is recurrent or refractory MDS.

In certain embodiments, the disorders are those in which stromal cell expression of CXCL12 protein exerts a prosurvival influence on the cells.

In certain embodiments, the anti-neoplastic regimen is treatment with a hypomethylating agent.

In certain embodiments, the hypomethylating agent is azacitidine.

4. BRIEF DESCRIPTION OF THE DRAWINGS

FIG. 1 shows the chemical formula of the ATIII-binding pentasaccharide sequence of USP heparin (also known as "unfractionated heparin", or "UFH") and the comparable sequence of a 2-O, 3-O-desulfated heparin derivative prepared by cold alkaline hydrolysis of UFH.

Figure 2A:
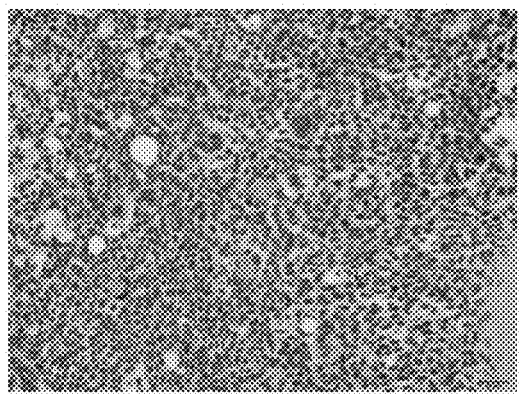
Figure 2B:
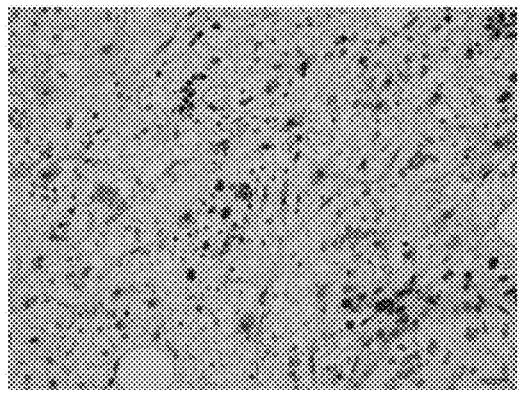
Figure 2C:
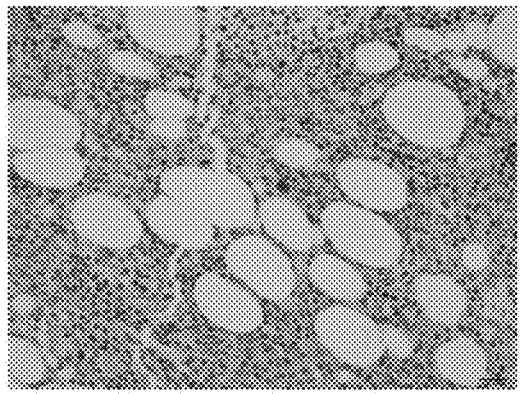

FIGS. 2A-2C are photomicrographs of serial bone marrow biopsies of a patient with acute myeloid leukemia ("AML", also known as acute myelogenous leukemia) treated with an ODSH pharmaceutical composition ("CX-01") in combination with cytarabine and idarubicin, as described in Example 1. FIG. 2A shows bone marrow prior to treatment. FIG. 2B shows marrow at day 14 of treatment. FIG. 2C shows day 28 marrow.

Figure 3:
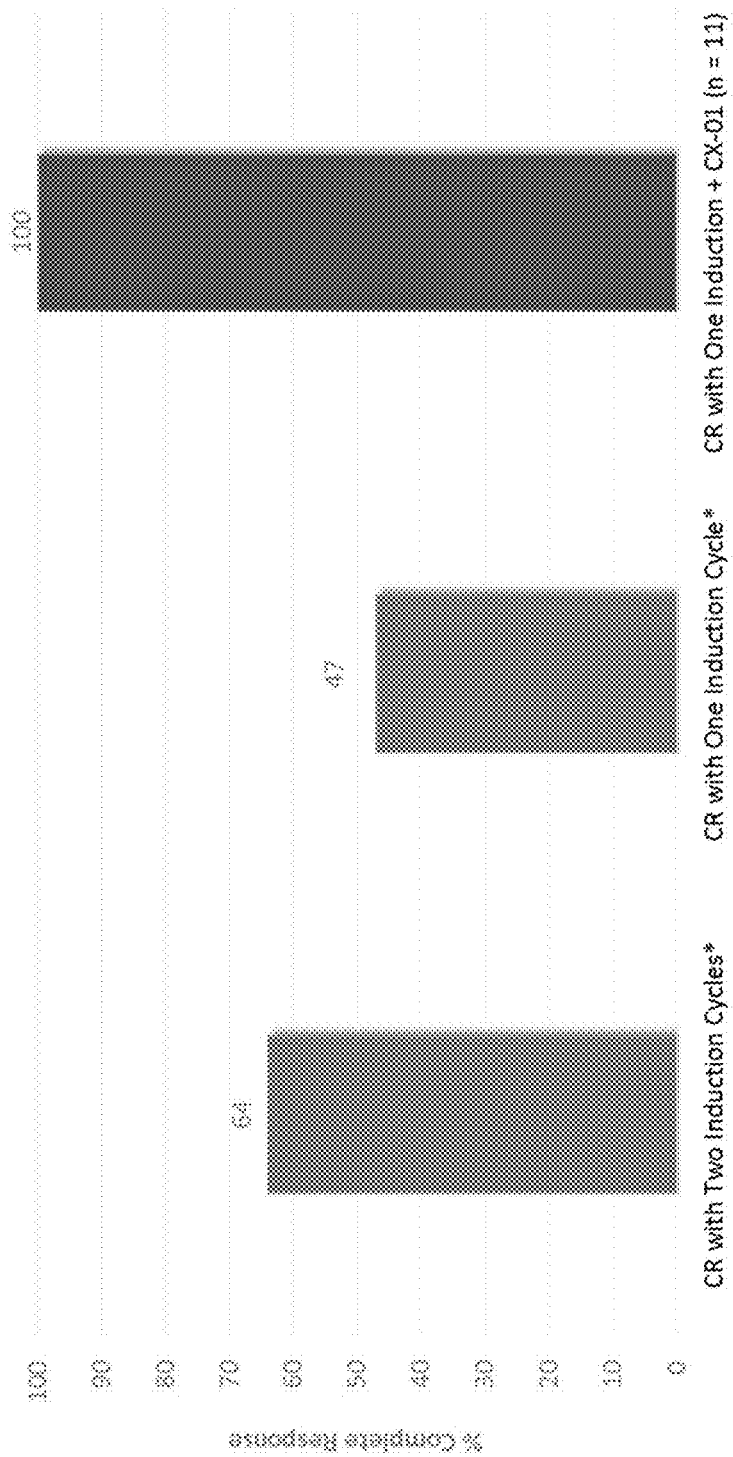

FIG. 3 compares the complete response rate (CR) observed in the clinical trial described in Example 1 to historical control (indicated by asterisk).

5. DETAILED DESCRIPTION

5.1. Overview of Experimental Observations

Data from animal models have long suggested that heparin and certain heparin derivatives can enhance the efficacy of antineoplastic treatment regimens, such as chemotherapy. Despite sporadic anecdotal reports in human patients, however, there is sparse evidence of statistically significant clinical enhancement in human cancer patients.

For example, the substantially non-anticoagulant 2-O, 3-O desulfated heparin derivative, ODSH (see FIG. 1), was shown to sensitize cancer cells to chemotherapy in animal models of human pancreatic adenocarcinoma (WO 2012/106379). When later tested in a human clinical trial (ClinicalTrials.gov identifier NCT01461915), however, addition of ODSH to the chemotherapy regimen did not provide a statistically significant increase in progression-free survival or overall survival in patients with metastatic adenocarcinoma of the pancreas.

Although unable to prolong progression-free survival or overall survival in patients with metastatic pancreatic cancer, ODSH was found, unexpectedly, to attenuate the myelosuppressive side effects of the gemcitabine plus nab-paclitaxel chemotherapy regimen (U.S. Pat. No. 8,734,804, incorporated herein by reference in its entirety).

To confirm the myeloprotective effects of ODSH, a second clinical trial was initiated in a different cancer, acute myeloid leukemia ("AML", also known as acute myelogenous leukemia), treated with a different myelosuppressive chemotherapeutic regimen, idarubicin plus cytarabine (ClinicalTrials.gov identifier: NCT02056782).

As described in detail in Example 1, below, ODSH significantly attenuated the myelosuppressive side effects of the idarubicin+cytarabine anti-AML chemotherapy regimen, as expected. In addition, however, and unexpectedly given prior failure of ODSH to improve response to chemotherapy in the pancreatic cancer trial, ODSH also improved the efficacy of the chemotherapy treatment: 11 out of 12 patients (92%) treated with both ODSH and idarubicin plus cytarabine, including two patients who received an incomplete course of chemotherapy (3 and 5 days respectively), had a morphologic complete remission at the end of a single induction cycle, higher than would otherwise have been expected. All 11 patients with primary AML achieved a complete remission at the end of a single induction cycle. Furthermore, 10 of the 12 patients remain in complete remission 5-13 months after having been enrolled in the study.

Thus, it has now been discovered that ODSH can increase the efficacy of antineoplastic regimens against a selected subset of cancers, notwithstanding the fact that ODSH cannot increase the efficacy of antineoplastic regimens against various other cancers.

As described in Example 2, serial bone marrow biopsies drawn from one of the patients treated with ODSH, cytarabine, and idarubicin in the AML clinical trial unexpectedly showed significant depletion of cellular elements in addition to the expected depletion of leukemic cells. FIG. 2A shows bone marrow prior to treatment, demonstrating that the marrow is packed with leukemia cells. FIG. 2B shows marrow at Day 14 of the induction cycle, demonstrating elimination of most normal bone marrow cells as well as leukemia cells. FIG. 2C shows day 28 marrow, with no evidence of leukemic cells and restoration of normal bone marrow appearance and function.

Without intending to be bound by theory, the unexpected clearance of cells from the marrow seen in the Day 14 biopsy suggests that the increased remission rate observed in the AML clinical trial can be attributed to ODSH-mediated mobilization of leukemic cells from the marrow into the peripheral circulation, where they became vulnerable to the infusions of cytarabine and idarubicin. Retention of leukemic cells in the bone marrow is known to make them more resistant to chemotherapy (Hope et al., *Nat. Immunol.* 5:738-742 (2004)). The recovery of the marrow by Day 28 demonstrates further that the ODSH-mediated flushing of cells from the marrow does not adversely affect the ability of the marrow to repopulate and support multi-lineage hematopoiesis. Indeed, the accelerated recovery of platelet and white cell count, consistent with observations from the previous trial in pancreatic cancer, demonstrates that the marrow microenvironments required for thrombopoiesis, erythropoiesis, and granulopoiesis remain healthy.

CXCL12, also known as Stromal Cell Derived Factor-1 or SDF-1, was originally described as a CXC chemokine produced locally within the bone marrow compartment to provide a homing signal for hematopoietic stem cells ("HSC"s). CXCL12 is the ligand for the CXCR4 receptor on the surface of HSCs; ligation of CXCR4 by CXCL12 is known to promote stem cell survival, proliferation, migration, and chemotaxis (see, e.g., Lapidot et al., *Leukemia* 16(10):1992-2003 (2002)). It has also been reported that the CXCR4 receptor is prominently expressed on the cell membrane of many cancer cells, particularly cancer stem cells (Yu et al., *Gene* 374:174-9 (2006); Cojoc et al., *Oncotargets & Therapy* 6:1347-1361(2013)), and that the CXCL12/CXCR4 interaction may mediate migration of cancer cells to anatomic sites that produce CXCL12 (Wald et al., *Theranostics* 3:26-33 (2013); Cojoc et al., supra).

5.2. Methods of Treatment

5.2.1. Methods of Treating Cancer

Accordingly, in a first aspect, methods of treating cancer are provided.

The methods comprise administering to a subject receiving an antineoplastic treatment regimen a heparin derivative capable of inhibiting, reducing, abrogating or otherwise interfering with the binding of CXCL12 to CXCR4, wherein the cancer is one in which interaction of CXCL12 with CXCR4 privileges the cancer against therapeutic intervention. The heparin derivative is administered in an amount and at a time effective to enhance effectiveness of the antineoplastic treatment regimen.

In certain embodiments, the cancer is one in which neoplastic cells, such as cancer stem cells, migrate to and/or reside in anatomic sites that are capable of protecting the neoplastic cells from the antineoplastic treatment regimen. The heparin derivative is administered in an amount and at a time effective to enhance effectiveness of the antineoplastic treatment regimen. In typical embodiments, the heparin derivative is administered in an amount effective to mobilize neoplastic cells from the anatomic site that is capable of protecting the neoplastic cells from the antineoplastic treatment regimen. Typically, the amount is effective to mobilize neoplastic cells from the bone marrow.

In certain embodiments, the cancer is one in which stromal cell expression of CXCL12 protein exerts a prosurvival influence on tumor cells. The heparin derivative is administered in an amount and at a time effective to enhance effectiveness of the antineoplastic treatment regimen. In typical embodiments, the heparin derivative is administered in an amount effective to reduce CXCL12-CXCR4 interaction. In certain embodiments, the heparin derivative is administered in an amount effective to reduce tumor-specific immunosuppression.

In a related aspect, improved methods are provided for treating cancers with an antineoplastic treatment regimen, wherein the cancer is one in which interaction of CXCL12 with CXCR4 privileges the cancer against therapeutic intervention, the improvement comprising further administering a heparin derivative that is capable of inhibiting, reducing, abrogating or otherwise interfering with the binding of CXCL12 to CXCR4, in an amount and at a time effective to enhance effectiveness of the antineoplastic treatment regimen.

In certain embodiments, the cancer is one in which neoplastic cells migrate to and/or reside in anatomic sites capable of protecting the neoplastic cells from an antineoplastic treatment regimen, the improvement comprising further administering a heparin derivative that is capable of inhibiting, reducing, abrogating or otherwise interfering with the binding of CXCL12 to CXCR4, in an amount and at a time effective to enhance effectiveness of the antineoplastic treatment regimen. In typical embodiments, the heparin derivative is administered in an amount effective to mobilize neoplastic cells from the anatomic site that is capable of protecting the neoplastic cells from the antineoplastic treatment regimen. Typically, the amount is effective to mobilize neoplastic cells from the bone marrow.

In certain embodiments, the cancer is one in which stromal cell expression of CXCL12 protein exerts a prosurvival influence on tumor cells, the improvement comprising further administering a heparin derivative that is capable of inhibiting, reducing, abrogating or otherwise interfering with the binding of CXCL12 to CXCR4, in an amount and at a time effective to enhance effectiveness of the antineoplastic treatment regimen. In typical embodiments, the heparin derivative is administered in an amount effective to reduce CXCL12-CXCR4 interaction. In certain embodiments, the heparin derivative is administered in an amount effective to reduce tumor-specific immunosuppression.

5.2.1.1. Selected Cancers

5.2.1.1.1. Cancers Characterized by Migration to Privileged Anatomic Sites In certain embodiments of the methods described herein, the cancer is selected from those in which neoplastic cells migrate to and/or reside in anatomic sites that are capable of protecting the neoplastic cells from an antineoplastic treatment regimen (hereinafter, "privileged anatomic sites"). In various embodiments, the privileged anatomic site is selected from the group consisting of bone marrow, liver, and brain. In typical embodiments, the privileged anatomic site is the bone marrow.

In some embodiments, the cancer is a hematologic cancer. In various such embodiments, the cancer is selected from the group consisting of acute myeloid leukemia ("AML", also known as acute myelogenous leukemia, or "AML"), acute lymphoblastic leukemia, chronic lymphocytic leukemia, chronic myelogenous leukemia, and acute monocytic leukemia.

In some embodiments, the cancer to be treated is a cancer having substantial potential to metastasize to the bone marrow. In various of these embodiments, the cancer is selected from the group consisting of prostate cancer, breast cancer, lung cancer and melanoma, all of which show high rates of metastasis to the bone and can home into the niche occupied by HSCs (see, e.g., Kaplan et al., *Cancer Metastasis Rev.* 25(4):521-9 (2006), incorporated herein by reference in its entirety). In certain embodiments, the cancer is kidney cancer, thyroid cancer, or neuroblastoma. In certain embodiments, the cancer to be treated is head and neck cancer, esophagus cancer, stomach cancer, colorectal cancer, or sarcoma.

In some embodiments, the cancer to be treated is selected from the group consisting of metastatic prostate cancer, metastatic lung cancer, including metastatic non-small cell lung cancer, metastatic breast cancer, and metastatic neuroblastoma.

In some embodiments, the cancer to be treated is lung cancer.

In certain lung cancer embodiments, the cancer is small cell lung cancer. In other embodiments, the lung cancer is non-small cell lung cancer ("NSCLC").

In certain NSCLC embodiments, the NSCLC is locally advanced. In certain embodiments, the NSCLC is inoperable. In certain embodiments, the NSCLC is locally advanced and inoperable. In certain embodiments, the non-small cell lung cancer is Stage IIIB NSCLC. In some embodiments, the NSCLC is oligometastatic stage IV non-small cell lung cancer. In some embodiments, the NSCLC is being treated with radiation therapy and chemotherapy.

In some embodiments, the cancer to be treated is characterized by the presence of post-treatment minimal residual disease. "Minimal residual disease" generally refers to cancer cells that persist after antineoplastic therapy, and whose presence is correlated with relapse of the disease. Without intending to be bound by theory, the minimal residual disease state is attributed to persistence of cancer stem cells, often resident in privileged anatomic sites, and which are more resistant to therapeutic treatments and have the capacity to give rise to variant cancer cell types found in the particular cancer. By escaping effect of cancer treatments, the cancer stem cells can cause relapse and metastasis by producing new cancer cell types. In particular, cancers with minimal residual disease in the bone marrow, liver, brain, or other similar tissues are appropriate cancers to be treated according to the methods described herein.

In certain embodiments, cancers with minimal residual disease states are selected from the group consisting of breast cancer, glioblastoma, small cell lung cancer, non-small cell lung cancer, prostate cancer, primary acute myeloid leukemia, secondary acute myeloid leukemia, refractory acute myeloid leukemia, and chronic myelogenous leukemia. In some embodiments, any cancer with minimal residual disease in the bone marrow or like tissues that protect neoplastic cells from antineoplastic treatment following initial antineoplastic treatment is an appropriate cancer to be treated according to the methods described herein.

5.2.1.1.2. Cancers Characterized By Stromal Expression Of CXCL12

In certain embodiments, the cancer is selected from those in which stromal expression of CXCL12 protein exerts a prosurvival influence on tumor cells.

In certain embodiments, the cancer is selected from adenocarcinomas. In certain embodiments, the cancer is selected from primary and metastatic carcinomas. In various embodiments, the cancer is selected from prostate, colorectal, breast, ovarian, bladder, lung (including small cell lung cancer and non-small cell lung cancer), and hepatocellular carcinoma.

5.2.1.2. Antineoplastic Treatment Regimens

In the methods described herein, the antineoplastic treatment regimen is any antineoplastic treatment regimen appropriate for the cancer being treated.

In some embodiments, the treatment regimen includes chemotherapy. In some embodiments, the treatment regimen includes radiation therapy. In some embodiments, the treatment regimen includes antibody therapy. In some embodiments, the treatment regimen includes therapy targeted to mutant enzymes, such as mutated kinases. In some embodiments, the treatment regimen includes immunotherapy, such as immunotherapy with a checkpoint inhibitor.

In the methods provided herein, the antineoplastic treatment regimen can be myelosuppressive or non-myelosuppressive.

Myelosuppressive antineoplastic treatment regimens include those that reduce one or more of platelet count, red blood cell count, white blood cell count, and particularly, neutrophil count. In certain embodiments, the myelosuppressive antineoplastic treatment regimen is capable of causing a grade 1, grade 2, grade 3, or grade 4 thrombocytopenia when administered without adjunct administration of a CXCL12-interacting heparinoid. In some embodiments, the myelosuppressive antineoplastic treatment regimen is capable of causing a grade 1, grade 2, grade 3, or grade 4 neutropenia when administered without adjunct administration of a CXCL12-interacting heparinoid.

In some embodiments, the myelosuppressive antineoplastic treatment regimen includes administration of one or more of an alkylating agent, antimetabolite, anthracyclines, topoisomerase inhibitors or mitotic inhibitors.

In some embodiments, the myelosuppressive antineoplastic treatment regimen includes administration of one or more of venetoclax, decitabine, LY573636, aldesleukin, bortezomib, ixazomib, tipifarnib, panobinostat, pracinostat, clorfarabine, alvocidib, lenolidamide, dasatinib, volasertib, sorafenib, CP-351, vosaroxin, etoposide, mitoxantrone, guadecitabine, gemtuzumab ozogamicin, SGN-CD33A, BI 836858, AGS67E, arsenic trioxide, vorinostat, binimetinib, trametinib, BVD-523, E6201, vyxeos, AZD1775, 8-chloroadenosine, cladribine, flutarabine, capecitidine, pomalidomide, erwinaze, treosulfan, alisertib, gedatolisib, ruxolitinib, LY2606368, OXi4503, gliteritinib, sunitinib, lestaurtinib, midostaurin, quizartinib, crenolanib, pacritinib, AKN-028, FLX925 or E6201.

In some embodiments, the myelosuppressive antineoplastic treatment regimen includes administration of one or more of a FMS-related tyrosine kinase-3 inhibitor, a tyrosine kinase inhibitor, a proteasome inhibitor, a histone deacetylase inhibitor, a CD-33 inhibitor, a MEK inhibitor, a purine analog, an asparaginase, an mTOR inhibitor or an Aurora Kinase inhibitor.

In particular embodiments, the antineoplastic treatment regimen is a non-myelosuppressive treatment regimen. As used herein, "non-myelosuppressive" treatment regimen refers to a treatment regimen that does not substantially reduce one or more of platelet count, red blood cell count, white blood cell count, and neutrophil count when administered without adjunct administration of a CXCL12-interacting heparinoid. In preferred embodiments, the non-myelosuppressive treatment regimen does not cause a grade 1, grade 2, grade 3, or grade 4 thrombocytopenia when administered without adjunct administration of a CXCL12-interacting heparinoid. In certain embodiments, the non-myelosuppressive treatment regimen does not cause a grade 1, grade 2, grade 3, or grade 4 neutropenia when administered without adjunct administration of a CXCL12-interacting heparinoid.

In some embodiments, the non-myelosuppressive antineoplastic treatment regimen includes administration of one or more of a kinase inhibitor, a VEGF inhibitor, a VEGFR inhibitor, a VEGFR2 inhibitor, a PDGFR inhibitor, a Src family kinase inhibitor, a hedgehog inhibitor, a retinoid X receptor activator, a histone methyltransferase inhibitor, a BCL2 inhibitor, an AKT inhibitor, a CXCR4 inhibitor, an mTOR inhibitor, an Mdm2 antagonist, an Mdm2 inhibitor, a CD25 inhibitor, a CD47 inhibitor, an IL-3R inhibitor, a BCR-Abl inhibitor, a HSP90 inhibitor, an HGF inhibitor, a MET inhibitor and a bromodomain and extra-terminal domain (BET) inhibitor and a BRD4 inhibitor.

In some embodiments, the non-myelosuppressive treatment regimen includes administration of one or more of crizotinib, seliciclib, afatinib, aldesleukin, alemtuzumab; axitinib, belinostat, bosutinib, brentuximab vedotin, carfilzomib, ceritinib, dabrafenib, dasatinib, everolimus, ibritumomab tiuxetan, ibrutinib, sorafenib, idelalisib, ipilimumab, nilotinib, obinutuzumab, ofatumumab, panitumumab, pembrolizumab, pertuzumab, ponatinib, ramucirumab, regorafenib, romidepsin, sipuleucel, temsirolimus, tositumomab, trametinib, vandetanib, vemurafenib, vismodegib, vorinostat, ziv-aflibercept, cabozantinib, selinexnor, PF-4449913, erismodegib, GO-203-2C, thioridazine, nivolumab. bexarotene, EPZ-5676, ABT-199, GSK2141795, entospletinib, TAK-659, CPI-613, B 1-8040, LY2510924, plerixafor, mozobil, OCV-501, pacritinib, eltrombopag, promacta, revolade, nintedanib, vargatef, rapamycin, MEN1112, ipilimumab, idasanutlin, RO6839921, AMG-232, ADCT-301, KHK2823, CWP232291, SL-401, CC-90002, GSK2879552, lirilumab, BGB324, OTX-015, TEN-010, I-BET 762, CPI-203, CPI-0610, AG-120, AG-221 or IDH305.

In some embodiments, the non-myelosuppressive treatment regimen includes administration of one or more of bleomycin, vincristine, prednisolone, and gallium nitrate.

In some embodiments, the non-myelosuppressive antineoplastic treatment regimen comprises administration of a non-myelosuppressive targeted therapeutic agent or an immunostimulatory or immunomodulatory therapeutic agent. As used herein, a "non-myelosuppressive targeted therapeutic" refers to a therapeutic agent that targets the cancer cell with sufficient specificity to not have myelosuppressive effects.

A "non-myelosuppressive immunostimulatory therapeutic" refers to a therapeutic agent that stimulates immune activity against the cancer cells, such as by reducing suppression of effector immune cells or activating immune cells that result in a therapeutic response against the cancer cells.

In some embodiments, the immunostimulatory therapeutic agent comprises one or more checkpoint inhibitors. In certain embodiments, the checkpoint inhibitor is a monoclonal antibody. In certain embodiments, the monoclonal antibody is selected from an anti-CTLA-4 monoclonal antibody, an anti-PD1 monoclonal antibody, an anti-PDL1 monoclonal antibody, and combinations thereof.

5.2.2. Methods of Treating Hematopoietic Stem Cell Disorders

In another aspect, methods of treating hematopoietic stem cell disorders are provided.

The methods comprise administering to a subject receiving a treatment regimen for a hematopoietic stem cell disorder a heparin derivative capable of inhibiting binding of CXCL12 to CXCR4. The heparin derivative is administered in an amount and at a time effective to enhance effectiveness of the treatment regimen.

In certain embodiments, the hematopoietic stem cell disorder is one in which the disordered HSC cells migrate to and/or reside in one or more anatomic sites that provide protection from the treatment regimen, such as the bone marrow. In certain embodiments, the hematopoietic stem cell disorder is one in which stromal cell expression of CXCL12 protein exerts a prosurvival influence on the disordered HSCs. In certain embodiments, the hematopoietic stem cell disorder is one in which stromal cell expression of CXCL12 protein inhibits apoptosis of the disordered HSCs.

In some embodiments, the disordered HSC cells have abnormal karyotype. In some of these embodiments, the disordered HSC cells are pre-cancerous stem cells.

In certain embodiments, the hematopoietic stem cell disorder is myelodysplastic syndrome ("MDS", also known as "myelodysplasia"). In certain embodiments, the disorder is newly diagnosed MDS. In certain embodiments, the disorder is recurrent or refractory MDS.

In certain embodiments, the subject has been diagnosed with MDS and symptomatic anemia. In some of these embodiments, the subject has hemoglobin levels less than 10.0 g/dL or requires red blood cell transfusion. In certain embodiments, the subject has been diagnosed with MDS and thrombocytopenia. In some of these embodiments, the subject has a history of two or more platelet counts less than 50,000/μL or a significant hemorrhage requiring platelet transfusions. In certain embodiments, the subject has been diagnosed with MDS and neutropenia. In some of these embodiments, the subject has two or more absolute neutrophil counts less than 1,000/μL. In certain embodiments, the subject has been diagnosed with MDS and has an IPSS score of INT-1 or higher prior to treatment.

In typical embodiments, the treatment regimen for myelodysplasia is hypomethylation therapy. In certain embodiments, the subject has not undergone prior treatment with hypomethylation therapy. In other embodiments, the subject has undergone prior treatment with a hypomethylating agent. In various of these embodiments, the subject has undergone 1 prior treatment, 2 prior treatments, 3 prior treatments, or even 4 prior treatments with a hypomethylating agent without complete remission.

In certain embodiments, the hypomethylation agent is decitabine.

In certain embodiments, the hypomethylation agent is azacitidine. In certain azacitidine embodiments, the azacitidine is administered to the subject intravenously. In certain embodiments, the azacitidine is administered at a dosage range of 5-500 mg/m$^2$. In certain embodiments, the azacitidine is administered at 75 mg/m$^2$ as a 15 minute intravenous infusion daily on days 1 through 5 of each 28-day cycle. In certain embodiments, the azacitidine is administered for up to 6 cycles.

In certain embodiments, the heparin derivative is administered to the subject intravenously. In certain intravenous embodiments, the heparin derivative is administered as a bolus injection. In certain intravenous embodiments, the heparin derivative is administered continuously. In certain intravenous embodiments, the heparin derivative is administered as a bolus injection followed by continuous administration.

In certain embodiments, the heparin derivative is administered as a 4 mg/kg bolus on Day 1 followed by a continuous intravenous infusion of 0.25 mg/kg/hr for days 1 through 5 of each 28-day cycle. In certain embodiments, the heparin derivative is administered for up to 6 cycles. In certain embodiments, the heparin derivative is administered prior to the myelodysplasia treatment regimen. In certain embodiments, the heparin derivative is administered concurrently with the myelodysplasia treatment regimen. In certain embodiments, the heparin is administered prior to and concurrently with the myelodysplasia treatment regimen. In typical embodiments, the myelodysplasia treatment regimen is administration of a hypomethylation agent.

In certain embodiments, the heparin derivative is administered subcutaneously. In certain subcutaneous administration embodiments, the heparin derivative is administered at a dosage range of 0.01 mg/kg to 100 mg/kg.

In certain embodiments, the hematopoietic stem cell disorder is one in which the disordered HSC cells migrate to and/or reside in anatomic sites that are capable of protecting the cells from the treatment regimen. The heparin derivative is administered in an amount and at a time effective to enhance effectiveness of the treatment regimen. In typical embodiments, the heparin derivative is administered in an amount effective to mobilize HSC cells from the anatomic site that is capable of protecting the disordered HSC cells from the antineoplastic treatment regimen. Typically, the amount is effective to mobilize HSC cells from the bone marrow.

In certain embodiments, the amount of the heparin derivative is effective to cause a complete response or a near complete response rate in the subject. In certain embodiments, the amount is effective to cause a partial response rate in the subject.

In certain embodiments, the methods of treatment are effective to result in improved event free survival as compared to treatment without administration of the heparin derivative. In some embodiments, the methods of treatment are effective to result in improved progression free survival as compared to treatment without administration of the heparin derivative. In some embodiments, the methods of treatment are effective to result in improved disease free survival, 10 year survival, and/or overall survival as compared to treatment without administration of the heparin derivative. In certain embodiments, the methods of treatment result in reversion of the disordered HSC cells to normal karyotype.

5.2.3. Effective Heparin Derivatives

In the methods described herein, the heparin derivative is one capable of inhibiting, reducing, abrogating, or otherwise interfering with the binding of CXCL12 to CXCR4. For convenience, such heparin derivatives are collectively referred to herein as "CXCL12-interacting heparinoids".

In some embodiments, the CXCL12-interacting heparinoid inhibits binding of CXCL12 to CXCR4 with an $IC_{50}$ of about 0.05 µg/ml or less, about 0.04 µg/ml or less, about 0.03 µg/ml or less, about 0.02 µg/ml or less, or about 0.01 µg/ml or less in the assay set forth in Example 3. In some embodiments, the CXCL12-interacting heparinoid inhibits binding of CXCL12 to CXCR4 with an $IC_{90}$ of about 0.7 µg/ml or less, about 0.6 µg/ml or less, about 0.5 µg/ml or less, or about 0.4 µg/ml or less in the assay set forth in Example 3. In some embodiments, the CXCL12-interacting heparinoid is characterized by an $IC_{50}$ of about 0.01 µg/ml and an $IC_{90}$ of about 0.5 µg/ml as determined by the method in Example 3. In some embodiments, the CXLC12-interacting heparinoid is capable of inhibiting CXLC12/CXCR4 interaction, as measured by the method set forth in Example 3, which is about the same as an equivalent weight of unfractionated heparin.

In typical embodiments, the CXCL12-interacting heparinoid is capable of effecting at least 20% inhibition of the binding of CXCL12 to CXCR4 in the assay set forth in Example 3 at a concentration that, if achieved in plasma, would not effect substantial anticoagulation. In various embodiments, the CXCL12-interacting heparinoid is capable of effecting at least 25% inhibition of the binding of CXCL12 to CXCR4 in the assay set forth in Example 3 at a concentration that, if achieved in plasma, would not effect substantial anticoagulation. In certain embodiments, the CXCL12-interacting heparinoid is capable of effecting at least 30%, at least 35%, at least 40%, at least 45%, at least 50%, at least 55%, at least 60% inhibition of the binding of CXCL12 to CXCR4 in the assay set forth in Example 3 at a concentration that, if achieved in plasma, would not effect substantial anticoagulation. In specific embodiments, the CXCL12-interacting heparinoid is capable of effecting at least 65%, at least 70%, at least 80%, at least 85%, even at least 90%, 91%, 92%, 93%, 94%, 95% inhibition of the binding of CXCL12 to CXCR4 in the assay set forth in Example 3 at a concentration that, if achieved in plasma, would not effect substantial anticoagulation. In particular embodiments, the CXCL12-interacting heparinoid is capable of effecting at least 96%, 97% even at least 98% inhibition of the binding of CXCL12 to CXCR4 in the assay set forth in Example 3 at a concentration that, if achieved in plasma, would not effect substantial anticoagulation.

In various embodiments, the CXCL12-interacting heparinoid is capable of binding to CXCL12 under physiological conditions.

In preferred embodiments, the CXCL12-interacting heparinoid is a derivative of USP heparin (also known as "unfractionated heparin", "UFH") that is substantially desulfated at the 2-O position of α-L-iduronic acid (referred to herein as the "2-O position") and/or 3-O position of D-glucosamine-N-sulfate (6-sulfate) (referred to herein as the "3-O position"). In preferred embodiments, the 2-O, 3-O-desulfated heparin derivative is not substantially desulfated at the 6-O or N positions.

For purposes of the present disclosure, the percentage desulfation at the 2-O position of a sample of 2-O, 3-O-desulfated heparin derivative ("ODSH") is defined as the percentage reduction in sulfate functional groups on the 2-O position of the 2-O-sulfo-α-L-iduronic acid residues as compared to the sulfate functional groups on the 2-O positions of the 2-O-sulfo-α-L-iduronic acid residues in a sample of the 6th International Standard for Unfractionated Heparin, NIBSC code 07/328 ("NIBSC standard"). For purposes of the present disclosure, the percentage desulfation at the 3-O position of a sample of ODSH is defined as the percentage reduction in sulfate functional groups on the 3-O position of the 2-deoxy-2-sulfamido-3-O-sulfo-α-D-glucopyranosyl-6-O-sulfate residues as compared to the sulfate functional groups on the 3-O positions of the 2-deoxy-2-sulfamido-3-O-sulfo-α-D-glucopyranosyl-6-O-sulfate residues in a sample of the NIBSC standard.

In some embodiments, the CXCL12-interacting heparinoid is at least 85%, at least 90%, at least 95%, or at least 99% desulfated at the 2-O position. In some embodiments, the CXCL12-interacting heparinoids are at least 85%, at least 90%, at least 95%, or at least 99% desulfated at the 3-O position. In some embodiments, the CXCL12-interacting heparinoids are at least 85%, at least 90%, at least 95%, at least 99% desulfated at the 2-O position and the 3-O position.

For purposes herein, average molecular weight of heparinoids is weight-average molecular weight, Mw, and is determined by size exclusion chromatography according to the USP monograph for Enoxaparin sodium, with USP Heparin MW Calibrant used as an additional calibrant.

In some embodiments, the CXCL12-interacting heparinoids have an average molecular weight from about 2 kDa to about 15 kDa. In some embodiments, the CXCL12-interacting heparinoids have an average molecular weight of at least about 2 kDa, at least about 3 kDa, at least about 4 kDa, at least about 5 kDa, at least about 6 kDa, or at least about 7 kDa. In some embodiments, the CXCL12-interacting heparinoids have an average molecular weight of less than about 15 kDa, less than about 14 kDa, less than about 13 kDa, less than about 12 kDa, less than about 11 kDa, less than about 10 kDa, or less than about 9 kDa. In some embodiments, the average molecular weight of the CXCL12-interacting heparinoid is selected from about 2 kDa, 3 kDa, 4 kDa, 5 kDa, 6 kDa, 7 kDa, 8 kDa, 9 kDa, 10 kDa, 11 kDa, 12 kDa, 13 kDa, 14 kDa, 15 kDa, 16 kDa, 17 kDa, 18 kDa, or a range that includes any of these values as endpoints.

In some embodiments, the substantially 2-O, 3-O desulfated CXCL12-interacting heparinoid for use in the methods described herein are compositions in which the average molecular weight is at least about 8 kDa. In some embodiments, the substantially 2-O, 3-O desulfated CXCL12-interacting heparinoids have an average molecular weight of greater than about 8 kDa. In various embodiments, the substantially 2-O, 3-O desulfated CXCL12-interacting heparinoids have an average molecular weight ranging from about 8 kDa to about 15 kDa. In some embodiments, the substantially 2-O, 3-O desulfated CXCL12-interacting heparinoids for use in the methods described herein have an average molecular weight that ranges in size from about 11 kDa to about 13 kDa.

An exemplary CXCL12-interacting heparinoid is substantially 2-O, 3-O desulfated heparin, referred to herein as ODSH. ODSH for use in the above-described methods can be prepared from bovine or porcine heparin. In an exemplary method of preparing ODSH from porcine heparin, ODSH is synthesized by cold alkaline hydrolysis of USP porcine intestinal heparin, which removes the 2-O and 3-O sulfates, leaving N- and 6-O sulfates on D-glucosamine sugars and carboxylates on α-L-iduronic acid sugars substantially intact (Fryer et al., *J. Pharmacol. Exp. Ther.* 282: 208-219 (1997), incorporated herein by reference in its entirety). Using this method, ODSH can be produced with an average molecular weight of about 11.7±0.3 kDa. Additional methods for the preparation of substantially 2-O, 3-O desulfated CXCL12-interacting heparinoids may also be found, for example, in U.S. Pat. Nos. 5,668,118, 5,912,237, and 6,489,311, and WO 2009/015183, the contents of which are incorporated herein in their entirety, and in U.S. Pat. Nos. 5,296,471; 5,969,100; and 5,808,021.

In contrast to unfractionated heparin, ODSH is substantially non-anticoagulating: administered to a subject at a dose that is equivalent in weight to a fully-anticoagulating dose of unfractionated heparin, the clotting time measured in an aPTT assay is no greater than 45 seconds, and typically in the upper range of normal, where normal clotting time ranges from about 27 to 35 seconds. By comparison, unfractionated heparin administered to a subject at a fully anticoagulant dose causes time to clot to range from about 60 to about 85 seconds in an aPTT assay.

Thus, in certain preferred embodiments, the CXCL12-interacting heparinoid is substantially non-anticoagulating. In preferred embodiments, the CXCL12-interacting heparinoid, if administered to a subject at a dose that is weight equivalent to a fully-anticoagulating dose of unfractionated heparin, the clotting time measured in an aPTT assay is no greater than 45 seconds.

Another measure of ODSH's anticoagulant activity is its anti-$X_a$ activity which can be determined in an assay carried out using plasma treated with Russell viper venom. In specific examples, ODSH exhibited less than 9 U of anticoagulant activity/mg in the USP anticoagulant assay (e.g., 7±0.3 U), less than 5 U of anti-$X_a$ activity/mg (e.g., 1.9±0.1 U/mg) and less than 2 U of anti-$II_a$ activity/mg (e.g., 1.2±0.1 U/mg) (compared to unfractionated heparin which has an activity of 165-190 U/mg in all three assays; Rao et al., *Am. J. Physiol.* 299:C97-C110 (2010), incorporated herein by reference in its entirety). Thus, in certain embodiments, the CXCL12-interacting heparinoid exhibits less than 9 U of anticoagulant activity/mg in the USP anticoagulant assay, and/or less than 5 U of anti-$X_a$ activity/mg, and/or less than 2 U of anti-$II_a$ activity/mg.

Furthermore, ODSH has a low affinity for anti-thrombin III (Kd~339 µM or 4 mg/ml vs. 1.56 µM or 22 µg/ml for unfractionated heparin), consistent with the observed low level of anticoagulant activity, measured as described in Rao et al., supra, at page C98. Thus, in certain embodiments, the CXCL12-interacting heparinoid has a low affinity for anti-thrombin III (Kd~339 µM or 4 mg/ml).

In some embodiments, the CXCL12-interacting heparinoids have no more than 40% of the anticoagulating activity of an equal weight of unfractionated heparin by any one or more of the above-described tests. In some embodiments, the CXCL12-interacting heparinoid has no more than 35%, no more than 30%, no more than 20%, no more than 10%, no more than 9%, no more than 8%, no more than 7%, no more than 6%, no more than 5%, no more than 4%, no more than 3%, no more than 2%, or no more than 1% of the anti-coagulating activity of an equal weight of unfractionated heparin by any one or more of the above-described tests.

In some embodiments, the CXCL12-interacting heparinoid does not trigger platelet activation and does not induce heparin-induced thrombocytopenia (HIT). Platelet activation can be determined using a serotonin release assay, for example as described in U.S. Pat. No. 7,468,358 and Sheridan et al., *Blood* 67:27-30 (1986), incorporated herein by reference. In some embodiments, the CXCL12-interacting heparinoid is capable of binding platelet factor 4, also referred to as chemokine (C-X-C motif) ligand 4 (CXCL4).

In some embodiments, the CXCL12-interacting heparinoid is a low molecular weight heparin (LMWH). "Low molecular weight heparin" or "LMWH" refers to heparin fragments that have a mean molecular weight of about 4 to about 6 kDa. In some embodiments, the LMWHs have a molecular weight distribution of about 1000 to about 10000. LMWHs are typically made by chemical or enzymatic depolymerization of heparin, generally unfractionated heparin, and can be further purified to select the appropriate size of the LMWH. The LMWH can be prepared using a number of different separation or fractionation techniques known to and used by those of skill in the art, including, for example, gel permeation chromatography (GPC), high-performance liquid chromatography (HPLC), ultrafiltration, size exclusion chromatography, and the like.

In certain embodiments, the LMWH is selected from the group consisting of bemiparin, nadroparin, reviparin, enoxaparin, parnaparin, certoparin, dalteparin, tinzaparin, and necuparanib.

In typical embodiments, the CXCL12-interacting heparinoid displays bone marrow cell mobilizing activity, particularly HSC mobilizing activity, more particularly bone marrow-residing cancer cell mobilizing activity. In some embodiments, the CXCL12-interacting heparinoid is characterized by about 50% or more, 60% or more, 70% or more, 80% or more, 90% or more, or 95% or more of the HSC mobilizing activity of an equivalent weight of unfractionated heparin. HSC mobilizing activity can be measured by mobilization of cells having one or more of the marker profiles listed in Table 1 below. In certain embodiments, HSC mobilizing activity is measured using at least the $CD34^+$ marker phenotype.

TABLE 1

$CD34^+$
$CD34^+$ $CD38^-$
$CD34^+$ $Lin^-$ $Thy1^+$
$CD34^+$ $c\text{-}kit^+$
$CD34^+$ $Tie^+$
$CD34^+$ $CD133^+$
$CD34^-$ $Lin^-$ $CD133^-$ $CD7^-$
$CD34^+$ $CD38^-$ $Lin^-$ $Rhodamine123^{low}$
$CD34^+$ $CD38^-$ $Lin^-$ $CD45RA^-$ $Rhodamine123^{low}$ $CD49f^+$ 5.2.4. Administration of CXCL12-Interacting Heparinoid In one aspect, the methods described herein comprise administering to a subject receiving an antineoplastic treatment regimen a CXCL12-interacting heparinoid, wherein the cancer is one that is privileged by CXCL12-CXCR4 interaction against therapeutic intervention. In certain embodiments, the cancer is one in which neoplastic cells, such as cancer stem cells, migrate to and/or reside in privileged anatomic sites. In some embodiments, the cancer is characterized by stromal expression of CXCL12. In embodiments, the CXCL12-interacting heparinoid is administered in an amount and at a time effective to enhance effectiveness of the antineoplastic treatment regimen.

In another aspect, the methods comprise administering to a subject receiving a treatment regimen for a hematopoietic stem cell disorder a heparin derivative capable of inhibiting binding of CXCL12 to CXCR4. The heparin derivative is administered in an amount and at a time effective to enhance effectiveness of the treatment regimen. 5.2.4.1. Routes of Administration The CXCL12-interacting heparinoid can be administered in the methods described herein by any one or more of a variety of routes.

In certain embodiments, the CXCL12-interacting heparinoid is administered intravenously. In certain embodiments, the CXCL12-interacting heparinoid is administered by bolus intravenous administration. In some embodiments, a bolus dose is administered over less than a minute, about a minute, about 2 minutes, about 3 minutes, about 4 minutes, or about 5 minutes. In some embodiments, the CXCL12-interacting heparinoid is administered by continuous intravenous infusion. In other embodiments, the CXCL12-interacting heparinoid is administered by subcutaneous injection. In some embodiments, the CXCL12-interacting heparinoid is administered as one or more bolus intravenous injections preceded and/or followed by continuous infusion.

5.2.4.2. Effective Amounts

The CXCL12-interacting heparinoid is administered in an amount effective to enhance efficacy of the treatment regimen. In methods of treating cancers, the CXCL12-interacting heparinoid is administered in an amount effective to enhance the efficacy of the antineoplastic treatment regimen. In methods of treating hematopoietic stem cell disorders, the CXCL12-interacting heparinoid is administered in an amount effective to enhance the efficacy of the treatment regimen used to treat the disordered HSC cells.

In some embodiments, the enhancement of treatment efficacy is with respect to one or more of the anti-tumor effect, the response rate (e.g., overall or objective response rate), the time to disease progression or the survival rate (e.g., progression free survival or overall survival). Anti-tumor effects include, but are not limited to, inhibition of tumor growth, tumor growth delay, regression of tumor, shrinkage of tumor, increased time to regrowth of tumor on cessation of treatment, and/or slowing of disease progression.

In typical embodiments, the CXCL12-interacting heparinoid is administered in an amount effective to mobilize neoplastic cells from a privileged anatomic site. Typically, the amount is effective to mobilize neoplastic cells from the bone marrow.

In some embodiments, the CXCL12-interacting heparinoid is administered in an amount effective to increase the number of cancer cells outside the bone marrow, e.g., in the peripheral blood and/or peripheral tissues. In some embodiments, the CXCL12-interacting heparinoid is administered in an amount effective to decrease the number of cancer cells in the bone marrow.

In preferred embodiments, the CXCL12-interacting heparinoid is administered in an amount effective to decrease the number of cancer cells in the bone marrow by at least 50%. In certain embodiments, the CXCL12-interacting heparinoid is administered in an amount effective to decrease the number of cancer cells in the bone marrow by at least 60%, at least 70%, at least 80%, or more. In specific embodiments, the CXCL12-interacting heparinoid is administered in an amount effective to decrease the number of cancer cells in the bone marrow by at least 85%, at least 90%, even by as much as 95% or more.

In certain embodiments, the diminution of cancer cells in the bone marrow is measured by visual inspection of bone marrow biopsies.

In some embodiments, the mobilization of bone-marrow residing cancer cells to the peripheral blood or tissues, and/or the decrease in the number of cancer cells in the bone marrow, is determined by detecting and quantifying a cancer cell marker or a set of cell markers distinctive for or indicative of the cancer cell.

In some embodiments, the cancer cell marker can include one or more of a cell surface marker, a cellular enzyme, a cellular genotype, and combinations thereof. By way of example and not limitation, markers useful for assessing mobilization of the relevant cancer cells are given below.

TABLE 2

| Cancer Type | Markers |
|---|---|
| Lung cancer | Adrenocorticotropic Hormone (ACTH) |
| | Calcitonin |
| | EGFR mutation |
| Breast cancer | Cancer Antigen 15-3 |
| | Cancer Antigen 549 |
| | C-erb B-2 |
| Prostate Cancer | Acid Phosphatase |
| | Prostate Specific Antigen |
| | Carcinoembryonic antigen |
| Kidney Cancer | PAX-2 |
| | Renal cell carcinoma marker antigen (RCCM) |
| | Kidney-specific cadherin (KSC) |
| Neuroblastoma | Cyclin D1 |
| | GALNT13 |
| | GD2 disialoganglioside |

TABLE 2-continued

| Cancer Type | Markers |
| --- | --- |
| Acute Lymphoblastic Leukemia | Neprilysin (CALLA antigen) |
| | TEL-AML1 fusion |
| Acute Myeloid Leukemia | NPM1 mutations |
| | FLT3 mutations |
| | CMBPA mutations |
| Chronic Lymphocytic leukemia | CD38 |
| | zeta-associated protein (ZAP)-70 |
| | IgVH mutations |
| Chronic Myelogenous Leukemia | Philadelphia Chromosome (Ph1: bcr-abl fusion) |
| Acute Monocytic Leukemia | CD13 |
| | CD33 |
| | CD11b, CD11c |

Methods for detecting the cell markers and cancer cells include, among others, flow cytometry (e.g., fluorescence activated cell sorting); immune detection (e.g., histochemistry); polymerase chain reaction (and other methods for detecting gene polymorphisms); fluorescence in situ hybridization; gene expression profiling; proteomics; morphological analysis; and combinations thereof. The sensitivity of each of the detection techniques can vary, and the appropriate method selected based on sensitivity appropriate for the treatment. For example, for acute myeloid leukemia (AML), detection sensitivity—the number of blast cells that can be detected per 100,000 cells—of standard detection approaches is as follows: morphological detection with immunohistochemistry can detect from about 1000 to about 5000 blast cells per 100,000 cells; karyotype analysis can detect about 5000 blast cells per 100,000 cells; flow cytometry can detect about 10 blast cells per 100,000 cells; and polymerase chain reaction can detect about 0.1 blasts per 100,000 cells. In some embodiments, the bone is imaged, for example with a MRI scan, a CT scan, and/or a PET scan to detect presence of cancer in the bone marrow, metastasis of cancers into the bone marrow, and/or any changes arising from administration of the CXCL12-interacting heparinoid.

In some embodiments, the CXCL12-interacting heparinoid is administered as an intravenous bolus. In certain embodiments, the CXCL12-interacting heparinoid is administered in an intravenous bolus of no more than about 1 mg/kg patient body weight. In typical intravenous bolus dosing embodiments, the CXCL12-interating heparinoid is administered at a dose of no more than about 25 mg/kg. In various embodiments, the CXCL12-interacting heparinoid is administered at an intravenous bolus dose of at least about 2 mg/kg, at least about 3 mg/kg, at least about 4 mg/kg, at least about 5 mg/kg, at least about 6 mg/kg, at least about 7 mg/kg, at least about 8 mg/kg, at least about 9 mg/kg, even at least about 10 mg/kg. In some embodiments, the bolus is at least about 15 mg/kg, even at least about 20 mg/kg. In certain preferred embodiments, the bolus is about 4 mg/kg. In certain other preferred embodiments, the bolus is about 8 mg/kg. In certain preferred embodiments, the bolus is about 20 mg/kg.

In some embodiments, the CXCL12-interacting heparinoid is administered in a bolus of from about 2 to about 25 mg/kg, from about 2 mg/kg to about 20 mg/kg, from about 2 mg/kg to about 15 mg/kg, from about 3 mg/kg to about 10 mg/kg, or from about 4 mg/kg to about 8 mg/kg.

In some embodiments, the CXCL12-interacting heparinoid is administered as an intravenous infusion. In certain embodiments, the infusion is at a dose rate of at least about 0.1 mg/kg/hr, at least about 0.2 mg/kg/hr, at least about 0.3 mg/kg/hr, at least about 0.4 mg/kg/hr, at least about 0.5 mg/kg/hr, at least about 1 mg/kg/hr, even at least about 2 mg/kg/hr. In various embodiments, the CXCL12-interacting heparinoid is administered at an infusion rate of no more than about 5 mg/kg/hr. In certain embodiments, the CXCL12-interacting heparinoid is administered at an infusion rate of no more than about 4 mg/kg/hr, 3 mg/kg/hr, about 2 mg/kg/hr, even no more than about 1 mg/kg/hr.

In typical embodiments, infusions at the above-described dose rates are administered continuously for up to 7 days. In certain embodiments infusions at the above-described dose rates are administered continuously for up to 6 days, 5 days, 4 days, or 3 days. In some embodiments, infusions at the above-described dose rates are administered continuously for up to 2 days or up to 24 hours. In some embodiments, infusions at the above-described rates are administered for up to 4 hours, 5 hours, 6 hours, 7 hours, 8 hours, 12 hours, 16 hours, or up to 24 hours or more. In certain embodiments, the infusions at the above described dose rates are administered for the duration of each cycle of treatment.

In some embodiments, the CXCL12-interacting heparinoid is administered as an initial bolus of about 20 mg/kg, optionally followed by an infusion of up to about 2 mg/kg/hour for up to about 4 hours, 8 hours, 12 hrs, 16 hours, even up to about 24 hours. In one embodiment, the CXCL12-interacting heparinoid is administered as an initial bolus of about 8 mg/kg, optionally followed by an infusion of about 0.5 mg/kg/hour for at least about 8 hours. In some embodiments, the CXCL12-interacting heparinoid is administered as an intravenous bolus at a dose of about 4 mg/kg, optionally followed by an intravenous infusion of the CXCL12-interacting heparinoid at a dose of about 0.25 mg/kg/hr—about 0.375 mg/kg/hr for at least 24 hours. In some embodiments, the CXCL12-interacting heparinoid is administered as an intravenous bolus at a dose of about 4 mg/kg, followed by a continuous intravenous infusion at a rate of 0.25 mg/kg/hr for a total of 7 days. In some embodiments, the CXCL12-interacting heparinoid is administered as a 4 mg/kg bolus on Day 1 followed by a continuous intravenous infusion of 0.25 mg/kg/hr for days 1 through 5 of each 28-day cycle.

For subcutaneous administration, CXCL12-interacting heparinoid can be administered at doses ranging from about 25 mg to about 400 mg, about 50 mg to about 300 mg, or about 75 mg to about 200 mg, in volumes of 2.0 mL or less per injection. In some embodiments, the CXCL12-interacting heparinoid at the above-described dosages are administered subcutaneously each day for up to 7 days. In certain embodiments, the CXCL12-interacting heparinoid at the above-described dosages are administered subcutaneously each day for up to 6 days, 5 days, 4 days, or 3 days. In some embodiments, CXCL12-interacting heparinoid at the above-described dosages are administered subcutaneously for up to 2 days or up to 24 hours. In some embodiments, CXCL12-interacting heparinoid at the above-described dosages are administered subcutaneously each day for the duration of the cycle of treatment.

5.2.4.3. Effective Timings

In various embodiments, the CXCL12-interacting heparinoid is administered adjunctively with the antineoplastic treatment regimen. The terms "adjunctive administration", "adjunctively administering" or "administering adjunctive to" are used interchangeably herein to mean administering the CXCL12-interacting heparinoid in therapeutically effective temporal proximity to the antineoplastic treatment regimen, that is, in sufficient temporal proximity to administration of the antineoplastic treatment regimen as to enhance the efficacy of the antineoplastic treatment regimen. In some embodiments, the CXCL12-interacting heparinoid is administered prior to treatment with the antineoplastic treatment. In some embodiments, the CXCL12-interacting heparinoid is administered concurrently with treatment with the antineoplastic treatment regimen. In some embodiments, the CXCL12-interacting heparinoid is administered prior to and concurrently with the antineoplastic treatment regimen.

In the methods described herein, the antineoplastic treatment regimen can involve one or more of an induction therapy, one or more of a consolidation therapy, and/or one or more of a maintenance therapy. In some embodiments, the consolidation or maintenance therapy can be optional. For example, a treatment regimen can include an induction therapy followed by maintenance therapy, or an induction therapy followed by consolidation therapy without any maintenance therapy. It is also to be understood that each of induction therapy, consolidation therapy, and maintenance therapy can have one or more cycles of treatment. As such, in some embodiments, the induction therapy can have one or more cycles of induction treatment; the consolidation therapy can have one or more cycles of consolidation treatment; and the maintenance therapy can have one or more cycles of maintenance treatment.

Thus, in various embodiments, the CXCL12-interacting heparinoid is administered adjunctively to one or more cycles of induction therapy. In certain embodiments, the CXCL12-interacting heparinoid is administered adjunctively to one or more cycles of consolidation therapy. In some embodiments, the CXCL12-interacting heparinoid is administered adjunctively to one or more cycles of maintenance therapy.

In some embodiments, the CXCL12-interacting heparinoid is administered at a time sufficiently prior to treatment with the antineoplastic treatment regimen as to mobilize the cancer cells from the privileged anatomic site, such as the bone marrow, before administration of the antineoplastic agent(s). In some embodiments, the CXCL12-interacting heparinoid is administered at least about 1 hr to about 24 hr prior to treatment with the antineoplastic therapeutic agent. In some embodiments, the CXCL12-interacting heparinoid is administered at least 2 days or more, or 3 days or more prior to treatment with the antineoplastic therapeutic. In certain embodiments, the CXCL12-interacting heparinoid is administered both prior to and concurrently with the antineoplastic treatment regimen.

In some embodiments, the CXCL12-interacting heparinoid is administered prior to induction therapy, particularly prior to each cycle of induction therapy with an antineoplastic therapeutic. In some embodiments, the CXCL12-interacting heparinoid is administered at a high dose prior to the induction therapy, particularly prior to each cycle of induction therapy. In some embodiments, the CXCL12-interacting heparinoid is administered prior to, during and optionally, following, treatment with the antineoplastic therapeutic used in the induction therapy, such as by continuous administration, for example to keep cancer cells from reestablishing residence in the bone marrow or other privileged anatomic site.

In some embodiments, the CXCL12-interacting heparinoid is administered prior to consolidation therapy, particularly prior to each cycle of consolidation therapy with an antineoplastic therapeutic agent. In some embodiments, the CXCL12-interacting heparinoid is administered at a high to moderate dose prior to the consolidation therapy, particularly prior to each cycle of consolidation therapy. In some embodiments, the CXCL12-interacting heparinoid is administered prior to, during and optionally, following, treatment with the antineoplastic therapeutic used in the consolidation therapy, such as by continuous administration, for example to keep cancer cells from reestablishing residence in the bone marrow or other privileged anatomic sites.

In some embodiments, the CXCL12-interacting heparinoid is administered prior to maintenance therapy, particularly prior to each cycle of maintenance therapy. In some embodiments, the CXCL12-interacting heparinoid is administered at a high to moderate dose, particularly at a moderate dose, prior to maintenance therapy, particularly prior to each cycle of maintenance therapy. In some embodiments, the CXCL12-interacting heparinoid is administered prior to, during, and optionally following treatment with the antineoplastic therapeutic in the maintenance therapy used in the maintenance therapy, such as by continuous administration, for example to keep cancer cells from reestablishing residence in the bone marrow or other privileged anatomic sites.

In some embodiments, the CXCL12-interacting heparinoid is administered as an adjunct to induction therapy, and is administered at high dose. In some embodiments, the CXCL12-interacting heparinoid is administered as an adjunct to consolidation therapy, and is administered in a high dose to a moderate dose. In some embodiments, the CXCL12-interacting heparinoid is administered as an adjunct to maintenance therapy, particularly at a high to a moderate dose, more particularly a moderate dose of the CXCL12-interacting heparinoid.

In some embodiments, the subject is treated with a high dose of the CXCL12-interacting heparinoid prior to induction therapy with the antineoplastic therapeutic, followed by treatment with a high to moderate dose of the CXCL12-interacting heparinoid for each cycle of a consolidation and/or maintenance therapy with the antineoplastic therapeutic. In some embodiments, the subject is treated with a high dose of the CXCL12-interacting heparinoid prior to induction therapy with the antineoplastic therapeutic, followed by treatment with a high to moderate dose of the CXCL12-interacting heparinoid for each cycle of a consolidation therapy, and treatment with a high to moderate dose, particularly a moderate dose of the CXCL12-interacting heparinoid for each cycle of a maintenance therapy. In each cycle of treatment, the CXCL12-interacting heparinoid can be administered as a bolus prior to administration of the antineoplastic therapeutic. In some embodiments, the bolus administration can be followed by a continuous administration, particularly during and/or subsequent to treatment with the antineoplastic therapeutic.

As discussed above, in some embodiments, the CXCL12-interacting heparinoid is administered in coordination with the cycles of treatment with an antineoplastic therapeutic, particularly a non-myelosuppressive antineoplastic therapeutic.

In some embodiments the CXCL12-interacting heparinoid is administered in coordination with hypomethylation agents. In certain embodiments the hypomethylation agent is azacitidine. In certain embodiments, the azacitidine is administered at 75 mg/m$^2$ as a 15 minute intravenous infusion daily on days 1 through 5 of each 28-day cycle and a heparinoid is administered as a 4 mg/kg bolus on Day 1 followed by a continuous intravenous infusion of 0.25 mg/kg/hr for days 1 through 5 of each 28-day cycle.

An exemplary treatment protocol follows the following schedule: treatment cycle length: every 21 days for 4 cycles. On days 1 to 3 of each cycle, the subject is treated with an antineoplastic therapeutic, such as a non-myelosuppressive therapeutic. ODSH is administered as an 8 hour infusion, on days 1-5, of weeks 1, 2 and 3 and then on days 1-3 of subsequent cycles as an 8 hour infusion. The dose is about 8 mg/kg bolus followed by about 0.5 mg/kg/hour infusion. In some embodiments, the dose is about 20 mg/kg bolus followed by about 2 mg/kg/hour infusion, such as during the induction therapy.

5.2.4.4. Duration and Frequency of Administration

In typical embodiments, the CXCL12-interacting heparinoid is administered for up to 1 hour. In various embodiments, the CXCL12-interacting heparinoid is administered for up to 4 hours. In certain embodiments, the CXCL12-interacting heparinoid is administered for up to 6 hours, even up to 8 hours. In some embodiments, the CXCL12-interacting heparinoid is administered for up to 12 hours, 18 hours, even up to 24 hours. In certain embodiments, the CXCL12-interacting heparinoid is administered for up to 2 days, 3 days, 4 days, 5 days, 6 days, or a week or more. The CXCL12-interacting heparinoid can be administered, in some embodiments, for periods of more than a week, including 1 month, 2 months, 3 months or more.

Typically, CXCL12-interacting heparinoid administration is repeated. For example, in certain embodiments, heparinoid is administered once daily, twice daily, three times daily, four times daily, five times daily, every two days, every three days, every five days, once a week, once every two weeks, once a month, every other month, semi-annually, or annually. In some embodiments, the CXCL12-interacting heparinoid is administered at regular intervals over a period of several weeks, followed by a period of rest, during which no heparinoid is administered. For example, in some embodiments, CXCL12-interacting heparinoid is administered for one, two, three, or more weeks, followed by one, two, three, or more weeks without heparinoid administration. The repeated administration can be at the same dose or at a different dose. The CXCL12-interacting heparinoid can be administered in one or more bolus injections, one or more infusions, or one or more bolus injections followed or preceded by infusion.

The frequency of dosing can be based on and adjusted for the pharmacokinetic parameters of the CXCL12-interacting heparinoid and the route of administration. Dosages are adjusted to provide sufficient levels of the CXCL12-interacting heparinoid or to maintain the desired physiological effect, particularly a therapeutic effect. Any effective administration regimen regulating the timing and sequence of doses may be used, as discussed herein.

Accordingly, the pharmaceutical compositions can be administered in a single dose, multiple discrete doses, continuous infusion, sustained release depots, or combinations thereof, as required to maintain desired minimum level of the agent. Daily dosages may vary, depending on the specific activity of the particular heparinoid. Depending on the route of administration, a suitable dose may be calculated according to, among others, body weight, body surface area, or organ size. The final dosage regimen will be determined by the attending physician in view of good medical practice, considering various factors that modify the action of drugs, e.g., the agent's specific activity, the severity of the disease state, the responsiveness of the patient, the age, condition, body weight, sex, and the like. Additional factors that may be taken into account include time and frequency of administration, drug combination(s), reaction sensitivities, and tolerance/response to therapy. Further refinement of the dosage appropriate for treatment involving any of the formulations mentioned herein is done by the skilled practitioner, especially in light of the dosage information and assays disclosed, as well as the pharmacokinetic data observed in clinical trials. The amount and/or frequency of the dosage can be altered, increased, or reduced, depending on the subject's response and in accordance with standard clinical practice. The proper dosage and treatment regimen can be established by monitoring the progress of therapy using conventional techniques known to skilled artisans. Appropriate dosages may be ascertained through use of established assays for determining concentration of the CXCL12-interacting heparinoid in a body fluid or other sample together with dose response data.

In embodiments in which CXCL12-interacting heparinoid is administered to a subject in combination with other therapeutic agents, the CXCL12-interacting heparinoid is administered in a therapeutically effective temporal proximity to the treatment regimen with the other therapeutic. Administration of a CXCL12-interacting heparinoid can be concurrent with (at the same time), sequential to (at a different time but on the same day, e.g., during the same patient visit), or separate from (on a different day) the treatment with the other therapeutic. In some embodiments, the CXCL12-interacting heparinoid is administered concurrently, sequentially, and/or separately from the other agent or therapy being administered. When administered sequentially or separately, the CXCL12-interacting heparinoid can be administered before, after, or both before and after the other treatment.

In embodiments in which the CXCL12-interacting heparinoid is administered in combination with treatment with another therapeutic agent, the CXCL12-interacting heparinoid can be administrated via the same or different route as the other therapeutic administered in temporal proximity. In some embodiments, the CXCL12-interacting heparinoid is administered concurrently or sequentially by the same route. For example, in some embodiments, the CXCL12-interacting heparinoid and the other therapeutic are administered intravenously, either concurrently or sequentially. Optionally, as part of a treatment regimen, the CXCL12-interacting heparinoid can further be administered separately (on a different day) from the other therapeutic by a different route, e.g., subcutaneously. In some embodiments, the CXCL12-interacting heparinoid is administered intravenously on the same day, either at the same time (concurrently), a different time (sequentially), or both concurrently and sequentially with the other therapeutic, and is also administered subcutaneously on one or more days when the patient is not receiving other treatment. In some embodiments, the CXCL12-interacting heparinoid is administered concurrently or sequentially by a different route. Optionally, as part of a treatment regimen, the CXCL12-interacting heparinoid can further be administered separately (on a different day) from the other therapeutic by the same or different route as that by which the other therapeutic is administered.

Other methods for delivering CXCL12-interacting heparinoids in the methods presented herein can be adapted from those are described in U.S. Pat. No. 4,654,327, which describes oral administration of heparin in the form of a complex with a quaternary ammonium ion; U.S. Pat. No. 4,656,161, which describes a method for increasing the enteral absorbability of heparinoids by orally administering the drug along with a non-ionic surfactant such as polyoxyethylene-20 cetyl ether, polyoxyethylene-20 stearate, other polyoxyethylene (polyethylene glycol)-based surfactants, polyoxypropylene-1 5 stearyl ether, sucrose palmitate stearate, or octyl-beta-D-glucopyranoside; U.S. Pat. No. 4,703,042, which describes oral administration of a salt of polyanionic heparinic acid and a polycationic species; and U.S. Pat. No. 5,714,477, which describes a method for improving the bioavailability of heparinoids by administering in combination with one or several glycerol esters of fatty acids.

5.2.5. Optional Steps

In some embodiments, the method of treatment further comprises the step of measuring or determining the number of cancer cells mobilized by treatment with the CXCL12-interacting heparinoid, particularly prior to treatment with the antineoplastic therapeutic. For example, a measurement of the number of cancer cells can be taken prior to administration of the CXCL12-interacting heparinoid and subsequent to administration of the CXCL12-interacting heparinoid to determine the increase in the number of cancer cell mobilized by the CXCL12-interacting heparinoid treatment. However, it is to be understood that, in some embodiments, the treatments herein can be given before metastasis or even when no increase in peripheral cancer cells are measured, particularly given that in some cancers a reservoir of cancer cells can remain in the bone marrow at levels not readily detectable, for example where there is minimal residual disease. Moreover, mobilization per se need not be a requisite condition for treatment because the CXCL12-interacting heparinoid may dislodge the cancer cells sufficiently to increase susceptibility to the antineoplastic therapeutic without inducing movement of cancer cells to the peripheral blood or tissues.

5.3. Pharmaceutical Compositions And Unit Dosage Forms Of CXCL12-Interacting Heparinoids In the methods presented herein, the CXCL12-interacting heparinoid is administered in the form of a pharmaceutical composition.

In typical embodiments, the pharmaceutical composition comprises the CXCL12-interacting heparinoid and a pharmaceutically acceptable carrier, excipient, and/or diluent, and is formulated for parenteral administration.

5.3.1. Pharmaceutical Compositions Formulated for i.v. Administration

In certain embodiments, pharmaceutical compositions of the CXCL12-interacting heparinoid are formulated in volumes and concentrations suitable for intravenous administration. In some embodiments, the composition is formulated for bolus administration. In certain embodiments, pharmaceutical compositions of the CXCL12-interacting heparinoid are formulated in volumes and concentrations suitable for intravenous infusion.

Typical embodiments formulated for intravenous administration comprise the CXCL12-interacting heparinoid in concentrations of at least about 10 mg/ml. In various embodiments, the CXCL12-interacting heparinoid is present in a concentration of at least about 15 mg/ml, at least about 20 mg/ml, at least about 30 mg/ml, at least about 40 mg/ml, at least about 50 mg/ml. In certain embodiments, the CXCL12-interacting heparinoid is packaged in sterile-filled 10 ml glass vials containing an isotonic 50 mg/ml solution of heparinoid in buffered saline.

5.3.2. Pharmaceutical compositions formulated for s.c. administration

In Various Embodiments, the Pharmaceutical Composition is Formulated for Subcutaneous Administration.

In certain such embodiments, the CXCL12-interacting heparinoid is associated with multivalent cations. The term "associated", when used to describe the relationship between a heparinoid and a cation, means a chemically relevant association. The association may be as a salt, ion/counterion, complex, binding, coordination or any other chemically relevant association. The exact nature of the association will be readily apparent to a person of skill in the art depending on the form of the composition.

In various such embodiments, the multivalent cations are selected from cations having a charge of +2, +3, +4, or greater. In some embodiments, the multivalent cation is an ion that contains both positive and negative charges, with a net charge greater than +1. Exemplary multivalent cations include metal ions, amino acids, and other organic and inorganic cations. In certain embodiments, the ion is a metal ion that is $Zn^{2+}$, $Ca^{2+}$, $Mg^{2+}$ or $Fe^{2+}$. In a specific embodiment, the cation is $Ca^{2+}$. In another specific embodiment, the cation is $Mg^{2+}$.

In certain of the embodiments of pharmaceutical composition intended for subcutaneous administration, the CXCL12-interacting heparinoid is associated primarily with one species of multivalent cation. In other embodiments, the CXCL12-interacting heparinoid is associated with several different multivalent cation species. In specific embodiments, the CXCL12-interacting heparinoid is associated with $Mg^{2+}$ and $Ca^{2+}$.

In the multivalent cation embodiments, multivalent cations may be introduced to the CXCL12-interacting heparinoid composition at any step.

In one embodiment, the CXCL12-interacting heparinoid is substantially desulfated at the 2-O and 3-O positions, and the multivalent cation is present during alkaline hydrolysis of the heparin starting material. In certain embodiments, the multivalent cation is present as the chloride salt. In certain embodiments, the multivalent cation is present as the hydroxide salt. In one embodiment, the chloride salt is preferred for use during solution phase alkaline hydrolysis. In another embodiment, the hydroxide salt is preferred for use during solid phase alkaline hydrolysis. In another embodiment, the hydroxide salt is preferred for use when alkaline hydrolysis is performed as a paste. Certain multivalent cations may affect the level of desulfation if present during alkaline hydrolysis, and may be used to achieve desired levels of desulfation. The amount of the multivalent cation may be titrated to control the amount of desulfation as described in U.S. Pat. No. 5,296,471 at Example 4 therein.

Thus, when a multivalent cation is used during alkaline hydrolysis, the multivalent cation concentration used should be adjusted based on both the desired level of desulfation and the desired concentration of the final product. The molar multivalent cation concentration used during alkaline hydrolysis may be substantially less than the molar heparin concentration. Preferably, the molar ratio (multivalent cation:heparin) is about 0.1, 0.2, 0.3, 0.4, 0.5, 0.6, 0.7, 0.8, 0.9, 1.0, 1.1, 1.2, 1.3, 1.4, or 1.5, or any ranges composed of those values. Preferably, the concentration of the multivalent cation used during alkaline hydrolysis is about 0.01 mM, 0.05 mM, 0.1 mM, 0.5 mM, 1 mM, 5 mM, 10 mM, 20 mM, 50 mM, 100 mM, 250 mM, 500 mM or 1M or any range composed of those numbers.

In certain embodiments, primarily monovalent cations are present during the cold alkaline hydrolysis step, and the multivalent cation is added later, during reconstitution of the lyophilate. In a most preferred embodiment, either $MgCl_2$ or $CaCl_2$ is added at high concentration during reconstitution of the lyophilate.

The multivalent cation concentration used during reconstitution may be equal to the concentration of the cation used during alkaline hydrolysis. Preferably, the multivalent cation concentration is at least about 2-fold, 3-fold, 4-fold, 5-fold, 6-fold, 7-fold, 8-fold, 9-fold, 10-fold, 15-fold, 20-fold, 25-fold, 30-fold, 50-fold, 75-fold, 100-fold, 150-fold, 200- fold, 250-fold, 500-fold, or 1000-fold the concentration of the cation used during alkaline hydrolysis. Preferably, the concentration of the multivalent cation used during reconstitution is about 0.1 M, 0.5 M, 1 M, 2 M, 3 M, 4 M, 5M, or greater. Most preferably, the concentration is about 2 M.

Excess cations can be removed by any method known to those in the art. One preferred method of removing excess cations is the use of a desalting column. Another preferred method of removing excess cations is dialysis. After removal of excess ions, the solution preferably has about equal, 2-fold, 3-fold, 4-fold, 5-fold, 6-fold, 7-fold, 8-fold, 9-fold, 10-fold, 15-fold, 20-fold, 25-fold, 30-fold, 50-fold, 75-fold, 100-fold, 150-fold, 200-fold, 250-fold, 500-fold, or 1000-fold greater multivalent cation concentration to monovalent cation concentration. The solution may also be free or substantially free of monovalent cations.

In typical embodiments, the final concentration of CXCL12-interacting heparinoid in the pharmaceutical composition is between 0.1 mg/mL and 600 mg/mL. In certain embodiments, the final concentration of partially desulfated heparin in the pharmaceutical composition is between 200 mg/mL and 400 mg/mL.

In some embodiments, the concentration of heparinoid is greater than about 25 mg/mL. In certain embodiments, the concentration of heparinoid is greater than about 50 mg/mL. In a variety of embodiments, the concentration of heparinoid is greater than about 60 mg/mL, 70 mg/mL, 80 mg/mL, 90 mg/mL, or 100 mg/mL.

In specific embodiments, the CXCL12-interacting heparinoid is present in the pharmaceutical composition in a concentration greater than about 110 mg/mL, 120 mg/mL, 130 mg/mL, 140 mg/mL, 150 mg/mL, 160 mg/mL, 170 mg/mL, 180 mg/mL, or even greater than about 190 mg/mL or 200 mg/mL. In specific embodiments, the CXCL12-interacting heparinoid is present in the pharmaceutical composition at a concentration of about 175 mg/mL. In another embodiment, the CXCL12-interacting heparinoid is present in the pharmaceutical composition at a concentration of about 200 mg/mL. In one embodiment, the CXCL12-interacting heparinoid is present in the pharmaceutical composition at a concentration of 400 mg/mL.

In certain embodiments, the concentration of CXCL12-interacting heparinoid is 50 mg/mL to 500 mg/mL, 100 mg/mL to 400 mg/mL, or 150 mg/mL to 300 mg/mL. In specific embodiments, the concentration is 50 mg/mL, 100 mg/mL, 150 mg/mL, 200 mg/mL, 250 mg/mL, 300 mg/mL, 350 mg/mL, 400 mg/mL, 450 mg/mL or 500 mg/mL. In certain currently preferred embodiments, the concentration is 200 mg/mL, 300 mg/mL or 400 mg/mL.

In typical embodiments, the pharmaceutical composition has a viscosity of less than about 100 cP. In various embodiments, the pharmaceutical composition has a viscosity of less than about 80 cP. In certain embodiments, the pharmaceutical composition has a viscosity of less than about 60 cP. In particular embodiments, the pharmaceutical composition has a viscosity of less than about 20 cP.

In typical embodiments, the pharmaceutical composition has an osmolality less than about 2500 mOsm/kg. In various embodiments, the pharmaceutical composition has an osmolality between about 150 mOsm/kg and about 500 mOsm/kg. In certain embodiments, the pharmaceutical composition has an osmolality between about 275 mOsm/kg and about 300 mOsm/kg. In a particular embodiment, the pharmaceutical composition has an osmolality of about 285 mOsm/kg. In a specific embodiment, the pharmaceutical composition is isotonic.

6. EXAMPLES

Practice of the various embodiments of the treatment methods can be understood through reference to the following examples, which are provided by way of illustration and are not intended to be limiting.

6.1. Example 1: CX-01 ODSH Attenuates Myelosuppressive Side Effects Of Induction Chemotherapy In Treatment Of Acute Myeloid Leukemia, And Surprisingly Improves Remission Rate A single arm open-label clinical study was conducted at multiple trial sites (University of Utah, Georgia Regents University, and Medical University of South Carolina) in patients with newly diagnosed acute myeloid leukemia (AML) to confirm that ODSH could accelerate platelet and white blood cell (WBC) recovery in patients receiving induction chemotherapy with a regimen known to have myelosuppressive side effects.

All patients received the following standard ("7+3") induction regimen,
Idarubicin (12 mg/m$^2$/day) by short intravenous infusion on Days 1, 2, and 3; and
Cytarabine (100 mg/m$^2$) as a continuous intravenous infusion over 24 hours (Days 1 through 7).
All patients also received CX-01, a substantially 2-O, 3-O-desulfated heparin derivative (ODSH) as an intravenous bolus immediately after the idarubicin dose on Day 1, at a dose of 4 mg/kg, followed by a continuous intravenous infusion at a dose of 0.25 mg/kg/hr for a total of 7 days (Days 1 through 7).

ODSH was manufactured under cGMP conditions by Scientific Protein Labs (Waunakee, Wis.) by cold alkaline hydrolysis of USP porcine intestinal unfractionated heparin during lyophilization. This process removes 2-O and 3-O sulfates, leaving N-sulfates and 6-O sulfates and carboxylates largely intact (Fryer et al., *J. Pharmacol. Exp. Ther.* 282:208-2219 (1997)). Seven serial 1.2 kg batches of material have shown an average molecular weight of 11.7±0.3 kDa, low affinity for anti-thrombin III (Kd=339 μm, or 4 mg/ml) (vs. 1.56 μm or 22 μg/ml for UFH), and consistently reduced USP anticoagulant activity (7±0.3 U of anticoagulant activity/mg), anti-Xa activity (1.9±0.1 U/mg), and anti-IIa activity (1.2±0.1 U/mg) as compared with those of heparin (165-190 U/mg activity for all 3 assays). Drug product was formulated by Pyramid Laboratories (Costa Mesa, Calif.) in sterile-filled 10 ml glass vials containing an isotonic 50 mg/ml solution of sodium ODSH in buffered saline.

Twelve patients were enrolled. The median age was 56 (range 22-74). Based on cytogenetic, molecular, or antecedent hematologic disorder, 9 of 12 patients fell into the intermediate or poor risk categories. Patients did not receive growth factor support, that is, Neupogen or similar agents, during induction cycles. Complete remission at the end of the induction cycle was assessed using International Working Group (IWG) criteria (see, e.g., Cheson et al., *J. Clin. Oncol.* 21:4642 (2003)).

Platelet, neutrophil, and WBC recovery of the ODSH-treated AML patients was compared with the recovery in historical control patients receiving identical doses of idarubicin and cytarabine as induction therapy in a previous clinical study comparing idarubicin and daunorubicin in combination with cytarabine (Vogler et al., *J. Clin. Oncol.* 10(7):1103-11(1992)). In the previous study, 101 patients received idarubicin 12 mg/m$^2$ on days 1, 2, and 3 and cytarabine 100 mg/m$^2$ on days 1-7. Growth factors were not administered to any patient.

Table 3 compares hematologic recovery parameters as reported in the prior study to those observed in the current study in which patients additionally received ODSH, as described above.

TABLE 3

| | Idarubicin + Cytarabine (n = 101) | Idarubicin + Cytarabine + ODSH (n = 12) |
|---|---|---|
| Time to platelet count >50,000 | 35 days | 22 days |
| Time to WBC >1000 | 31 days | 21 days |

In the current study, 11 out of 12 patients (92%), including two patients who received an incomplete course of chemotherapy (3 and 5 days, respectively), had a morphologic complete remission by IWG criteria at the end of a single induction cycle. The only patient who did not obtain a complete morphologic remission at the end of induction therapy presented with extensive mediastinal and peripheral lymphadenopathy involved with granulocytic sarcomas, accompanying bone marrow involvement with AML. This patient had residual extramedullary disease at the end of his induction cycle, and achieved a complete remission with a subsequent cycle of FLAG-Ida chemotherapy without ODSH.

With 9 of 12 patients having intermediate or poor risk disease prior to treatment, and with two of these patients having received an incomplete course of treatment, the 92% complete remission rate after the first induction cycle is higher than would otherwise be expected based on historical data, as shown in Table 4.

TABLE 4

| | Idarubicin + Cytarabine (n = 101) | Idarubicin + Cytarabine + ODSH (n = 12) |
|---|---|---|
| Complete response with first induction cycle | 58% | 92% |

Furthermore, 10 of the 12 patients remain in complete remission 5-13 months after having been enrolled in the study.

FIG. 3 compares complete response rate of the 11 patients who entered the clinical trial with primary AML to historical controls, indicated by asterisk. The historical controls are 1,980 patients registered to 6 studies conducted by the Eastern Cooperative Oncology Group (data from Rowe et al., Cancer 116(21):5012-5021 (2010).

Post-Induction Treatment and Outcomes

Of the 12 patients enrolled, 4 were not eligible to receive post-induction treatment on study due to either age ≥60 years, induction failure, or incomplete induction. Of the other patients, one developed a line-associated deep venous thrombosis requiring systemic anticoagulation and was taken off study before consolidation. The remaining 4 patients each received one or more cycles of HIDAC and CX-01 consolidation treatment on study as follows: Patient 1005 completed all four cycles on study; Patient 1009 received 3 cycles of consolidation on study and asked to be taken off study before receiving the fourth cycle of HIDAC consolidation; Patient 3001 completed 1 consolidation cycle, withdrew from study and was lost to follow-up; and Patient 3003 received 2 cycles of consolidation on study before relapsing. Four patients who completed induction received an allogeneic stem cell transplant in CR1 (Patients 1002, 1006, 1010, and 3002). Six patients relapsed at a median time of 8 months. Among those were Patient 2001 who had not completed induction and relapsed 7 weeks after diagnosis and Patient 3001 who received only 1 cycle of consolidation therapy, and relapsed 13.5 months after diagnosis.

With a median follow-up of 14.2 months, median event free survival is 13.5 months and median OS is 13.6+ months.

6.2. Example 2: CX-01 ODSH Mobilizes Cells of Multiple Lineages From Bone Marrow Bone marrow biopsies were obtained in the AML, trial described in Example 1.

FIGS. 2A-2C are photomicrographs of biopsies from one of the patients. FIG. 2A is a photomicrograph prior to treatment, and shows the bone marrow packed with leukemia cells. FIG. 2B is a photograph of bone marrow at day 14 of the induction cycle, showing elimination of leukemia cells, as expected, and additionally showing an unexpected and significant depletion of normal bone marrow cells. FIG. 2C shows the bone marrow at Day 28, showing no evidence of leukemia and restoration of normal bone marrow appearance and function.

The unexpected clearing of the marrow seen in the Day 14 marrow suggests that the increased remission rate observed in the current trial can be attributed to ODSH-mediated mobilization of leukemic cells from the marrow into the peripheral circulation, where they became vulnerable to the infusions of cytarabine and idarubicin. Retention of leukemic cells in the bone marrow is known to make them more resistant to chemotherapy (Hope et al., Nat. Immunol. 5:738-742 (2004)).

The recovery by Day 28 demonstrates further that the ODSH-mediated flushing of cells from the marrow does not adversely affect the ability of the marrow to repopulate and support multi-lineage hematopoiesis. Indeed, the accelerated recovery of platelet and white cell count, consistent with observations from a previous trial in pancreatic cancer, demonstrates that the marrow microenvironments required for thrombopoiesis, erythropoiesis, and granulopoiesis remain healthy.

6.4. Example 4: Phase II Clinical Trial for the Treatment of MDS with CX-01 ODSH and Azacitidine A pilot phase IIa study is conducted to confirm and quantify the therapeutic effect of adding CX-01 (2-O, 3-O-desulfated heparin derivative) to azacitidine in the treatment of recurrent or refractory myelodysplastic syndrome.

6.4.1. Primary Objective

The primary objective of the clinical study is to quantify the effect on complete response and near complete response rate (CR with incomplete count recovery) after combination therapy with CX-01 and azacitidine in patients with MDS.

6.4.2. Secondary Objectives

1. To quantify the partial response rate of combination therapy with CX-01 and azacitidine in patients with MDS
2. To quantify event free, progression free, disease free, 1-year survival, and overall survival of patients treated with CX-01 and azacitidine 3. To quantify hematologic improvement as determined by ANC, platelet and RBC response
4. To characterize and quantify the cytogenetic response as determined by reversion to normal karyotype

6.4.3. Overall Study Design and Plan Description

A pilot phase IIa, open-label trial is conducted to confirm safety and therapeutic effect of adding CX-01 to azacitidine in the treatment of recurrent or refractory myelodysplastic syndrome. CX-01 is administered as a 4 mg/kg bolus on Day 1 followed by a continuous intravenous infusion of 0.25 mg/kg/hr for Days 1 through 5 of each 28-day cycle. Azacitidine is administered at 75 mg/m$^2$ as a 15 minute intravenous infusion daily on Days 1 through 5 of each 28-day cycle.

Patients may continue treatment for up to 6 cycles or until they experience unacceptable toxicity that precludes further treatment, disease relapse or progression, and/or at the discretion of the investigator. Additional cycles may be administered after consultation with the Principle Investigator if a clear benefit is demonstrated for the patient.

A Data and Safety Monitoring Committee meets periodically to review the safety of the study. Adverse events (AEs) are collected from time of informed consent and continue until 30 days after last study treatment is administered.

6.4.4. Selection of Study Population

Inclusion Criteria: To be eligible to participate in the study, patients must meet the following criteria:
1. Male or female, 18 years of age or older.
2. Diagnosis of myelodysplastic syndrome and one of the following:
    a. Symptomatic anemia with either hemoglobin <10.0 g/dL or requiring RBC transfusion
    b. Thrombocytopenia with a history of two or more platelet counts <50,000/µL or a significant hemorrhage requiring platelet transfusions
    c. Neutropenia with two or more ANC <1,000/µL
3. IPS S score of INT-1 or higher at screening
4. Patient must have undergone ≥4 cycles of prior hypomethylating agent (decitabine or azacitidine) without response as defined by IWG criteria or have documented disease progression after prior response to hypomethylating agent therapy
5. ECOG performance status ≤2
6. >10% disease burden measured by cytomorphology, flow cytometry, or cytogenetics
7. Peripheral white blood cell count <50,000/µL.
8. Total bilirubin <1.5×ULN; AST/ALT <2.5×ULN,
9. Creatinine <2.0×ULN
10. Must be able to understand and willing to sign an IRB-approved written informed consent document.

Exclusion Criteria: Patients who meet any of the following criteria are not eligible to participate in the study:
1. Treatment with any other investigational therapeutic agent for the treatment of MDS within 7 days prior to study entry
2. Presence of significant active infection or congestive heart failure that is not controlled in the opinion of the Investigator
3. Presence of significant active bleeding
4. CNS leukemia
5. Positive HIV or hepatitis C serology
6. Known allergies, hypersensitivity, or intolerance to any form of heparin
7. Patients receiving any form of anticoagulant therapy (heparin flushes for IV catheter are permitted)
8. Psychiatric or neurologic conditions that could compromise patient safety or compliance, or interfere with the ability to give proper informed consent Withdrawal and Discontinuation of Patients: Patients are free to withdraw consent and/or discontinue participation in the study at any time, without prejudice to further treatment. A patient's participation in the study may also be discontinued at any time at the discretion of the Investigator or Sponsor.

The following may be justifiable reasons for the Investigator or Sponsor to discontinue a patient from treatment:
  The patient was erroneously included in the study (i.e. was found to be ineligible)
  The patient experiences an intolerable or unacceptable AE
  The patient is unable to comply with the requirements of the protocol
  The patient participates in another investigational study without the prior written authorization of the Sponsor or its designee
  The patient's participation in the study presents a significant safety concern.

Patients who experience Grade 4 increases in AST, ALT or bilirubin (e.g., increase in AST or ALT >20×ULN; increase in total bilirubin to >10×ULN) are discontinued from the study, if the Investigator judges that the laboratory abnormalities are potentially related to study treatment. Patients discontinued for this reason are not re-challenged and are followed until resolution of abnormal liver function tests. Patients who are discontinued from study due to an AE are closely monitored until the resolution or stabilization of the AE. Patients who received at least one dose of study drug and who are discontinued from treatment, but not withdrawn from the study, are asked to complete all evaluations for early termination (Early Termination/End of Study Visit). Patients who discontinue from the study are not replaced.

6.4.5. Treatment Of Patients

6.4.5.1. Treatments Administered

CX-01 is administered as a 4 mg/kg bolus on Day 1 followed by a continuous intravenous infusion of 0.25 mg/kg/hr for Days 1 through 5 of each 28-day cycle. Azacitidine is administered at 75 mg/m$^2$ as a 15 minute intravenous infusion daily on Days 1 through 5 of each 28-day cycle. Patients may continue treatment for up to 6 cycles or until they experience unacceptable toxicity that precludes further treatment, disease relapse or progression, and/or at the discretion of the investigator. Additional cycles may be administered after consultation with the Principle Investigator if a clear benefit is demonstrated for the patient.

6.4.5.2. Dosing and Method of Administration

Azacitidine and CX-01 doses are calculated based on actual body weight at the beginning of therapy.

Preparation of CX-01 Infusion

The Investigator and pharmacist at the investigational site ensures Good Pharmacy Practices are followed during the preparation of the CX-01 IV solution. The volumes and CX-01 concentration in the final CX-01 IV solutions must be verified to be correct based on the patient's actual body weight measured at the beginning of the cycle.

Preparation of CX-01 Intravenous Bolus Dose

The pharmacist prepares the IV bolus resulting from the 4 mg/kg dose calculation with the amount of CX-01 from the appropriate number of 2 mL or 10 mL vials. Each 1 mL solution contains 50 mg CX-01 and must be further diluted in 0.9% sodium chloride. The calculated volume per patient (based on weight) is added to 30 mL of 0.9% sodium chloride solution and the total volume administered IV over 5 minutes.

Preparation of CX-01 Continuous Infusion Dose

The pharmacist prepares each study treatment solution, adding the calculated amounts of CX-01 and 0.9% sodium chloride to an empty, sterile infusion bag. An IV infusion line is then attached to the infusion bag, and the infusion set purged with the CX-01 solution. A Luer lock (or similar) is then placed at the end of the set. As CX-01 doses are weight based, the amount of CX-01 from the vials and saline solution both vary by patient's weight. Each 1 mL solution contains 50 mg CX-01.

For each continuous infusion bag, an appropriate volume and concentration of CX-01 solution is prepared such that the patient receives a continuous infusion at the dose of CX-01 of 0.25 mg/kg/hour. The final volume of the CX-01 infusion is 500 to 1000 millimeters/24 hours. The infusion bags are prepared at a calculated CX-01 concentration based on the patient's actual body weight.

Based upon current stability testing data, CX-01 infusion solutions expire at room temperature 72 hours after preparation and should be stored in a refrigerator (2 to 8° C.) until used.

If the IV infusion is interrupted for any reason, the time of infusion stop is recorded, along with the reason. The IV infusion is restarted as soon as possible, and the restart time recorded. The planned cycle days of treatment administration is not altered, nor is the concentration of the CX-01 solution adjusted, to compensate for an interrupted CX-01 infusion.

Azacitidine Dose Modifications

For patients with baseline (start of treatment) WBC ≥3.0× $10^9$/L, ANC ≥1.5×$10^9$/L, and platelets ≥75.0×$10^9$/L, adjust the dose as follows, based on nadir counts for any given cycle:

| Nadir Counts | | % Dose in the Next Course |
|---|---|---|
| ANC (×$10^9$/L) | Platelets (×$10^9$/L) | |
| <0.5 | <25.0 | 50% |
| 0.5-1.5 | 25.0-50.0 | 67% |
| >1.5 | >50.0 | 100% |

For patients whose baseline counts are WBC <3.0×$10^9$/L, ANC<1.5×$10^9$/L, or platelets <75.0×$10^9$/L, dose adjustments should be based on nadir counts and bone marrow biopsy cellularity at the time of the nadir as noted below, unless there is clear improvement in differentiation (percentage of mature granulocytes is higher and ANC is higher than at onset of that course) at the time of the next cycle, in which case the dose of the current treatment should be continued.

| WBC or Platelet Nadir | Bone Marrow Biopsy Cellularity at Time of Nadir (%) | | |
|---|---|---|---|
| % decrease in counts from baseline | 30-60 | 15-30 | <15 |
| | % Dose in the Next Course | | |
| 50 – 75 | 100 | 50 | 33 |
| > 75 | 75 | 50 | 33 |

If a nadir as defined in the table above has occurred, the next course of treatment should be given 28 days after the start of the preceding course, provided that both the wbc and the platelet counts are >25% above the nadir and rising. The next course of treatment should be given 28 days after the start of the preceding course, provided that both the wbc and the platelet counts are >25% above the nadir and rising. If a >25% increase above the nadir is not seen by day 28, counts should be reassessed every 7 days. If a 25% increase is not seen by day 42, then the patient should be treated with 50% of the scheduled dose.

CX-01 Dose Modifications

CX-01 is temporarily discontinued in patients who develops aPTT above 45 seconds during continuous infusion of CX-01 and at least 8 hours after the bolus dose of CX-01, until the aPTT is <35 seconds. CX-01 will then be resumed at a 50% dose reduction. If the aPTT rises above 45 seconds at the reduced dose, CX-01 is permanently discontinued. If aPTT at the 50% reduced dose is <35 seconds, 4 hours or more after dose reduction, the dose can be escalated by 25%. If the aPTT after dose escalation again rises above 45 seconds at the reduced dose, the CX-01 is temporarily discontinued until the aPTT is <35 seconds, and then resumed at the previous 50% dose reduction.

Permitted Concomitant Medications

The use of myelopoietic growth factors (G-CSF and GM-CSF) is allowed.

6.4.5.3. Response Criteria

Patients are assessed for response according to the IWG criteria:

Complete Remission (CR)—Defined as <5% myeloblasts with normal maturation of all cell lines in the bone marrow and peripheral blood values of Hgb >11 g/dL, Platelets >100×$10^9$/L, Neutrophils >1.0×10/L, and 0% blasts. Persistent dysplasia does not exclude CR but will be noted.

Marrow Complete Response (Marrow CR)-Defined as <5% myeloblasts in the bone marrow and a decrease by >50% from pre-treatment values, but not meeting the definition of CR above.

Partial Remission (PR)-Defined as meeting the definition of CR above with a decrease of myeloblasts in the bone marrow by >50% from pre-treatment values, but absolute myeloblasts still >5%.

Stable Disease (SD)—Defined as not meeting the definitions of CR, Marrow CR, PR, SD, PD, or recurrence/morphologic relapse.

Progressive Disease/Relapse (PD)-Defined as ≥50% increase in blasts to >5% blasts (for patients with less than 5% blasts at baseline only), ≥50% increase to >10% blasts (for patients with 5-10% blasts at baseline only), ≥50% increase to >20% blasts (for patients with 10-20% blasts at baseline only), >50% increase to >30% blasts (for patients with 20-30% blasts at baseline only) or any of the following: At least 50% decrement from maximum remission/response in granulocytes or platelets, reduction in Hgb by ≥2 g/dL, or New or worsened transfusion dependence not related to study drug toxicity. Or for patients with a CR, Marrow CR, or PR as defined above and subsequently development of one of the following: Return to pre-treatment bone marrow blast percentage, decrement of ≥50% from maximum remission/response levels in granulocytes or platelets, or reduction in Hgb concentration by ≥1.5 g/dL or transfusion dependence.

Hematologic Improvement

Progressive disease as defined above nullifies hematologic improvement.

Erythroid response requires all of the following (only required if pre-treatment Hgb <11 g/dL):

Hgb increase by ≥1.5 g/dL

Relevant reduction of units of RBC transfusions by an absolute number of at least 4 RBC transfusions/8 week compared with the pre-treatment transfusion number in the previous 8 weeks. Only RBC transfusions given for a Hgb of ≤9.0 g/dL pre-treatment will count in the RBC transfusion response evaluation Platelet response requires one of the following (only required if pre-treatment platelets <100×10$^9$/L).

Absolute increase of ≥30×10$^9$/L (for patients starting with >20×10$^9$/L platelets)

Increase from <20×10$^9$/L to >20×10$^9$/L and absolute increase >100% (for patients starting with <20×10$^9$/L)

Neutrophil response requires the following (only required if pre-treatment ANC <1.0×10$^9$/L):

At least 100% increase and an absolute increase >0.5× 10$^9$/L

Cytogenetic Response

Cytogenic Response is defined as reversion to a normal karyotype. For this study, reversion of a normal karyotype is defined as no clonal abnormalities detected in a minimum of 20 mitotic cells. Progressive disease as defined above nullifies cytogenetic response.

6.4.6. Results

Addition of CX-01 ODSH, a CXCL12-interacting heparinoid, improves at least one of the above-described response criteria (see Section 5.4.5.3).

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A method of treating myelodysplastic syndromes (MDS), comprising:
   adjunctively administering to a subject with a myelodysplastic syndrome who is receiving a hypomethylating agent, a heparinoid substantially desulfated at the 2-O position and 3-O position, in an amount and at a time effective to enhance effectiveness of the hypomethylating agent.

2. The method of claim 1, wherein the hypomethylating agent is azacitidine.

3. The method of claim 1, wherein the heparinoid is at least 85% desulfated at the 2-O position.

4. The method of claim 1, wherein the heparinoid is at least 85% desulfated at the 3-O position.

5. The method of claim 1, wherein the heparinoid has an average molecular weight of about 8 kDa to about 15 kDa.

6. The method of claim 1, wherein the heparinoid is administered subcutaneously.

7. The method of claim 1, wherein the heparinoid is administered intravenously.

8. The method of claim 7, wherein the heparinoid is administered as one or more bolus injections.

9. The method of claim 8, wherein the bolus dose is 2 mg/kg-25 mg/kg.

10. The method of claim 7, wherein the heparinoid is administered as a continuous infusion.

11. The method of claim 10, wherein the continuous infusion is administered at a dose of 0.1 mg/kg/hr-5 mg/kg/hr.

12. The method of claim 7, wherein the heparinoid is administered as a bolus injection followed by continuous infusion.

13. The method of claim 12, wherein the heparinoid is administered as a 4 mg/kg bolus followed by a continuous infusion of 0.25 mg/kg/hr.

14. The method of claim 1, wherein the heparinoid is administered prior to the hypomethylating agent.

15. The method of claim 1, wherein the heparinoid is administered in combination with the hypomethylating agent.

16. The method of claim 15, wherein the heparinoid is administered in combination with azacitidine.

17. The method of claim 16, wherein the azacitidine is administered intravenously at a dose of 5 mg/m$^2$-500 mg/m$^2$.

18. The method of claim 17, wherein the heparinoid is administered as a bolus injection at a dose of 4 mg/kg followed by a continuous intravenous infusion at a dose of 0.25 mg/kg/hr; and wherein azacitidine is administered at a dose of 75 mg/m$^2$ as a 15 minute intravenous infusion.

19. A method of treating myelodysplastic syndromes (MDS), comprising:
   administering to a subject with MDS, a heparinoid substantially desulfated at the 2-O position and 3-O position and azacitidine, comprising:
   administering the heparinoid as a bolus injection at a dose of 4 mg/kg on Day 1 followed by a continuous intravenous infusion at a dose of 0.25 mg/kg/hr for Days 1 through 7 of at least one 28-day cycle; and
   administering azacitidine as an intravenous infusion at a dose of 75 mg/m$^2$ as a 15 minute intravenous infusion daily on Days 1 through 7 of the at least one 28-day cycle.

* * * * *